(12) United States Patent
Zhao et al.

(10) Patent No.: US 12,091,684 B2
(45) Date of Patent: Sep. 17, 2024

(54) PLATELET-DERIVED MITOCHONDRIA TREATMENT AND METHOD OF GENERATING MULTIPOTENT CELLS

(71) Applicant: Hackensack Meridian Health, Inc., Hackensack, NJ (US)

(72) Inventors: Yong Zhao, Nutley, NJ (US); Haibo Yu, Changsha (CN); Wei Hu, Union City, NJ (US); Xiang Song, River Edge, NJ (US)

(73) Assignee: Hackensack Meridian Health, Inc., Edison, NJ (US)

( * ) Notice: Subject to any disclaimer, the term of this patent is extended or adjusted under 35 U.S.C. 154(b) by 139 days.

(21) Appl. No.: 17/176,907

(22) Filed: Feb. 16, 2021

(65) Prior Publication Data

US 2021/0254007 A1    Aug. 19, 2021

Related U.S. Application Data

(60) Provisional application No. 62/976,830, filed on Feb. 14, 2020.

(51) Int. Cl.
| | |
|---|---|
| C12N 5/0789 | (2010.01) |
| A61K 35/17 | (2015.01) |
| A61K 35/30 | (2015.01) |
| C12N 5/0783 | (2010.01) |
| C12N 5/079 | (2010.01) |
| C12N 5/0793 | (2010.01) |

(52) U.S. Cl.
CPC ............ *C12N 5/0647* (2013.01); *A61K 35/17* (2013.01); *A61K 35/30* (2013.01); *C12N 5/0619* (2013.01); *C12N 5/0621* (2013.01); *C12N 5/0636* (2013.01); *C12N 2506/11* (2013.01)

(58) Field of Classification Search
None
See application file for complete search history.

(56) References Cited

U.S. PATENT DOCUMENTS

| | | | |
|---|---|---|---|
| 8,835,163 B2 * | 9/2014 | Zhao | A61K 35/17 435/363 |
| 2015/0110749 A1 | 4/2015 | Vacanti et al. | |
| 2018/0055891 A1 * | 3/2018 | Zhao | C12N 5/0676 |

FOREIGN PATENT DOCUMENTS

| | | |
|---|---|---|
| WO | 2018044795 | 3/2018 |

OTHER PUBLICATIONS

"International Search Report and Written Opinion, PCT/US21/18228".

Agulinick, et al., "Insulin-Producing Endocrine Cells Differentiated In Vitro From Human Embryonic Stem Cells Function in Macroencapsulation Devices In Vivo".
Akashi, et al., "A clonogenic commonmyeloid progenitor that gives rise to allmyeloid lineages".
Andrzejewska, et al., "Concise Review: Mesenchymal Stem Cells: From Roots to Boost".
Anjos, et al., "CD34-Cells at the Apex of the Human Hematopoietic Stem Cell Hierarchy Have Distinctive Cellular and Molecular Signatures".
Ao, Jack, et al., "Retinal pigment epithelium in the pathogenesis of age-related macular degeneration and photobiomodulation as a potential therapy?".
Asmussen, et al., "Regulation of Extracellular Matrix Vesicles via Rapid Responses to Steroid Hormones during Endochondral Bone Formation".
Bapat, et al., "Depletion of fat-resident Treg cells prevents age-associated insulin resistance".
Bemal, et al., "Human b-Cell Proliferation and Intracellular Signaling Part 2: Still Driving in the Dark Without a Road Map".
Blaser, et al., "Making HSCs in vitro: don't forget the hemogenic endothelium".
Bloom, et al., "A Nucleus With Cytoplasmic Features".
Bluestone, et al.
Boyd, et al.
Brandes, et al., "Nuclear Mitochondria".
Butko, et al., "Complex regulation of HSC emergence bythe Notchsignalingpathway".
Calloni, et al., "Reviewing and Updating the Major Molecular Markers for Stem Cells".
Chabannon, et al., "Hematopoietic stem cell transplantation in its 60s: A platform for cellular therapies".
Chichagova, et al., "Cellular regeneration strategies for macular degeneration: past, present and future".
Daubner, et al., "Tyrosine hydroxylase and regulation of dopamine synthesis".
De Obaldia, et al., "Transcriptional Regulation of Innate and Adaptive Lymphocyte Lineages".
Defronzo, et al., "Type 2 diabetes mellitus".
Defuria, et al., "B cells promote inflammation in obesity and type 2 diabetes through regulation of T-cell function and an inflammatory cytokine profile".

(Continued)

*Primary Examiner* — Allison M Fox
*Assistant Examiner* — Alyssa G Weston
(74) *Attorney, Agent, or Firm* — McCarter & English, LLP; Beverly W. Lubit

(57) ABSTRACT

A method of generating multipotent stem cells from adult human peripheral blood cells by isolating the peripheral blood insulin-producing cells and exposing them to adult peripheral blood-derived mitochondria. Adult peripheral blood insulin-producing cells (PB-IPC) are isolated from adult peripheral blood by adherence to a hydrophobic surface with a positive charge, such as a Petri dish. Once the PB-IPC are isolated, mitochondria derived from adult peripheral blood are applied to the isolated PB-IPC. The mitochondria are then taken in by the PB-IPC and enter the nuclei of the PB-IPC, allowing the cells to be reprogrammed, transforming PB-IPC into multipotent stem cells and giving rise to three germ layer-derived cells. Additionally, PB-IPC give rise to functional CD34+ hematopoietic stem cell (HSC)-like cells after treatment with adult peripheral blood-derived mitochondria.

18 Claims, 39 Drawing Sheets

Specification includes a Sequence Listing.

(56) References Cited

OTHER PUBLICATIONS

Delgado, et al., "Modulation of Autoimmune T-Cell Memory by Stem Cell Educator Therapy: Phase 1/2 Clinical Trial".
Doulatov, et al., "Hematopoiesis: A Human Perspective".
Doulatov, et al., "Induction of Multipotential Hematopoietic Progenitors from Human Pluripotent Stem Cells via Respecification of Lineage-Restricted Precursors".
Finneman, et al.
Gambell, et al., "Peripheral Blood CD341 Cell Enumeration as a Predictor of Apheresis Yield: An Analysis of More Than 1,000 Collections".
Gori, et al., "Vascular niche promotes hematopoietic multipotent progenitor formation from pluripotent stem cells".
Hao, et al., "Identification of a novel, human multilymphoid progenitor in cord blood".
Jensen, et al., "Ultrastructure of Mitochondria-Containing Nuclei in Human Myocardial Cells".
Kanakry, et al., "Modern approaches to HLA-haploidentical blood or marrow transplantation".
Kelly, et al., "C ell-surface markers for the isolation of pancreatic cell types derived from human embryonic stem cells".
Krebsbach, et al., "The Role of Integrin a6 (CD49f) in Stem Cells: More than a Conserved Biomarker".
Kroon, et al., "Pancreatic endoderm derived from human embryonic stem cells generates glucose-responsive Insulin-secreting cells in vivo".
Kushner, et al., "Stem Cells to Insulin Secreting Cells: Two Steps Forward and Now a Time to Pause?".
Li, et al., "Hair regrowth in alopecia areata patients following Stem Cell Educator therapy".
Liu, et al., "Genetic deficiency and pharmacological stabilization of mast cells reduce diet-induced obesity and diabetes in mice".
Lofty, et al., "Chronic Complications of Diabetes Mellitus: A Mini Review".
Matsuoka, et al., "The MafA transcription factor appears to be responsible for tissue-specific expression of insulin".
Nanditha, et al., "Effect of Long-Acting Insulin Analogs on the Risk of Cancer: A Systematic Review of Observational Studies".
Nishimura, et al., "Mechanisms of the Metabolic Shift during Somatic Cell Reprogramming".
Notta, et al., "Distinct Routes of Lineage Development Reshape the Human Blood Hierarchy Across Ontogeny".
Odorico, et al., "Report of the Key Opinion Leaders Meeting on Stem Cell-derived Beta Cells".
Okita, et al., "An Efficient Nonviral Method to Generate Integration-Free Human-Induced Pluripotent Stem Cells from Cord Blood and Peripheral Blood Cells".
Olefsky, et al., "Macrophages, Inflammation, and Insulin Resistance".
Rezania, et al., "Reversal of diabetes with insulin-producing cells derived in vitro from human pluripotent stem cells".
Schultz, et al., "Human Lymphoid and Myeloid Cell Development in NOD/LtSz-scid IL2Rgnull Mice Engrafted with Mobilized Human Hemopoietic Stem Cells".
Sneddon, et al., "Stem Cell Therapies for Treating Diabetes: Progress and Remaining Challenges".
Staal, et al., "Stem cell self-renewal: lessons from bone marrow, gut and iPS toward clinical applications".
Stewart, et al., "Human b-Cell Proliferation and Intracellular Signaling: Part 3".
Sugimura, et al., "Haematopoietic stem and progenitor cells from human pluripotent stem cells".
Swart, et al., "Haematopoietic stem cell transplantation for autoimmune diseases".
Takemura, et al., "Intranuclear Mitochondria in Human Myocardial Cells".
Talukdar, et al., "Neutrophils mediate insulin resistance in mice fed a high-fat diet through secreted elastase".
Tsai, et al., "Are Obesity-Related Insulin Resistance and Type 2 Diabetes Autoimmune Diseases?".
Veres, et al., "Charting cellular identity during human in vitro B-cell differentiation".
Wahlster, et al., "Progress towards generation of human haematopoietic stem cells".
Weber, et al., "Hey bHLH Transcription Factors".
Winer, D, et al., "B cells promote insulin resistance through modulation of T cells and production of pathogenic IgG antibodies".
Winer, Shawn, et al., "Normalization of obesity-associated insulin resistance through immunotherapy".
Winer, Shawn, et al., "The adaptive immune system as a fundamental regulator of adipose tissue inflammation and insulin resistance".
Wong, et al., "Diabetes and risk of physical disability in adults: a systematic review and meta-analysis".
Woods, et al., "Brief Report: Efficient Generation of Hematopoietic Precursors and Progenitors from Human Pluripotent Stem Cell Lines".
Wu, et al., "Eosinophils Sustain Adipose Alternatively Activated Macrophages Associated with Glucose Homeostasis".
Ku, et al., "Prevalence and Control of Diabetes in Chinese Adults".
Yamamoto, et al., "Clonal Analysis Unveils Self-Renewing Lineage-Restricted Progenitors Generated Directly from Hematopoietic Stem Cells".
Yu, et al., "Generation of Multipotent Stem Cells from Adult Human Peripheral Blood Following the Treatment with Platete-Derived Mitochondria", Cells, vol. 9, No. 1350, May 29, 2020, 1-18.
Zhao, et al., "A human peripheral blood monocyte-derived subset acts as pluripotent stem cells".
Zhao, et al., "A unique human blood-derived cell population displays high potential for producing insulin".
Zhao, et al., "Human cord blood stem cells and the journey to a cure for type 1 diabetes".
Zhao, et al., "Humanized Mice Reveal Differential Immunogenicity of Cells Derived from Autologous Induced Pluripotent Stem Cells".
Zhao, et al., "Identification of stem cells from human umbilical cord blood with embryonic and hematopoietic characteristics".
Zhao, et al., "Immunogenicity of induced pluripotent stem cells".
Zhao, et al., "Platelet-Derived Mitochondria Display Embryonic Stem Cell Markers and Improve Pancreatic Islet beta-cell Function in Humans", Stem Cells Translational Medicine, vol. 6, 2017, 1684-1697.
Zhao, et al., "Reversal of type 1 diabetes via islet b cell regeneration following immune modulation by cord blood-derived multipotent stem cells".
Zhao, et al., "Targeting insulin resistance in type 2 diabetes via immune modulation of cord blood-derived multipotent stem cells (CB-SCs) in stem cell educator therapy: phase I/II clinical trial".

* cited by examiner

PLATELET-DERIVED MITOCHONDRIA TREATMENT AND METHOD OF GENERATING MULTIPOTENT CELLS

CROSS-REFERENCE TO RELATED APPLICATION

This application claims priority in U.S. Provisional Patent Application No. 62/976,830, filed Feb. 14, 2020, which is incorporated herein by reference in its entirety.

REFERENCE TO A SEQUENCE LISTING SUBMITTED VIA EFS-WEB

The content of the ASCII text file of the sequence listing named "5700NP_and_PCT_Sequence_Listing_ST25," which is 1,595 KB in size and was created on Feb. 15, 2021 and electrically submitted via EFS-Web herewith the application, is incorporated herein by reference in its entirety.

BACKGROUND OF THE INVENTION

1. Field of the Invention

The present invention relates generally to medical treatments and, more specifically, to treating adult human peripheral blood cells with platelet-derived mitochondria to generate multipotent cells for treatment of chronic medical conditions.

2. Description of the Related Art

Many chronic medical conditions, including but not limited to cancers, Alzheimer's disease, and diabetes, affect the health of millions of people daily, yet treatments available for many of these conditions remain largely ineffective. Diabetes is a major public health concern which affects over 350 million people worldwide. Prevalence of diabetes exceeds 12.1% of the population in India, 11.6% in China, and 9.3% in the United States, and approximately one billion people worldwide are considered pre-diabetic, with higher than normal blood sugar levels. Diabetes is the sixth leading cause of death in the U.S. and is associated with increased risk for heart disease, stroke, kidney disease, blindness, and amputations.

A common factor in both type 1 diabetes (T1D) and type 2 diabetes (T2D) is immune system dysfunction. T1D is characterized by autoimmune destruction of pancreatic islet β cells and disruption of immune cells including T cells, B cells, regulatory T cells (Tregs), monocytes/macrophages (Mo/Mφs), dendritic cells (DCs), natural killer (NK) cells, and natural killer T (NKT) cells. While T2D is largely characterized by insulin resistance and aberrant production of insulin, chronic low-grade inflammation also occurs in peripheral tissues such as adipose tissue, the liver, and muscle tissue, further contributing to the disease. Specifically, studies have shown T cells to be unexpected promoters and controllers of insulin resistance. T cells promote recruitment of inflammatory macrophages to adipose depots and produce inflammatory cytokines, which promote the development of insulin resistance that can lead to diabetes. Despite more than 30 years of intense research, cures for both T1D and T2D remain elusive. Comprehensive immune modulation via both local and systematic approaches are needed to simultaneously address the multiple immune dysfunctions that underlie these diseases.

A deficit of insulin-producing cells is another crucial and common issue for diabetes patients. While supplemental insulin provides T1D patients a means to manage blood sugar, it is not a cure, and insulin does not address the underlying immune dysfunction that causes pancreatic islet β-cell destruction. To overcome the shortage of insulin-producing cells in diabetic patients, pancreas and islet transplantations have offered potential treatments for independence from insulin injections. However, donor scarcity and the risk of immune rejection severely hinders the potential for wide application of such transplantations. Thus, there remains a compelling need and sense of urgency to find a cure for diabetes that not only halts the progression of autoimmunity in T1D and corrects multiple immune dysfunctions in T2D, but also overcomes the shortage of insulin-producing β-cells.

Stem cell research has the potential to revolutionize treatments for certain life-changing injuries and human diseases, such as but not limited to diabetes, Alzheimer's disease, cancers, and alopecia areata. To date, researchers have characterized multiple types of human stem cells with varying potentials for regeneration, and animal studies and human trials have demonstrated the translational capability of stem cells to treat human diseases.

To date, functional insulin-producing cells or islet cells have been generated from embryonic stem (ES) cells and induced pluripotent stem cells (iPS) through ex vivo induction of differentiations. However, recent advances in stem cell biology have realized that ES cells, iPS, and their derived cells can also cause immune rejections post transplantation, challenging their clinical therapeutic potentials. Accordingly, encapsulation with different biomaterials and the use of a semipermeable membranes and capsules have been evaluated through animal and pilot clinical studies in an effort to avoid attack by immune cells on transplanted cells and/or cell-delivery devices and to provide sufficiently-permeabilized nutrients to sustain cell viability. However, formation of fibrosis, or scarring around the device, which causes death of capsulized cells and failure of encapsulation devices, is still a major roadblock, and the optimal membrane or capsule device has yet to be developed.

For over three decades now, the most common stem cell therapy approved by the U.S. Food and Drug Administration (FDA) has been hematopoietic cell transplantation (HCT) (also known as hematopoietic stem cell transplantation or HSCT). HCT has been approved for treatment of bone marrow failure, malignant blood disorders, genetic-based blood disorders, and autoimmune diseases as well as for post-chemotherapy and/or post-radiation cell regeneration. However, several major limitations have restricted the broad clinical application of allogeneic HCT. These limitations include the difficulty in identifying a human leukocyte antigen (HLA) fully-matched or haploidentical donor; the scarcity of hematopoietic stem cells (HSC), which are known to be identified by glycosylated transmembrane protein marker CD34, amongst all sources of harvested cells (≤1%); and most particularly, by the incidence of graft-versus-host disease (GVHD), opportunistic infections, relapse of primary disease, and toxicities associated with immunosuppressive drugs and radiation. An autologous source of HSC would address the problems of matching and GVHD, but engraftment could still be hampered by the limited number of CD34$^+$ HSC.

Since the success rate of engraftment for clinical HCT is correlated with the number of functional CD34$^+$ hematopoietic progenitor cells (HPC) and HSC in the transplant, researchers have evaluated whether embryonic stem (ES)

cells and/or induced pluripotent stem (iPS) cells can be manipulated to produce HSC through reprogramming by small molecules or by viral transduction of transcription factors. Thus far, these approaches have been limited by an inability to generate true functional HSC in sufficient numbers for therapeutic use, as well as safety and ethical concerns and potential immune rejection issues to ES or iPS derivatives.

The use of autologous stem cells for regenerative medicine is more ethically acceptable and likely more successful than the use of other stem cells, and such therapies would avoid many of the immune rejection and safety concerns associated with other stem cells (e.g., ES- or iPS-based therapies). What is needed is a method of generating autologous multipotent cells for use in regenerative medicine.

Heretofore there has not been available a method for generating multipotent cells for medical treatment with the advantages and features of the present invention.

SUMMARY OF THE INVENTION

The present invention discloses a method of generating multipotent stem cells from adult human peripheral blood cells by isolating the peripheral blood insulin-producing cells and exposing them to platelet-derived mitochondria. In an aspect of the present invention, adult peripheral blood insulin-producing cells (PB-IPC) are isolated from adult peripheral blood via attachment to a hydrophobic surface with a positive charge. Once the PB-IPC are isolated, mitochondria derived from platelets are applied to the isolated PB-IPC. The mitochondria are then taken in by the PB-IPC and enter the nuclei of the PB-IPC, allowing the cells to be reprogrammed, transforming PB-IPC into multipotent stem cells and giving rise to three germ layer-derived cells.

PB-IPC can be easily isolated from peripheral blood and expanded in serum-free culture medium to avoid the painful and invasive procedures required to withdraw bone marrow. Using autologous PB-IPC from patients as a starting material, mitochondrial treatment can generate functional autologous mitochondrion-induced peripheral blood insulin-producing cells (miPB-IPC) on a large scale, giving rise to different cell lineages. Differentiation of these miPB-IPC into multiple lineages at high efficiency, such as T cells, B cells, monocytes/macrophages (MΦ), granulocytes (Gr), erythrocytes (Er), megakaryocytes (MKs)/platelets, retinal pigment epithelium (RPE), and neuronal cells, demonstrates the multipotency of PB-IPC post-mitochondrial reprogramming. Thus, these cells offer great promise as a solution for the current bottlenecks associated with conventional stem cell transplants and have tremendous potential for patient benefit in the clinic.

PB-IPC naturally circulates in human peripheral blood, displaying islet β cell-related markers and reducing hyperglycemia with migration to pancreatic islets. The present invention provides a novel approach for the generation of a large amount of autologous insulin-producing cells from patients themselves to potentially treat diabetes in clinics after optimizing ex vivo culture conditions. In contrast with the generation of insulin-producing cells from ES and iPS cells, the present technology can efficiently isolate insulin-producing cells from their own blood, without any ethical issues and without the hazards of immune rejection. Moreover, multipotent differentiation of miPB-IPC into other cell lineages accommodates treatment for not only diabetic subjects but for the whole field of regenerative medicine.

In another aspect of the present invention, PB-IPC give rise to functional CD34+ hematopoietic stem cell (HSC)-like cells after treatment with platelet-derived mitochondria, designated herein as mitochondrion-induced CD34+ HSC (miCD34+ HSC). The miCD34+ HSC of the present invention can reconstitute multi-lineage blood cells in peripheral blood, the spleen, and bone marrow after transplant into irradiated NSG mice at 12 weeks, including but not limited to T cells (CD3+CD4+), B cells (CD19+), monocytes/macrophages (CD14+), granulocytes (CD66b+), erythroid cells (CD235a+), and megakaryocytes/platelets (CD41b+), highlighting the high potential to treat hematopoietic-associated diseases.

The capacity of self-renewal is one of the major characteristics for CD34+ HSC. The miCD34+ HSC exhibit a rapid multiple potential for differentiation, with a limited potential of self-renewal, meaning the mitochondrial reprogramming, differentiating the PB-IPC into CD34+ HSC-like cells with expressions of HSC-associated cell surface markers and primarily improving their multi-potency of differentiation potential, does not significantly change their capability of self-renewal.

BRIEF DESCRIPTION OF THE DRAWINGS

The drawings constitute a part of this specification and include exemplary embodiments of the present invention illustrating various objects and features thereof.

DETAILED DESCRIPTION OF THE PREFERRED EMBODIMENTS

I. Introduction and Environment

As required, detailed aspects of the present invention are disclosed herein, however, it is to be understood that the disclosed aspects are merely exemplary of the invention, which may be embodied in various forms. Therefore, specific structural and functional details disclosed herein are not to be interpreted as limiting, but merely as a basis for the claims and as a representative basis for teaching one skilled in the art how to variously employ the present invention in virtually any appropriately detailed structure.

Certain terminology will be used in the following description for convenience in reference only and will not be limiting. For example, up, down, front, back, right and left refer to the invention as orientated in the view being referred to. The words, "inwardly" and "outwardly" refer to directions toward and away from, respectively, the geometric center of the aspect being described and designated parts thereof. Forwardly and rearwardly are generally in reference to the direction of travel, if appropriate. Said terminology will include the words specifically mentioned, derivatives thereof and words of similar meaning.

II. Preferred Embodiment

Figure 1:
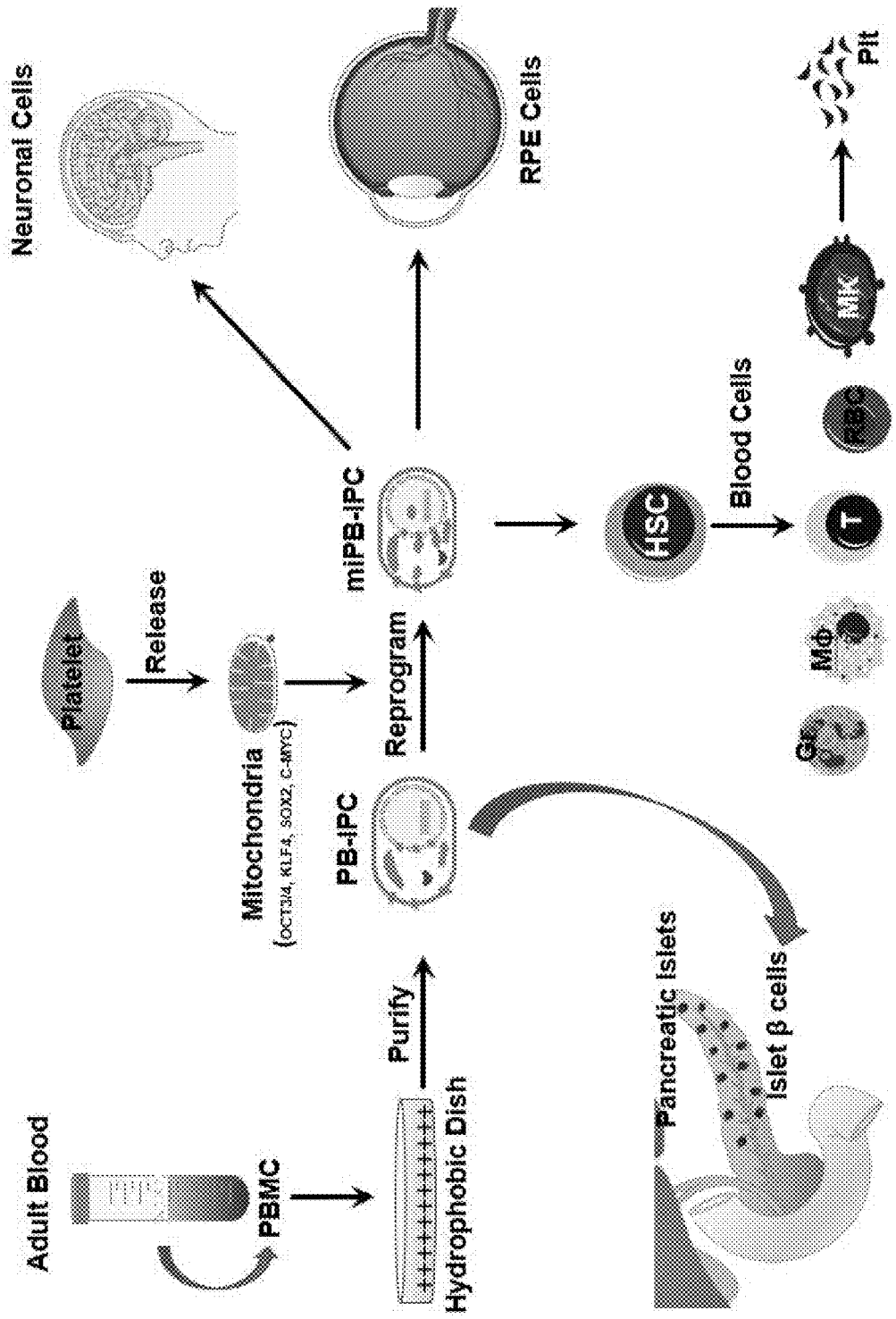
FIG. 1 is a schematic drawing illustrating a method of generating multipotent cellular differentiation by treating peripheral blood insulin-producing cells with platelet-derived mitochondria, the method embodying the present invention.

The present invention discloses a method of generating multipotent stem cells from adult human peripheral blood cells by isolating the peripheral blood insulin-producing cells (PB-IPC) and exposing them to platelet-derived mitochondria. PB-IPC, also known as "peripheral blood-stem cell (PB-SC)," have further been characterized by Zhao et al. in U.S. Pat. No. 8,835,163, which is incorporated herein by reference in its entirety. FIG. 1 shows a schematic drawing of an embodiment of a protocol of the present invention.

PB-IPC have been demonstrated to be present within human peripheral blood, displaying a unique phenotype (Lin1$^-$CD34$^-$CD45$^+$CD45RO$^+$CCR7$^+$SOX2$^+$OCT3/4$^+$ MAFA$^+$Glut2$^+$). In an exemplary embodiment, a sample of adult human peripheral blood is first obtained and centrifuged. After centrifugation, peripheral blood-derived mononuclear cells (PBMC) are then isolated from the adult peripheral blood. PB-IPC are then isolated from the PBMC via adherence to a hydrophobic surface having a positive charge. In a preferred embodiment, PB-IPC are isolated, grown, and expanded by adhering to the hydrophobic bottom of Petri dishes in chemical-defined, serum-free culture without adding any other growth factors. However, in alternative embodiments, other devices and/or media having a hydrophobic surface may be utilized to isolate PB-IPC.

In an exemplary embodiment, a sample of adult human peripheral blood platelets is obtained. In embodiments of the present invention, the platelet sample may be taken from the same peripheral blood sample as the isolated PB-IPC or alternatively from another adult human peripheral blood source. Mitochondria are then isolated from peripheral blood platelets. The platelet-derived mitochondria may be isolated as described herein or by alternative mitochondria isolation methods.

Once the PB-IPC and platelet-derived mitochondria are isolated, the platelet-derived mitochondria are applied to the isolated PB-IPC. Upon such treatment, the mitochondria are then taken in by the PB-IPC, allowing the cells to be reprogrammed and transforming PB-IPC into multipotent stem cells giving rise to three germ layer-derived cells. Upon entry into the PB-IPC, some of the applied, platelet-derived mitochondria enter the nuclei of the PB-IPC, accommodating reprogramming of the cells.

The differentiation potential of PB-IPC is markedly increased after treatment with platelet-derived mitochondria, leading to three-germ layer-derived cells. Mitochondrion-induced PB-IPC (miPB-IPC) exhibit high efficiency of differentiations toward RPE and neuronal cells in the presence of different inducers, respectively, confirming the multipotency of PB-IPC post-mitochondrial treatment. Thus, these cells offer great promise as a solution for the current bottlenecks associated with conventional stem cell transplants and have tremendous potential for patient benefit in the clinic.

PB-IPC naturally circulate in human peripheral blood, displaying islet β cell-related markers and reducing hyperglycemia with migration to pancreatic islets after transplant into the chemical streptozotocin (STZ)-induced diabetic mice. Accordingly, the present invention provides a novel approach for the generation of a large amount of autologous insulin-producing cells from patients themselves to potentially treat autoimmune disease in clinics. In comparison with the generation of insulin-producing cells from ES and iPS cells, the present technology can efficiently isolate insulin-producing cells from their own blood, without any ethical issues nor the hazards of immune rejection. Moreover, multipotent differentiation of miPB-IPC into other cell lineages provides previously unmet medical needs to circumvent those limitations not only for autoimmune disease subjects, but for the entire field of regenerative medicine. In embodiments of the present invention, miPB-IPC can differentiate into macrophage cells, neuronal cells, RPE cells, granulocyte cells, T cells, B cells, red blood cells, megakaryocyte cells, platelet cells, bone marrow cells, stromal cells, osteoblast cells, keratinocytes, hair follicle cells, gland cells, endothelial cells, corneal endothelial cells, cardiomyocytes, muscle cells, epithelial cells, hepatocytes, kidney cells, islet β cells, or other types of cells when exposed to the appropriate promoters for each.

In alternative embodiments, PBMC-derived (not platelet-derived) mitochondria are isolated and applied to PB-IPC. Upon treatment, PBMC-derived mitochondria enter the PB-IPC and also penetrate the nucleus of PB-IPC, accommodating reprogramming of the cell. In further embodiments of the present invention, mitochondria can be isolated from blood plasma, blood serum, or other parts of human blood and utilized in treating PB-IPC.

In another aspect of the present invention, PB-IPC give rise to functional CD34+ hematopoietic stem cell (HSC)-like cells after treatment with platelet-derived mitochondria, designated herein as mitochondrion-induced CD34+ HSC (miCD34+ HSC). Using autologous PB-IPC from patients as a starting material, mitochondrial treatment generates functional autologous mitochondrion-induced CD34$^+$ (miCD34$^+$) hematopoietic stem cells (HSC) on a large scale, giving rise to different blood cell lineages. Isolating PB-IPC from peripheral blood and expanding them is accomplished utilizing serum-free, culture medium having a hydrophobic surface, which avoids the painful and invasive procedures required to withdraw bone marrow. Isolated, platelet-derived mitochondria are then applied to the PB-IPC, which mitochondria enter the PB-IPC and then the nuclei of PB-IPC, allowing for reprogramming of the cells. The mitochondrion-induced PB-IPC are then further exposed to blood cell promoters for HSC-like differentiation.

Figure 2:
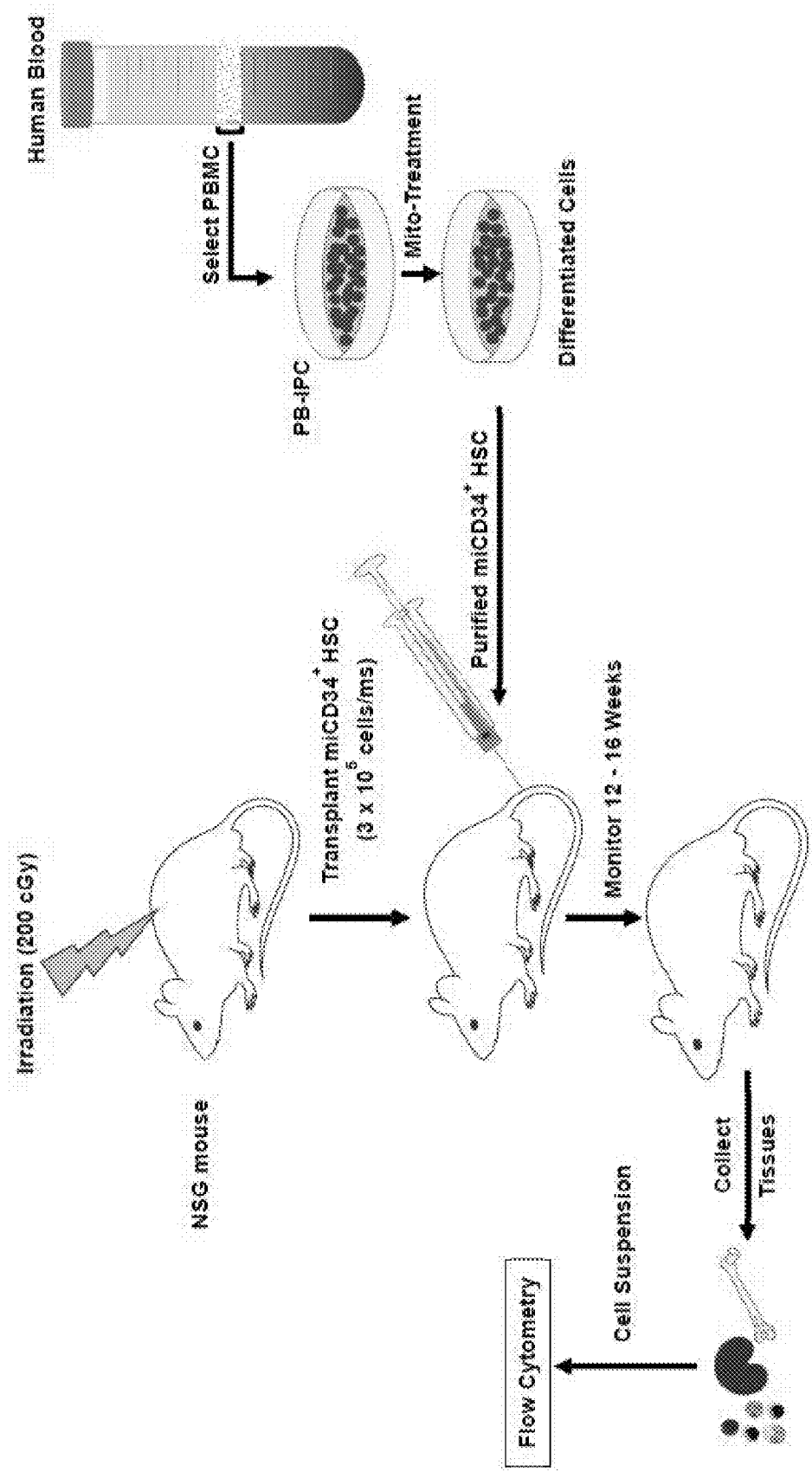
FIG. 2 is a schematic drawing illustrating a method and animal protocol embodying an aspect of the present invention for in vivo multiple differentiation of mitochondrion-induced CD34+ hematopoietic stem cell-like cells after transplantation into irradiated NSG mice.
Figure 3:
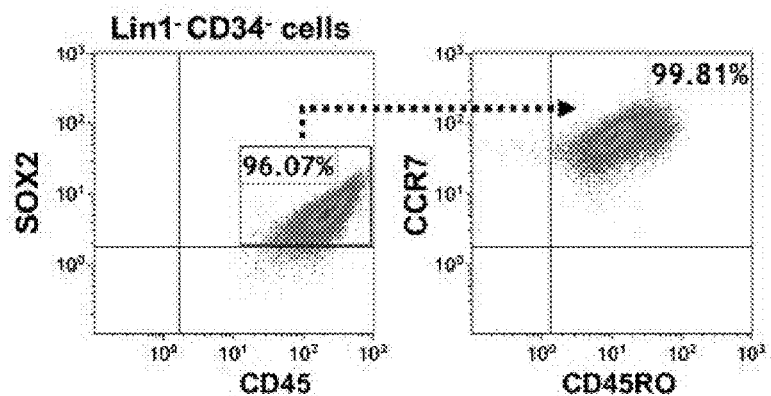
FIG. 3 shows flow cytometry graphs showing characterization of peripheral blood-derived insulin-producing cells (PB-IPC) from adult peripheral blood with islet β-cell related markers demonstrating that gated Lin1$^-$CD34$^-$ cells express CD45, SOX2, CD45RO, and CCR7 (n=8).

An animal protocol embodying the present invention is shown in FIG. 2. The miCD34+ HSC of the present invention can reconstitute multi-lineage blood cells in peripheral blood, the spleen, and bone marrow after transplantation into irradiated NSG mice at 12 weeks, including but not limited to T cells (CD3+CD4+), B cells (CD19+), monocytes/macrophages (CD14+), granulocytes (CD66b+), erythroid cells (CD235a+), and megakaryocytes/platelets (CD41b+). This demonstrates the high potential to treat hematopoietic-associated diseases with the present invention.

The capacity of self-renewal is one of the major characteristics for CD34+ HSC. The miCD34+ HSC of the present invention have exhibited a rapid multiple potential for differentiation, with a limited potential of self-renewal, meaning the mitochondrial reprogramming, differentiating the PB-IPC into CD34+ HSC-like cells with expressions of HSC-associated cell surface markers and primarily improving their multi-potency of differentiation potential, does not significantly change their capability of self-renewal.

III. Materials and Methods for Generation of Multipotent Stem Cells from miPB-IPC

A. PB-IPC Cell Culture

Human buffy coat blood units (n=42; mean age of 47.64±14.07; age range from 16 to 73 years old; 23 males and 19 females) were purchased from the New York Blood Center (New York, NY, USA). Human buffy coats were initially added to 40 mL of chemical-defined serum-free culture X-VIVO™ 15 medium (Lonza, Walkersville, MD, USA), mixed thoroughly with a 10 mL pipette, and then used for isolation of peripheral blood-derived mononuclear cells (PBMC). PBMC were harvested as previously described by Zhao et al. in "A human peripheral blood monocyte-derived subset acts as pluripotent stem cells." *Proc. Natl. Acad. Sci. U.S.A.* 2003, 100, 2426-2431, which is incorporated herein by reference in its entirety. The mononuclear cells were isolated from buffy coats blood using Ficoll-Paque™ PLUS ($\gamma$=1.007, GE Healthcare), followed by removing the red blood cells using Red Blood Cell Lysis buffer (eBioscience, San Diego, CA, USA). After three washes with saline, the whole PBMC were seeded in 150×15 mm Petri dishes (BD, Franklin Lakes, NJ, USA) at $1\times10^6$ cells/mL, 25 mL/dish in chemical-defined serum-free culture X-VIVO IM 15 medium (Lonza, Walkersville, MD, USA), without adding any other growth factors, and incubated at 37° C. in 8% $CO_2$. Seven days later, peripheral blood insulin-producing cells (PB-IPC) were growing and had expanded by adhering to the hydrophobic bottom of the Petri dishes. Consequently, PB-IPC were washed three times with saline, and all floating cells were removed. Serum-free NutriStem® hPSC XF culture medium (Corning, New York, NY, USA) was then added for continued cell culture and expansion at 37° C. in 8% $CO_2$. The expanded PB-IPC were usually applied for experiments during 7-14 days. PB-IPC were treated with 100 μg/mL platelet-derived mitochondria for 7-14 days in non-treated 24-well plates or Petri dishes with serum-free NutriStem® hPSC XF culture medium (Corning), at 37° C. and 8% $CO_2$.

B. Isolation of Mitochondria from Platelets

Mitochondria were isolated from peripheral blood (PB)-platelets using a Mitochondria Isolation kit (Thermo Scientific, Rockford, IL, USA, Prod: 89874) according to the manufacturer's recommended protocol. Adult human platelet units (n=19) were purchased from the New York Blood Center (New York, NY, USA). The concentration of mitochondria was determined by measuring protein concentration using a NanoDrop 2000 Spectrophotometer (ThermoFisher Scientific, Waltham, MA, USA). The isolated mitochondria were aliquoted and kept in a −80° C. freezer in preparation for experiments.

For mitochondrial staining with fluorescent dyes, mitochondria were labeled with MitoTracker Deep Red FM (100 nM) (Thermo Fisher Scientific, Waltham, MA, USA) at 37° C. for 15 minutes, according to the manufacturer's recommended protocol, followed by two washes with phosphate-buffered saline (PBS) at 3000 rpm×15 minutes.

C. Flow Cytometry

Flow cytometric analyses of surface and intra-cellular markers were performed. PB-IPC were washed with PBS at 2000 rpm for 5 minutes. Mitochondria were washed with PBS at 12,000 g for 10 minutes at 4° C. PB-IPC's nuclei were washed with PBS at 500 g for 5 minutes at 4° C. Samples were pre-incubated with human BD Fc Block (BD Pharmingen, San Jose, CA, USA) for 15 minutes at room temperature, and then directly aliquoted for different antibody staining. Cells were incubated with different mouse anti-human monoclonal antibodies (mAb) from Beckman Coulter (Brea, CA, USA), including FITC-conjugated anti-CD45RO, anti-CD19, anti-CD4, anti-CD8 and anti-CD42a; phycoerythrin (PE)-conjugated anti-CD34, anti-CCR7 and anti-CXCR4; phycoerythrin-Cy5.5 (PE-Cy5.5)-conjugated anti-CD19, anti-CD117 and anti-SOX2; phycoerythrin-Cy7 (PE-Cy7)-conjugated anti-CD41, anti-CD11b and anti-CD45; APC-conjugated anti-CD34, anti-CXCR4, and anti-CD4; APC-Alexa Fluor 750-conjugated, anti-CD66b and anti-CD8; pacific blue (PB)-conjugated anti-CD38; Krome Orange-conjugated anti-CD14. From BD Biosciences (San Jose, CA, USA), the investigator purchased the FITC-conjugated anti-human lineage cocktail 1 (Lin1) (CD3, CD14, CD16, CD19, CD20, CD56), Alexa Fluor 488-Sox2, Alexa Fluor 647-conjugated mouse anti-human C-peptide and insulin Abs. FITC-conjugated anti-human MAFA ab was obtained from United States Biological (Salem, MA, USA). APC-conjugated mouse anti-human CD36 mAb was purchased from BioLegend (San Diego, CA, USA). PE-conjugated anti-human GLUT2 antibody was purchased from R & D Systems (Minneapolis, MN, USA). Mouse anti SDF-1 polyclonal antibody was purchased from Abcam (Cambridge, MA, USA). The eFluor 660-conjugated rat anti-human OCT3/4 and isotype-matched IgG Abs were from Thermo Fisher Scientific (Waltham, MA, USA).

For surface staining, cells were stained for 30 minutes at room temperature and then washed with PBS at 2000 rpm for 5 minutes prior to flow analysis. Isotype-matched mouse anti-human IgG antibodies (Beckman Coulter) served as a negative control for all fluorescein-conjugated IgG mAb. For intra-cellular staining, cells were fixed and permeabilized according to the PerFix-nc kit (Beckman Coulter) manufacturer's recommended protocol. After staining, cells were collected and analyzed using a Gallios Flow Cytometer (Beckman Coulter) equipped with three lasers (488 nm blue, 638 red, and 405 violet lasers) for the concurrent reading of up to 10 colors. The final data were analyzed using the Kaluza Flow Cytometry Analysis Software (Kaluza Analysis 2.1, Beckman Coulter).

To determine insulin-producing cells in mouse peripheral blood, MIP-GFP transgenic mice were tested according to the approved animal protocol by the Institutional Animal Care and Use Committee (IACUC). MIP-GFP transgenic mice were purchased from the Jackson Laboratory (Bar Harbor, ME, USA). The strain name is B6.Cg-Tg(Ins1-EGFP)1 Hara/J (Stock Number: 006864).

D. Retinal Pigment Epithelium (RPE) Cell Differentiation of miPB-IPC

To determine mitochondrion-induced PB-IPC (miPB-IPC)'s multipotency and retinal pigment epithelium (RPE) cell differentiation (FIGS. 1 and 43), miPB-IPC were treated with combined supplements (including L-glutamine, Gentamicin sulfate-Amphotericin (GA-1000), and basic fibroblast growth factor) in the presence of retinal pigment epithelial growth media (Lonza) for 8 days, in 24-well tissue culture-treated plates, at 37° C. in 5% $CO_2$. The differentiated cells were characterized by immunocytochemistry with RPE-specific markers such as mouse anti-human mAbs RPE 65, CRALBP, and claudin-19, along with rabbit anti-tight junction protein 1 (ZO-1) polyclonal Ab (Novus Biological, Littleton, CO, USA). Human primary RPE cells were purchased from Lonza and served as a positive control. Isotype-matched IgG served as a negative control for immunostaining. For functional analysis, the phagocytosis of fluorescence latex beads (Sigma, Saint Louis, MO, USA) were performed in differentiated RPE cells. The phagocytosis-associated surface marker CD36 was examined by flow cytometry. The level of CD36 expression was quantified by mean fluorescence intensity after analyzed with Kaluza software version 2.1 (Beckman Coulter).

E. Neuronal Differentiation of miPB-IPC

To determine miPB-IPC's multipotency and their neuronal cell differentiation (FIGS. 1 and 43), miPB-IPC were treated with 100 ng/ml of neuronal growth factor (NGF, R & D Systems) plus human neuronal stem cell growth medium (iXCells Biotechnologies, San Diego, CA, USA) for 3 to 5 days, in 24-well tissue culture-treated plates, at 37° C. in 5% $CO_2$. Differentiated cells were characterized by immunocytochemistry with mouse anti-human tyrosine hydroxylase monoclonal Ab (mAb, Clone LNC1, Catalogue #MAB 318, at 1:100 dilution) and rabbit anti-Synapsin I polyclonal Ab (Catalogue #AB1543, at 1:100 dilution) (EMD Millipore, Temecula, CA, USA). The FITC-conjugated AffiniPure donkey anti-mouse 2nd Ab and Cy3-conjugated AffiniPure donkey anti-rabbit 2nd Ab were purchased from Jackson ImmunoResearch Laboratories (West Grove, PA, USA). Isotype-matched IgG served as negative control for immunostaining. After covering with Mounting Medium with DAPI (Vector Laboratories, Burlingame, CA, USA), cells were photographed with a Nikon AIR confocal microscope on a Nikon Eclipse Ti2 inverted base.

F. Colony Analysis

Figure 43:
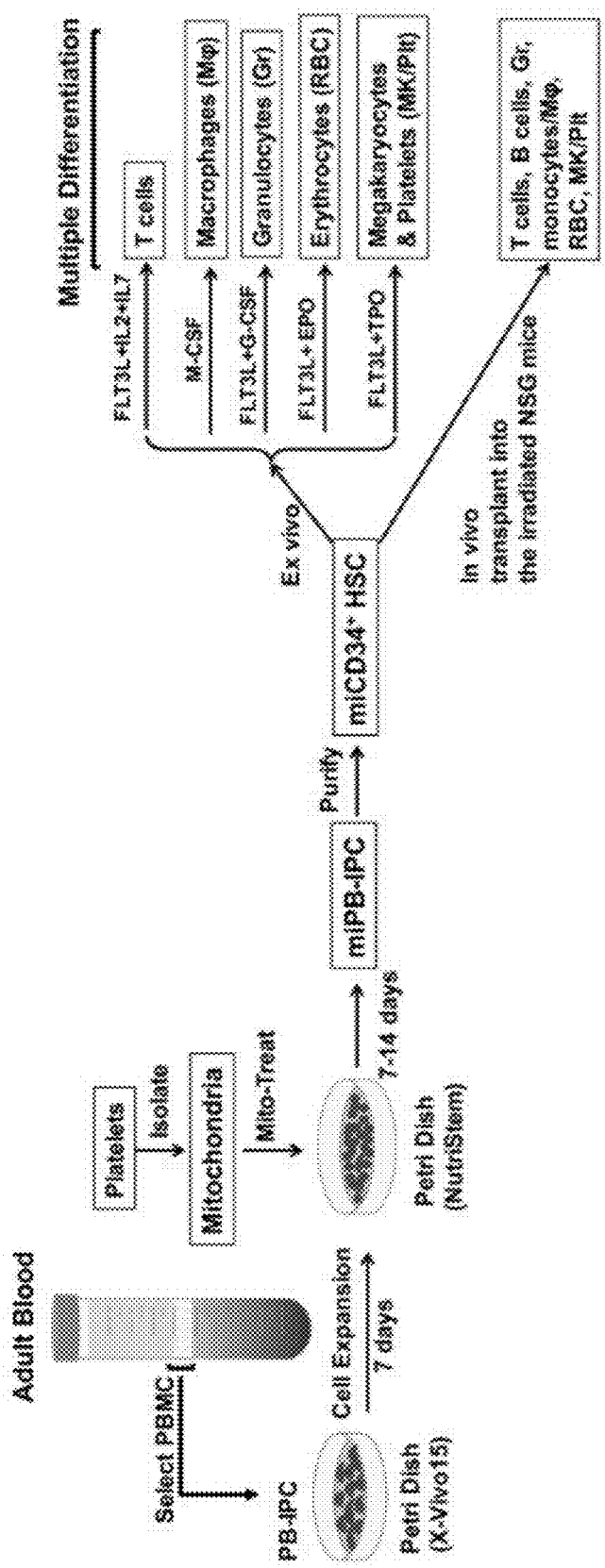
FIG. 43 is a schematic flow chart outlining a protocol of the present invention from the generation of miPB-IPCs to multipotent cellular differentiations of miPB-IPCs. The miCD34$^+$ HSCs were purified for in vitro and in vivo differentiations, respectively.

The miPB-IPC were initially cultured with serum-free NutriStem® hPSC XF culture medium (Corning) at $1×10^4$ cells/mL/well in 24-well tissue culture plates, at 37° C. in 8% $CO_2$ culture condition. After the miPB-IPC were cultured for 2 months, an individual colony was picked up under an inverted microscope by a BD Vacutainer Blood Collection Set (21G×¾"×12") attached with a 3 ml syringe (Nipro, Miami, FL, USA) and inoculated in 96-well plates. Inspection by light microscope indicated that approximately 80% of wells included a single colony. The wells with more than one colony were excluded. Each single colony (total n=21 colonies) was manually dispersed by pipetting and aliquoted to 2-8 wells (depending on the size of colonies) for induction of differentiation (FIGS. 1 and 43). The differentiation of single-colony-derived cells into different lineages were examined by using conditions as described above, respectively.

For macrophage differentiation, three colony-derived cells were treated with M-CSF plus HSC-Brew GMP Basal Medium for 2-3 days. For RPE cell differentiation, six colony-derived cells were treated with the RtEGM™ Retinal Pigment Epithelial Cell Growth Medium BulletKit™ (Lonza) for 3-5 days. For neuronal differentiation, the single colony-derived cells (total n=9 colonies) were treated with 100 ng/mL neuronal growth factor (NGF, R & D Systems) plus human neuronal stem cell growth medium (iXCells Biotechnologies, San Diego, CA, USA) in 96-well plates for 2-3 days. Their differentiations were evaluated with lineage-specific markers such as the phagocytosis of fluorescent latex beads for macrophage differentiation, RPE65 immunostaining for REP cells, and Synapsin I immunostaining for neuronal cells. Untreated colony-derived cells served as controls. Additionally, to determine their phenotype, the single-colony-derived cells (n=3 colonies) were tested by flow cytometry with leukocyte common antigen CD45, HSC marker CD34, ES cell marker SOX2, together with memory cell marker CD45RO and CCR7. Isotype-matched IgGs served as a control for flow cytometry.

To determine the multipotent differentiations of miPB-IPC, an initial colony analysis was performed with three-germ layer-associated markers, including a neuronal marker synapsin for ectoderm, an islet β cell marker insulin for endoderm, and a macrophage marker CD11b for mesoderm. Additionally, using a 3-germ layer immunocytochemistry kit (Invitrogen, Carlsbad, CA, USA), further colony analysis was performed using a Human Definitive Pancreatic Endoderm Analysis kit with additional three-germ layer-associated markers, including a neuronal marker beta III tubulin (Tuj1) for ectoderm, a liver cell marker alpha-fetoprotein (AFP) for endoderm, and smooth muscle actin (SMA) for mesoderm. For immunostaining, colonies were fixed and permeabilized in 24-well plates and followed by immunostaining as described above. IgGs served as negative controls.

G. Tumor Formation Assay

To determine the potential of tumor formation of miPB-IPC, the miPB-IPC were subcutaneously inoculated in the right flank of NSG mice ($2×10^7$ cells per mouse in 200 µL physiological saline, S.C., right lower flank, n=3 mice), according to the approved animal protocol at Hackensack Meridian Health. Injection of equal volume of physiological saline on the left lower flank served as a control. Tumor formation and body weight were monitored once a week for 12 weeks. At the end of the observations, the liver, lung, spleen, and kidney tissues of miPB-IPC-treated mice were inspected and collected for histopathological examinations on tumor formation.

H. Tracking RFP-Labeled Mitochondria in PB-IPC

To directly examine the penetration of red fluorescent protein (RFP)-labeled mitochondria into PB-IPC, RFP-labeled mitochondria were purified from an HEK-293 cell line after being labeled with CellLight™ Mitochondria-RFP BacMam 2.0 (Thermo Fisher Scientific, Waltham, MA, USA), according to manufacturer's recommended protocol. PB-IPC were initially plated in 12 mm Nunc Glass Base Dish (Thermo Fisher Scientific) in NutriStem® hPSC XF culture medium. After attaching for one hour, PB-IPC were treated with the purified RFP-labeled mitochondria in X-VIVO™ 15 medium (Lonza). After the treatment for 4 hours, the treated PB-IPC were photographed by using confocal microscopy. Hoechst 33,342 were applied to stain the nucleus of viable cells.

I. Transmission Electron Microscopy (TEM)

To determine the penetration of mitochondria into nuclei, PB-IPC were treated with 100 µg/mL of platelet-derived mitochondria for 12 hours, at 37° C. in 8% $CO_2$. Consequently, the mitochondrion-treated and untreated PB-IPC were collected at 500 g×5 min and fixed with 2.5% glutaraldehyde/4% paraformaldehyde in 0.1 M Cacodylate buffer for transmission electron microscope (Philips CM12 electron microscope with AMT-XR11 digital camera) analysis. Alternatively, the purified viable nuclei were labeled with Hoechst 33,342 and were incubated with MitoTracker Deep Red-labeled mitochondria. Their interactions were directly observed and photographed under confocal microscope.

J. Blocking Experiment with CXCR4 Receptor Antagonist AMD 3100

To determine whether the action of SDF-1/CXCR4 contributed to the penetration of mitochondria into nuclei, a blocking experiment with CXCR4 receptor antagonist AMD3100 was performed. The purified PB-IPC's nuclei were treated with MitoTracker Deep Red-labeled purified mitochondria in the presence or absence of AMD 3100 (30 µM). The equal concentration of solvent DMSO served as a control. After 4 hours of the treatment, nuclei were washed twice with PBS and prepared for flow cytometry.

K. Quantitative Real Time PCR

To clarify the interaction of mitochondria and nuclei, PB-IPCs' nuclei were isolated using Nuclei isolation kit (Sigma) according to the manufacturer's recommended protocol. PB-IPCs' nuclei were treated with 100 μg/mL platelet-derived mitochondria for 4 hours, at 37° C. in 8% $CO_2$. Consequently, the mitochondrion-treated and untreated nuclei were collected at 500 g×5 minutes and fixed with 2.5% glutaraldehyde/4% paraformaldehyde in 0.1 M cacodylate buffer for electronic microscope. Additionally, $RT^2$ Profiler real time PCR Array was applied to study the directly genetic and epigenetic modulations of mitochondria by using the Human Epigenetic Chromatin Modification Enzymes kit (96-well format, Qiagen, Valencia, CA, USA). $RT^2$ Profiler real time PCR Array was used according to the manufacturer's instructions. The data were analyzed using PrimePCR array analysis software (Bio-Rad, Hercules, CA, USA).

To detect the expression of human islet β-related gene markers by quantitative real time PCR, PB-IPC were isolated from culture vessels after attachment at different time points such as 6, 12, 24, 48, and 72 hours. Total RNAs from each sample were extracted using a Qiagen kit (Valencia, CA, USA). First-strand cDNAs were synthesized from total RNA using an iScript gDNA Clear cDNA Synthesis Kit according to the manufacturer's instructions (Bio-Rad, Hercules, CA, USA). Real-time PCR was performed on each sample in triplicate using the StepOnePlus Real-Time PCR System (Applied Biosystems, CA, USA) under the following conditions: 95° C. for 10 minutes, then 40 cycles of 95° C. for 15 seconds, and 60° C. for 60 seconds, using the validated gene-specific PCR Primer sets for each gene including pancreatic islet cell-related markers including insulin (Bio-Rad Laboratories, Hercules, CA, USA), MAFA, NKX6.1, and PDX-1 (Qiagen, Valencia, CA, USA). The expression level of each gene was determined relative to β-actin as an internal control. To confirm gene expression, real time PCR products were examined with 1.5% agarose gel electrophoresis.

L. RNA-Sequencing (RNA-seq)

RNA sequencing (RNA-seq) analysis was performed between the mitochondrion-treated and untreated PB-IPC in four preparations. Total RNAs from each sample were extracted using a Qiagen kit (Valencia, CA, USA) and shipped to Genewiz (South Plainfield, NJ, USA) in dry ice for standard RNA sequencing and profiling gene expression by using Illumina NovaSeq™ 6000 Sequencing System (Genewiz, South Plainfield, NJ, USA), with 2×150 bp configuration, single index, per lane.

M. Statistics

Statistical analyses of data were performed by the two-tailed paired Student's t-test to determine statistical significance between untreated and treated groups. Values were given as mean±SD (standard deviation).

IV. Materials and Methods for Generation of Hematopoietic-Like Stem Cells from miPB-IPC A. PB-IPC Cell Culture Human buffy coat blood units (n=51; mean age of 48.97±14.11; age range from 18 to 72 years old; 24 males and 27 females) were purchased from the New York Blood Center (New York, NY, USA). Human buffy coats were initially added to 40 mL of chemical-defined, serum-free culture X-VIVO™ 15 medium (Lonza, Walkersville, MD, USA), mixed thoroughly with a 10 mL pipette, and then used for isolation of peripheral-blood-derived mononuclear cells (PBMCs). PBMCs were then harvested. The mononuclear cells were isolated from buffy coat blood using Ficoll-Paque™ PLUS (γ=1.007, GE Healthcare, Chicago, IL, USA), followed by removing red blood cells using a red blood cell lysis buffer (eBioscience, San Diego, CA, USA). After three washes with saline, the whole PBMCs were seeded in 150×15 mm Petri dishes (BD Falcon, NC, USA) at 1×10⁶ cells/mL, 25 mL/dish in chemical-defined, serum-free culture X-VIVO™ 15 medium (Lonza, Walkersville, MD, USA) without any other added growth factors, and incubated at 37° C. in 8% $CO_2$. Seven days later, PB-IPCs were growing and expanded by adhering to the hydrophobic bottom of Petri dishes. Subsequently, PB-IPCs were washed three times with saline, and all floating cells were removed. Next, serum-free NutriStem® hPSC XF culture medium (Corning) was added to continue the cell culture and expansion at 37° C. in 8% $CO_2$. The expanded PB-IPCs were utilized for experiments within 7-14 days.

B. Isolation of Mitochondria from Platelets

Mitochondria were isolated from peripheral blood (PB) platelets using a Mitochondria Isolation kit (Thermo Scientific, Rockford, IL, USA, Prod: 89874) according to the manufacturer's recommended protocol. Adult human platelet units (n=16; mean age of 30.81±8.64; age range from 16 to 40 years old; 9 males and 7 females) were purchased from the New York Blood Center (New York, NY, USA). The concentration of mitochondria was determined by the measurement of protein concentration using a NanoDrop 2000 Spectrophotometer (ThermoFisher Scientific, Waltham, MA, USA). The isolated mitochondria were aliquoted and kept in a −80° C. freezer for experiments.

For mitochondrial staining with fluorescent dyes, mitochondria were labeled with MitoTracker Deep Red FM (100 nM) (Thermo Fisher Scientific, Waltham, MA, USA) at 37° C. for 15 minutes according to the manufacturer's recommended protocol, followed by two washes with PBS at 3000 rpm×15 minutes.

C. In Vitro Differentiation of PB-IPCs into miCD34+ HSCs

PB-IPCs were treated with 100 μg/mL platelet-derived mitochondria for 7-14 days in non-treated 24-well plates or Petri dishes with serum-free NutriStem® hPSC XF culture medium (Corning, New York, NY, USA), at 37° C. and 8% $CO_2$. According to our current protocol, mitochondrion-induced CD34+ hematopoietic-like stem cells (miCD34⁺ HSCs) were purified from mitochondria-treated PB-IPCs by immunomagnetic sorting with Miltenyi Biotech CD34 MicroBead Kit (Miltenyi Biotech, Gladbach, Germany, catalog #130-097-047) according to the manufacturer's instructions. The differentiation of miCD34⁺ HSCs was characterized by flow cytometry.

D. Flow Cytometry

Flow cytometric analyses of surface and intracellular markers were performed. PB-IPCs were washed with PBS at 2000 rpm for 5 minutes. Mitochondria were washed with PBS at 12,000 g for 10 minutes at 4° C. Samples were pre-incubated with human BD Fc Block (BD Pharmingen, Franklin Lakes, NJ, USA) for 15 minutes at room temperature and then directly aliquoted for different antibody staining. Cells were incubated with different mouse anti-human monoclonal antibodies (mAb). For surface staining, cells were stained for 30 minutes at room temperature and then washed with PBS at 2000 rpm for 5 minutes prior to flow analysis. Isotype-matched mouse anti-human IgG antibodies (Beckman Coulter, Brea, CA, USA) served as a negative control for all fluorescein-conjugated IgG mAb. SYTO™60 (Thermo Fisher, Waltham, MA, USA) was combined with CD235a (GLY-A) staining to determine the nucleated erythroid cells. Staining with propidium iodide (PI) (BD Biosciences, San Jose, CA, USA) was used to exclude dead cells during flow cytometry analysis. For intracellular staining, cells were fixed and permeabilized according to PerFix-nc kit (Beckman Coulter) manufacturer's recommended protocol. After staining, cells were collected and analyzed using a Gallios Flow Cytometer (Beckman Coulter, Brea, CA, USA) equipped with three lasers (488 nm blue, 638 red, and 405 violet lasers) for concurrent reading of up to 10 colors. The final data were analyzed using the Kaluza Flow Cytometry Analysis software version 2.1 (Beckman Coulter).

Cells were incubated with different mouse anti-human monoclonal antibodies (mAb) from Beckman Coulter (Brea, CA, USA), including FITC-conjugated anti-CD45RA, anti-IFNγ, anti-CD4, anti-CD235a, anti-CD8 and anti-CD42a; phycoerythrin (PE)-conjugated anti-CD34; PE-Texas Red-conjugated CD3; phycoerythrin-Cy5 (PE-Cy5)-conjugated anti-CD90; phycoerythrin-Cy5.5 (PE-Cy5.5)-conjugated anti-CD19; phycoerythrin-Cy7 (PE-Cy7)-conjugated anti-CD49f, anti-CD11b and anti-CD45; APC-conjugated anti-CD4; APC-Alexa Fluor 700-conjugated anti-CD71; APC-Alexa Fluor 750-conjugated anti-CD7, anti-CD66b and anti-CD8; Pacific blue (PB)-conjugated anti-CD38; Krome Orange-conjugated anti-CD14 and anti-135 (FLT3)-BV510. From BD Biosciences (San Jose, CA, USA), the investigators purchased the AlexaFluor-488-conjugated anti-human Cytochrome C; FITC-conjugated anti-CD90 (THY1) and anti-CD11C; BV 510-conjugated anti-CD45, PE-conjugated anti-IL4, anti-IL5, anti-BAH1, anti-IL12; PE-CF594-conjugated anti-CD10, BV421-conjugated anti-CD209 and PE-conjugated anti-mouse CD45.1. Antibodies were purchased from Biolegend (San Diego, CA, USA) including the FITC-conjugated anti-human Hsp60, anti-human TCRαβ, anti-human Notch 1 and anti-human Notch 2; PE-conjugated anti-human Notch 3, anti-human Dll1, anti-human Dll4 and anti-human Jagged2; APC conjugated anti-human Notch 4; phycoerythrin-Cy7 (PE-Cy7)-conjugated anti-TCRγδ and Pacific blue (PB)-conjugated anti-CD3. FITC-conjugated anti-human Jagged1 and PE-conjugated anti-human Dll3 mAbs were purchased from R&D Systems (Minneapolis, MN, USA). Hemoglobinβ/γ/δ (H-76) rabbit polyclonal antibody, AlexaFluor-546-conjugated Calnexin and AlexaFluor-647-conjugated GM130 were purchased from Santa Cruz Biotechnology (Dallas, TX, USA). SYTOTM60 was purchased from Thermo Fisher (Waltham, MA, USA).

E. Multiple Differentiations of miCD34+ HSCs

Initially, miCD34+ HSCs were purified from miPB-IPCs by using a CD34 MicroBead Kit, human-lyophilized (Miltenyi Biotec, Gladbach, Germany) through the auto MACS Pro Separator (Miltenyi Biotec, Gladbach, Germany) according to the manufacturer's recommended protocol. The purified miCD34+ HSCs were treated with different inducers for cellular differentiations.

To test T-cell differentiation, the purified miCD34+ HSCs ($1 \times 10^5$ cells/mL) were planted in 24-well non-treated plates in the presence of HSC-Brew GMP Basal Medium (Miltenyi Biotec, Gladbach, Germany) with the addition of cytokines 25 ng/ml hFlt3L and 25 ng/mL rhIL-7 (R&D Systems, Minneapolis, MN, USA), at 37° C. in 5% $CO_2$. After treatment for 3-7 days, cells were photographed and analyzed by confocal microscopy and flow cytometry using different T-cell markers such as CD3, CD4, CD8, TCR α/β, CD38, Th1 cytokines (IL-4 and IL-5) and Th2 cytokines (IFN-γ and IL-12). Untreated miCD34+ HSCs served as negative controls. T cells from healthy donors served as positive controls. For combined immunocytochemistry, the differentiated cells were fixed in 24-well plates with 4% paraformaldehyde for 20 minutes and permeabilized with 0.5% triton X-100 (Sigma, Saint Louis, MO, USA) for 5 minutes, blocking non-specific binding with 2.5% horse serum, and followed by immunostaining with FITC-conjugated mouse anti-human CD4 and CD8 (Beckman Coulter, Brea, CA, USA). After covering with mounting medium with DAPI (Vector Laboratories, Burlingame, CA, USA), cells were photographed with a Nikon AIR confocal microscope on a Nikon Eclipse Ti2 inverted base, using NIS Elements Version 4.60 software.

For differentiation of miCD34+ HSCs to macrophages, purified miCD34+ HSCs ($1 \times 10^5$ cells/mL) were treated with 50 ng/ml M-CSF (Sigma, St. Louis, MO, USA) in 24-well non-treated plates in the presence of HSC-Brew GMP Basal Medium, at 37° C. in 5% $CO_2$. After treatment for 2-3 days, cells were analyzed with phagocytosis and by flow cytometry with macrophage marker CD11b (Beckman Coulter, Brea, CA, USA) and CD209 (BD Biosciences, San Jose, CA, USA). Untreated miCD34+ HSCs served as negative controls. To detect the function of differentiated macrophages, fluorescent latex beads (Sigma, Saint Louis, MO, USA) were added to M-CSF-treated and untreated miCD34+ HSC cultures. After 4 hours of incubation with latex beads, cells were washed three times with PBS. Phagocytosis was viewed and evaluated under microscopy. The positive cells had a minimum of five beads per cell.

To differentiate miCD34+ HSCs into granulocytes, purified miCD34+ HSCs ($1 \times 10^5$ cells/mL) were treated with 25 ng/mL hFlt3L plus 100 ng/mL G-CSF (R&D Systems) in the presence of HSC-Brew GMP Basal Medium, in 24-well non-treated plates, at 37° C. in 5% $CO_2$. After the treatment for 3-5 days, cells were photographed and analyzed by flow cytometry with granulocyte marker CD66b and staining with Wright-Giemsa (Sigma, Saint Louis, MO, USA) according to the manufacturer's instructions. Untreated miCD34+ HSCs served as negative controls. PBMCs from healthy donors served as positive controls.

To differentiate miCD34+ HSCs into RBCs, purified miCD34+ HSCs ($1 \times 10^5$ cells/mL) were initially treated with 25 ng/ml hFlt3L plus 3 units/mL EPO (R&D Systems, Minneapolis, MN, USA) in the presence of HSC-Brew GMP Basal Medium, in 24-well non-treated plates, at 37° C. in 5% $CO_2$. After treatment for 5 days, cells were re-treated with 3 units/mL EPO for an additional 3-7 days. Subsequently, cells were photographed and analyzed by flow cytometry with erythrocyte markers CD235a and hemoglobin. Untreated miCD34+ HSCs served as negative controls. For intracellular flow cytometry, all floating cells were collected and centrifuged at 2700 g×15 minutes. First, after blocking non-specific binding with Fc Blocker (BD Biosciences, San Jose, CA, USA), cells were fixed and permeabilized using a PerFix-nc kit (Beckman Coulter, Brea, CA, USA) according to the manufacturer's recommended protocol. Second, cells were incubated with rabbit anti-human hemoglobinβ/γ/δ polyclonal antibody (Santa Cruze, Dallas, TX, USA) at 1:100 dilution at room temperature for 30 minutes and then washed with PBS at 2700 g×15 minutes. Next, cells were labeled with Cy5-conjugated AffiniPure donkey anti-rabbit 2nd Ab (Jackson ImmunoResearch Laboratories, West Grove, PA, USA), in combination with staining with mouse anti-human CD235a-FITC (Beckman Coulter, Brea, CA, USA) and CD45-PE-CY7 mAbs for 30 minutes, and followed by flow cytometry analysis.

To differentiate miCD34+ HSCs into megakaryocytes and platelets, purified miCD34+ HSCs ($1 \times 10^5$ cells/mL) were initially treated with 25 ng/ml hFlt3L+100 ng/ml TPO (R&D Systems, Minneapolis, MN, USA) in the presence of HSC-Brew GMP Basal Medium, in 24-well non-treated plates, at 37° C. in 5% $CO_2$. After this treatment for 3-7 days, cells were photographed and collected for flow cytometry with MK/platelet marker CD42a (Beckman Coulter, Brea, CA, USA). Untreated miCD34$^+$ HSCs served as negative controls. For analysis of polyploidization, viable TPO-treated miCD34$^+$ cells were first stained with CD42a mAb and Hoechst 33342 (Sigma, Saint Louis, MO, USA) and photographed under a confocal microscope. Secondly, using healthy donor-derived matured T cells (1N) and platelets (ON) as controls, the polyploidy of differentiated CD42a$^+$ MKs was analyzed by flow cytometry after staining with propidium iodide (PI) (Abcam, Cambridge, MA, USA) according to the manufacturer's recommended protocol.

To morphologically determine the differentiation of miCD34$^+$ HSCs to granulocytes, RBCs, and megakaryocytes/platelets, Wright-Giemsa staining was performed on the treated and untreated cells, which were then observed and photographed under an inverted Nikon ECLIPSE Ti2 microscope.

For a DAPT-blocking experiment, PB-IPCs were treated with 100 μg/mL mitochondria plus 10 μM DAPT (Sigma, Saint Louis, MO, USA, Catalog #D5942) for 7-14 days in non-tissue, culture-treated 24-well plates or Petri dishes with serum-free NutriStem® hPSC XF culture medium (Corning, New York, NY, USA), at 37° C. and 8% $CO_2$. Subsequently, both treated and untreated PB-IPC were collected to examine the expression of CD34 by flow cytometry.

F. Animal Study and Engraftment of miCD34+ HSCs into Irradiated NSG Mice

All animal experiments were performed according to approval of the Institutional Animal Care and Use Committee of Hackensack Meridian Health. To demonstrate the multipotent features of miCD34$^+$ HSCs, purified miCD34$^+$ HSCs were transplanted into irradiated NOD/Lt-scid/IL2R$\gamma^{null}$ (NSG) mice. NSG mice were purchased from Jackson Laboratories (Bar Harbor, ME, USA) and were bred and maintained under pathogen-free conditions at the animal facility of the Center for Discovery and Innovation.

To determine the repopulating potential of miCD34$^+$ HSCs, NSG mice, aged 12-16 weeks, were irradiated with 200 cGy using an RS-2000 irradiator (Rad Source Technologies, Suwanee, GA, USA). The miCD34$^+$ HSCs were transplanted into irradiated NSG mice at $3 \times 10^5$ cells/mouse via the tail vein (in 200 μL saline, i.v., n=10 mice) 24 hours after irradiation, according to a protocol approved by the Animal Care and Use Committee (ACC) of the Hackensack Meridian Health. Only physiological saline injection (200 μL) served as a control (n=6 mice). After transplantation, mice were monitored twice a week for 16 weeks. To examine the differentiation of miCD34$^+$ HSCs, mice were sacrificed at 12 or 16 weeks post-transplantation to collect samples of peripheral blood, the spleen, and bone marrow for flow cytometry analysis. To determine the multilineage differentiation of miCD34$^+$ HSCs after transplantation into irradiated NSG mice, only the viable cells from different samples were gated for analysis after excluding propidium iodide (PI)-positive dead cells. The gated human leukocyte common antigen CD45-positive and mouse CD45.1-negative viable cells were further analyzed for characterization with different human blood cell lineage-specific surface markers such as CD3 and CD4 for T cells; CD19 for B cells; CD41b for megakaryocytes/platelets; CD14, CD11b, and CD11c for monocytes/macrophages; CD66b for granulocytes; and CD235a for erythroid cells. SYTO60 was utilized to stain CD235a$^+$ nucleated erythroid cells. To determine T-cell populations and remove CD4$^+$ monocytes, anti-CD3 Ab was employed to gate out CD4$^+$ monocytes, in addition to the consideration of cell size difference. Isotype-matched IgGs served as controls for flow cytometry.

G. Statistics

Statistical analyses were performed with GraphPad Prism 8 (version 8.0.1) software. The normality test of samples was evaluated using the Shapiro-Wilk test. Statistical analyses of data were performed using the two-tailed paired Student's t-test to determine statistical significance between untreated and treated groups. The Mann-Whitney U test was utilized for non-parametric data. Values are given as mean±SD (standard deviation). Statistical significance was defined as p<0.05, two sided.

It is to be understood that while certain embodiments and/or aspects of the invention have been shown and described, the invention is not limited thereto and encompasses various other embodiments and aspects.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art of the invention may develop equivalent means or reactants without the exercise of inventive capacity and without departing from the scope of the invention.

Example 1

Figure 4:
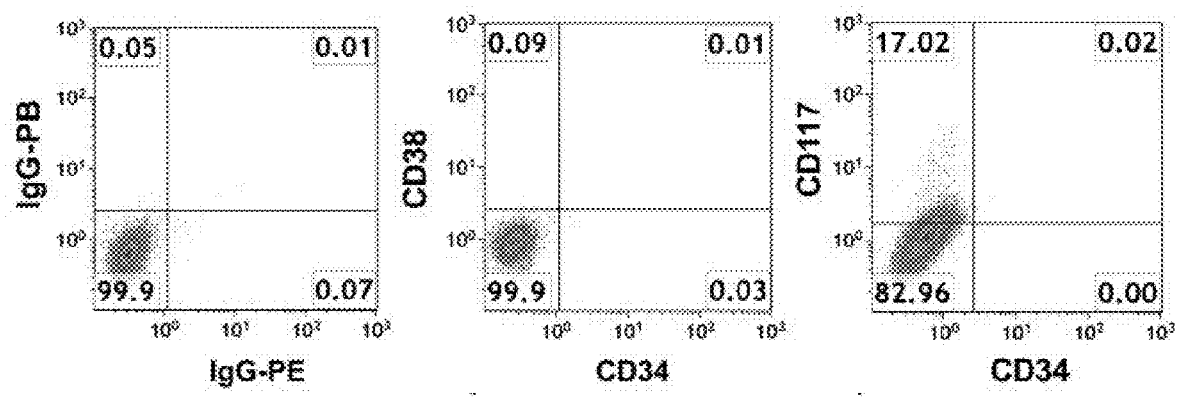
FIG. 4 shows flow cytometry graphs showing the phenotype of PB-IPC, with low expression of CD117, but no expression of CD4, CD8, CD19, CD34, CD38, CD41, CD42a, and CD66b. Isotype-matched IgGs served as controls (n=8).
Figure 5:
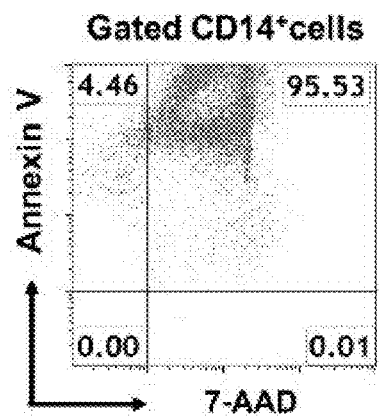
FIG. 5 illustrates apoptosis (Annexin V$^+$) and necrosis (7-AAD$^+$) of blood monocytes after 24-hour culture in non-tissue culture-treated Petri dishes (n=5).
Figure 6:
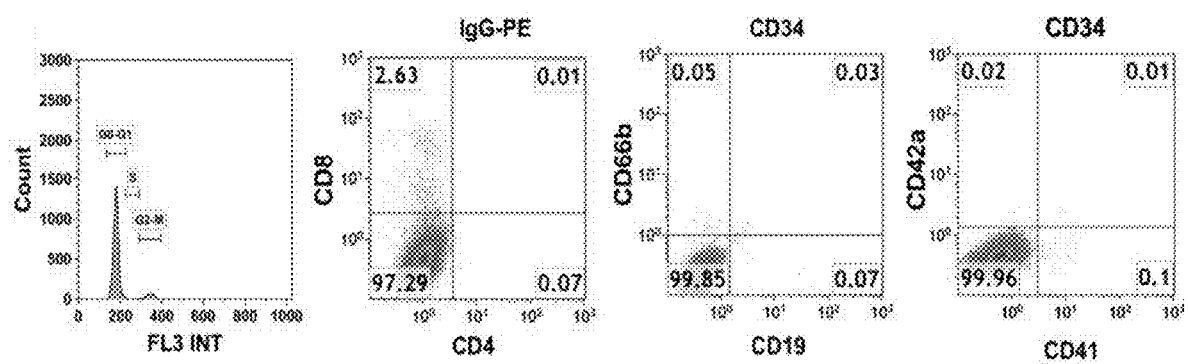
FIG. 6 shows analysis of cell cycles in the freshly-isolated PB-IPC after overnight attachment by flow cytometry with propidium iodide (PI) staining (n=5).

Adult Peripheral Blood-Derived PB-IPC Display Human Islet β Cell-Specific Markers FIGS. 3-10 illustrate the characterization of peripheral blood-derived insulin-producing cells (PB-IPC) from adult peripheral blood with islet β-cell-related markers. To characterize the specific marker of PB-IPC, PB-IPC were purified from adult peripheral blood by virtue of their ability to attach to the hydrophobic plastic surface of Petri dishes in serum-free culture medium. Flow cytometry demonstrated that PB-IPC displayed the phenotype of Lin$^-$CD34$^-$CD45$^+$ SOX2$^+$CD45 RO$^+$CCR7$^+$ (FIG. 3), including the expression of leukocyte common antigen CD45, memory cell markers CD45RO and CCR7, and embryonic stem (ES) cell marker SOX2, with low expression of CD117. In contrast, PB-IPC were negative for HSC markers CD34 and CD38; T cell markers CD3, CD4, and CD8; B cell marker CD19; granulocyte marker CD66b; and MK/platelet markers CD41 and CD42a (FIG. 4). CD14$^+$ monocytes/macrophages which could not adhere to the hydrophobic surface of culture vessels underwent apoptosis and/or necrosis within 24 hours of culture (FIG. 5). Additionally, cell cycles of the freshly-isolated PB-IPC were analyzed after overnight attachment by flow cytometry with propidium iodide (PI) staining. The data demonstrated that there was 0.9±0.5% of freshly-isolated PB-IPC distributed in the S phase, with 92.94±2.75% in $G_0/G_1$ phases and 6.68±2.2% in $G_2/M$ phases (FIG. 6). This indicates the limited potential of cellular proliferation for freshly-isolated PB-IPC. Thus, PB-IPC display a unique phenotype and are different from mesenchymal stem cells (MSC) and monocyte-derived stem cells (designated fibroblast-like macrophages, f-Mφ).

Figure 7:
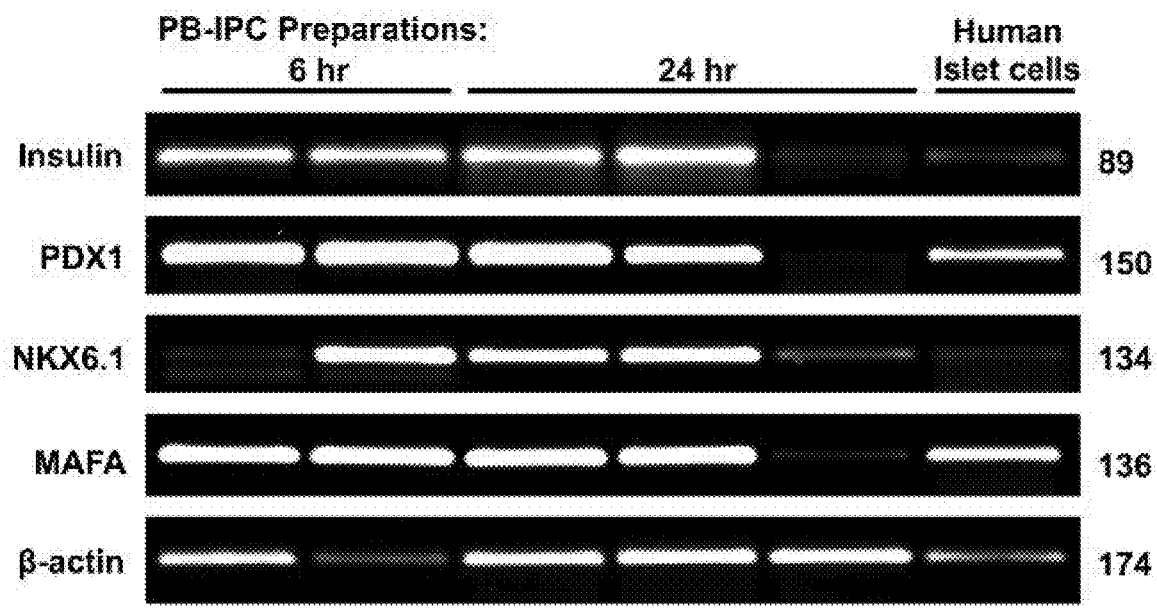
FIG. 7 shows real time PCR analysis of pancreatic islet β-cell-related markers in PB-IPC isolated from healthy donors (n=5). Freshly isolated human islets served as positive controls.
Figure 8:
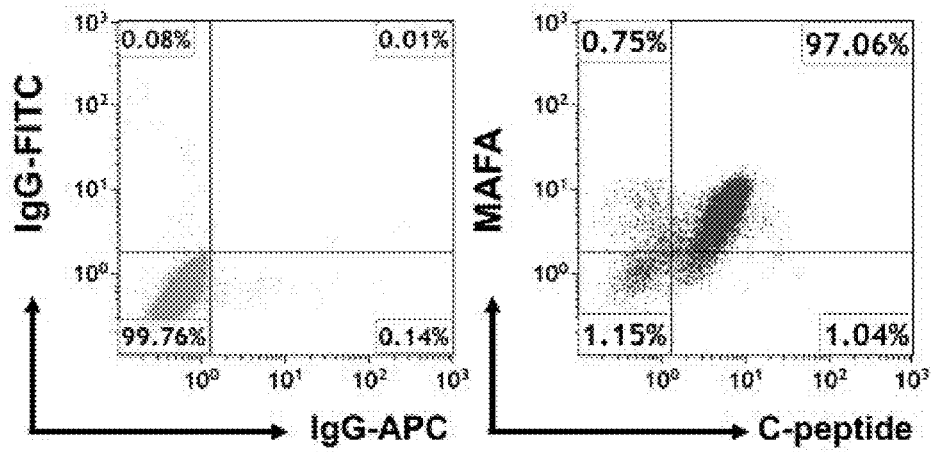
FIG. 8 shows flow cytometry for islet β-cell-related transcription factor MAFA and an insulin by-product C-peptide by double immunostaining (n=5).
Figure 9:
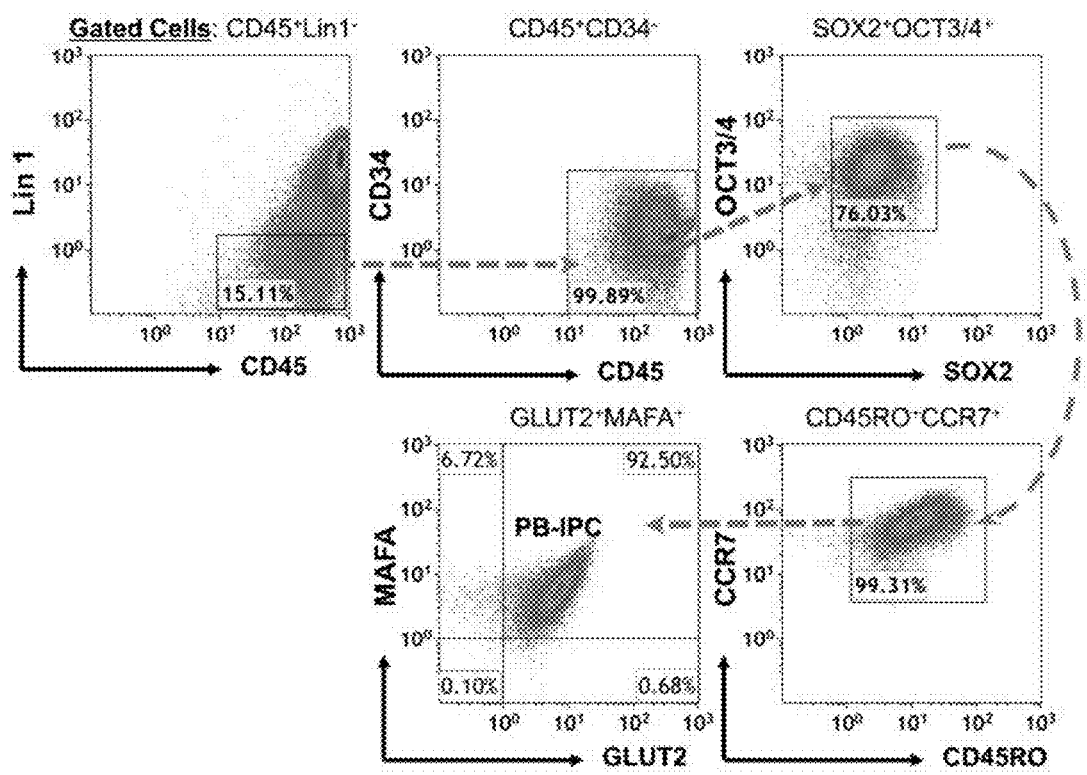
FIG. 9 shows flow cytometry for determining PB-IPC's phenotype after overnight attachment. Representative data shown from four preparations.
Figure 10:
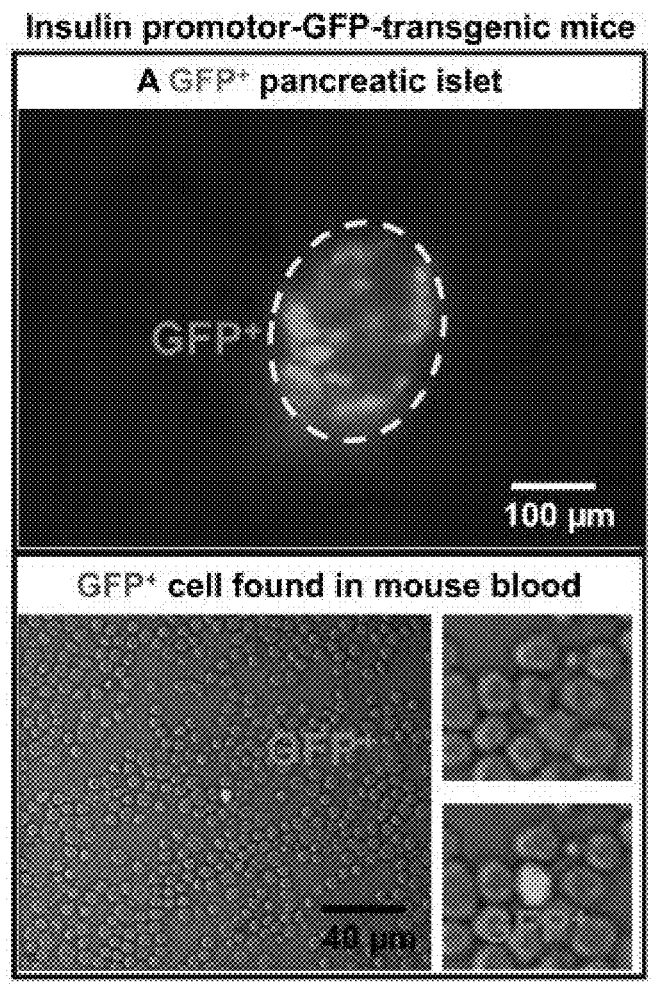
FIG. 10 is fluorescence microscopy imaging showing a GFP+ cell among PBMC of an insulin promotor 1-GFP-transgenic mouse (n=3). A GFP-positive mouse islet served as positive control.
Figure 11:
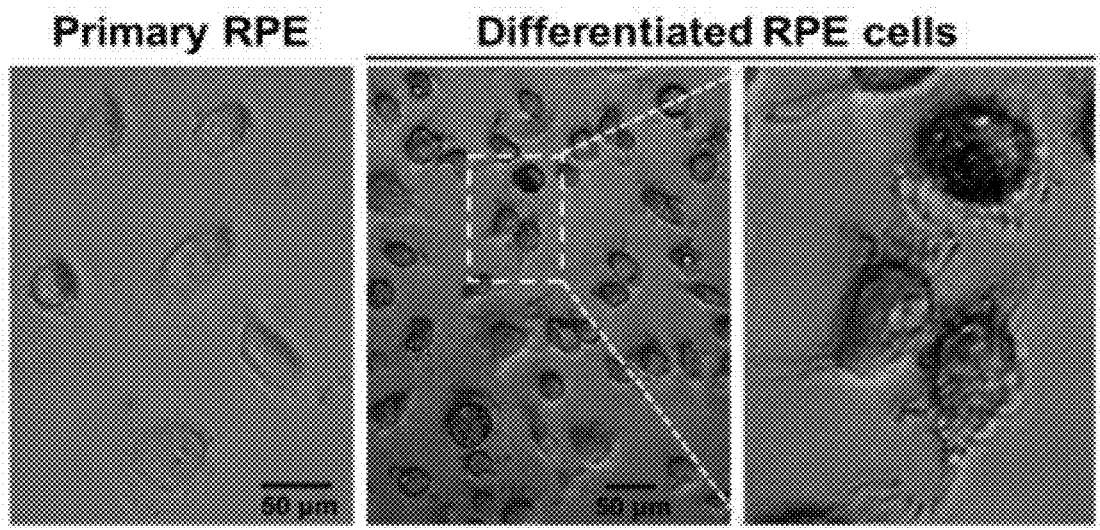
FIG. 11 is phase contrast imaging showing differentiation of miPB-IPC into RPE cells with cellular pigmentation and processes at varied lengths (n=5).

Next, insulin production of PB-IPC was analyzed. Using human islet cells as a positive control group, real time PCR data revealed that PB-IPC expressed human islet β cell-specific markers including insulin and transcription factor (PDX-1, NKX6.1, and MAFA) mRNAs (FIG. 7). Kinetic analysis demonstrated that these gene markers were stable in most PB-IPC samples within 24-hour ex vivo cultures of PB-IPC in the presence of serum-free X-VIVO™ 15 media, while some markers were disappeared or down-regulated, due to the potential different health statuses of blood donors. Flow cytometry further confirmed the double-positive cells with expressions of MAFA and C-peptide (a by-product of insulin) at protein levels (FIG. 8). Since MAFA is the only islet β cell-specific activator responsible for insulin expression and glucose transporter 2 (GLUT2) is a surface marker for human islet β cells, we further analyzed the percentage of PB-IPC in human peripheral blood mononuclear cells (PBMC) by using MAFA plus GLUT2 in combination with the above PB-IPC markers and an additional marker for an ES cell-associated transcription factor octamer-binding protein 3/4 (OCT3/4) and SRY-box containing gene 2 (SOX2). FITC-conjugated anti-human lineage cocktail 1 (Lin1) (CD3, CD14, CD16, CD19, CD20, CD56) was applied to eliminate the known cell lineages such as T cells, monocytes/macrophages, granulocytes, B cells, and natural killer (NK) cells. Anti-human leukocyte common antigen CD45 mAb was used to remove red blood cells (RBC) and platelets' contamination during data analysis. MAFA (transcription factor) and GLUT2 (β cell surface marker) were utilized to determine the islet β cell-associated phenotype in PB-IPC. Flow cytometry analysis indicated that there was 0.0045±0.004 of $Lin1^-CD34^-CD45^+CD45RO^+CCR7^+SOX2^+OCT3/4^+MAFA^+Glut2^+$ PB-IPC cells in freshly Ficoll Paque-isolated human PBMC. After overnight (12 hours) attachment selection, PB-IPC can be isolated from PBMC and display the same phenotype, with expression of $Lin1^-CD34^- CD45^+CD45RO^+CCR7^+SOX2^+OCT3/4^+ MAFA^+Glut2^+$ (FIG. 9). Additionally, GFP-positive insulin-producing cells were also found to be in the peripheral blood of insulin promotor-green fluorescence protein (GFP)-transgenic mice (The strain name: B6.Cg-Tg(Ins1-EGFP)1Hara/J, stock No: 006864) (FIG. 10). Therefore, these data established the existence of PB-IPC in peripheral blood that can be isolated by the current approach.

Example 2

Ex Vivo Differentiation of Mitochondrion-Induced PB-IPC (miPB-IPC) into Retinal Pigment Epithelium (RPE) Cells Platelets are enucleate cells without human genomic DNA. Apheresis platelets were obtained from New York Blood Center, with high purity (>99% of $CD41^+CD42^+$ platelets) for the following experimentation. The purity of isolated mitochondria was ≥90%.

Figure 12:
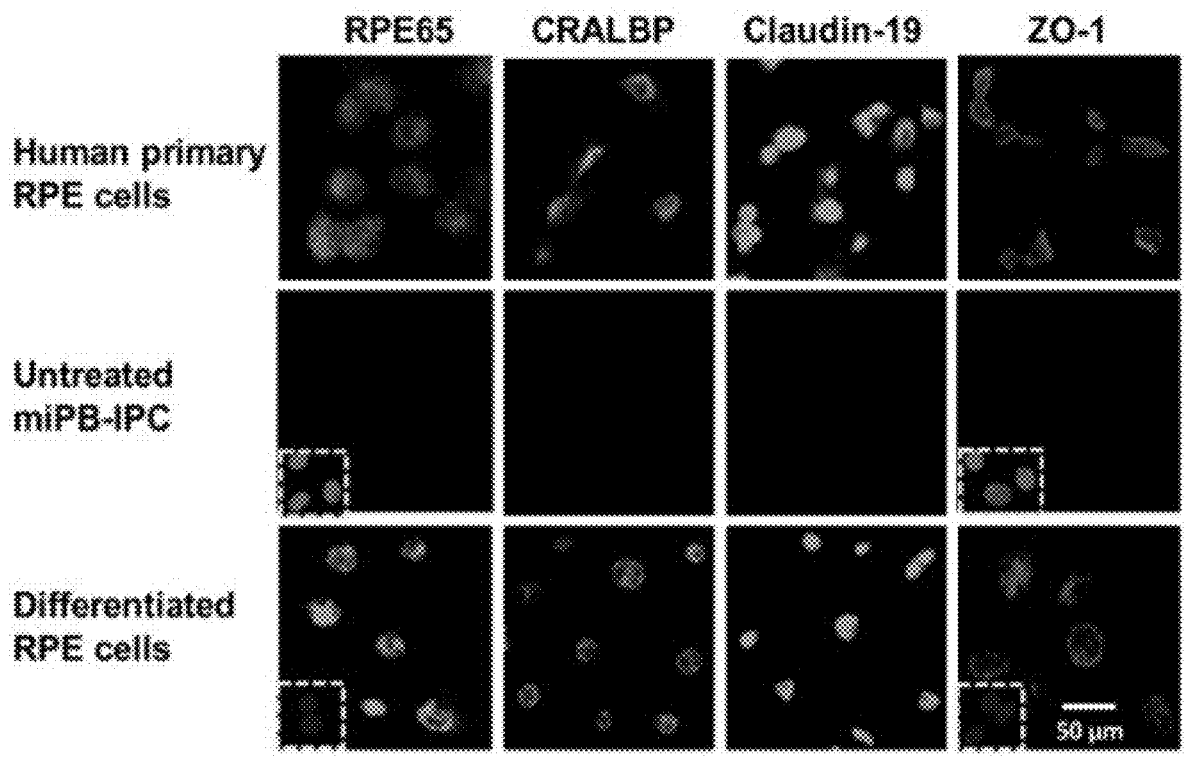
FIG. 12 shows immunostaining of differentiated RPE cells with RPE-specific markers (n=3). Human primary RPE cells served as positive controls. Mouse IgG and rabbit IgG merged with nuclear DAPI (blue) staining served as negative control (inserts). Untreated miPB-IPC served as negative control (middle panel).
Figure 13:
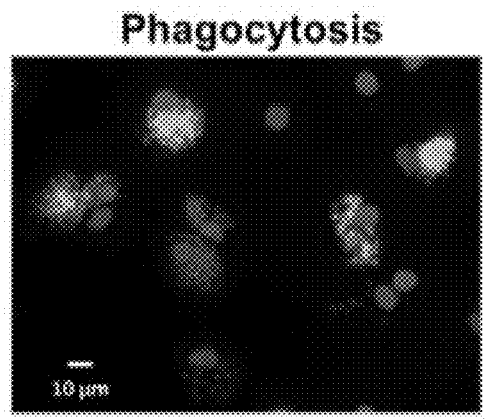
FIG. 13 illustrates phagocytosis of fluorescence beads by differentiated RPE cells (n=3).
Figure 14:
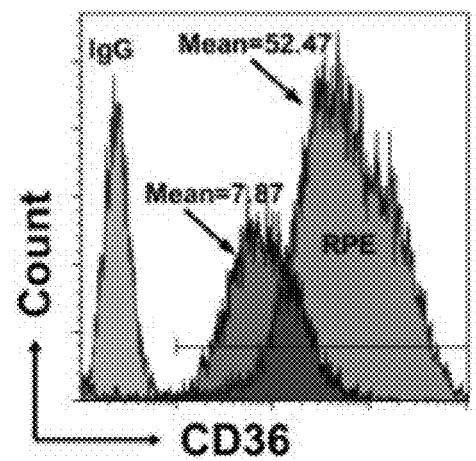
FIG. 14 shows flow cytometry analysis of CD36 expression on differentiated RPE cells and untreated cells (n=3). Isotype-matched IgG served as negative control.

Retinal pigment epithelium (RPE) is a monolayer cell that fundamentally supports visual function and the integrity of photoreceptors. Dysfunctions and loss of RPE cells is the major cause for age-related macular degeneration (AMD), leading to blindness. To determine whether miPB-IPC were multipotent, we tested their differentiation to RPE cells. FIGS. 11-14 illustrate differentiation of mitochondrion-induced PB-IPC (miPB-IPC) into retinal pigment epithelium (RPE) cells. Treatment with combined supplements (including L-glutamine, Gentamicin sulfate-Amphotericin (GA-1000), and basic fibroblast growth factor) in the presence of RPE growth media for 8 days caused >90% of miPB-IPC to acquire the RPE phenotype. Such RPE phenotype included pigmented granules in the cytoplasm, numerous cell processes at various lengths (FIG. 11), and expression of visual cycle proteins RPE65 and cellular retinaldehyde binding protein (CRALBP). It further included tight junction-associated membrane proteins claudin-19 and Zonular occludens-1 (ZO-1) (FIG. 12, bottom), similar to primary human RPE cells (FIG. 12, top). Functional analysis yielded a strong phagocytosis of fluorescence beads (FIG. 13) and an up-regulated expression of phagocytic marker CD36 (FIG. 14), similar to human RPE cells. Untreated cells acted as a control and failed to show these changes. These results indicated differentiated RPE cells which acquired the phenotype of human RPE cells.

Example 3

Figure 15:
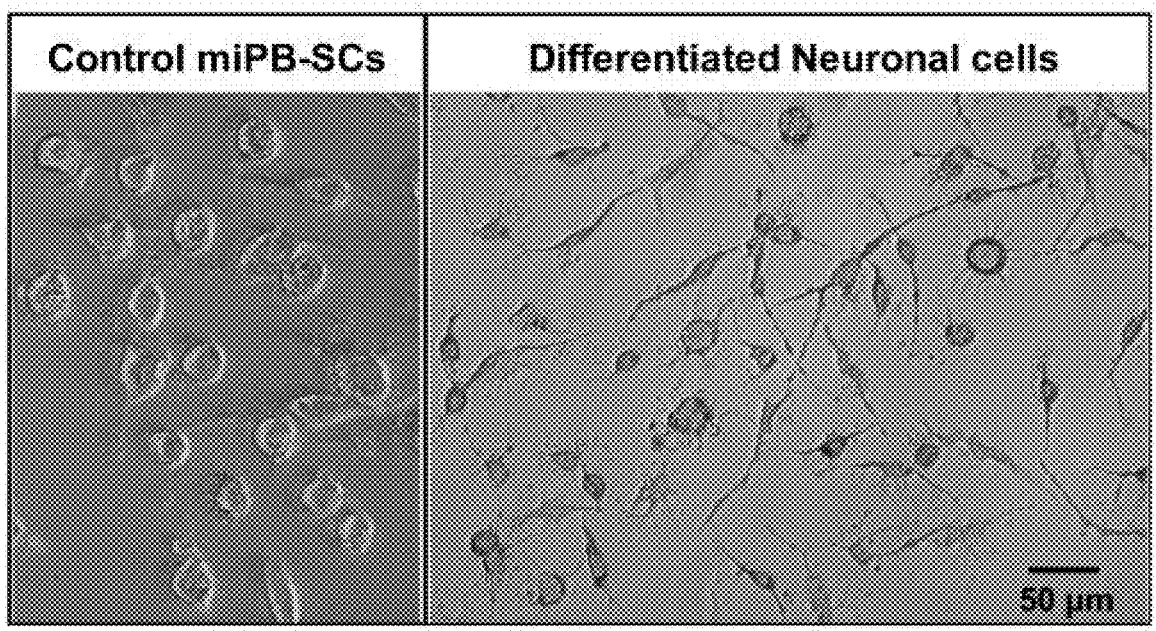
FIG. 15 is phase contrast imaging showing differentiation of miPB-IPC into neuronal cells (n=5).
Figure 16:
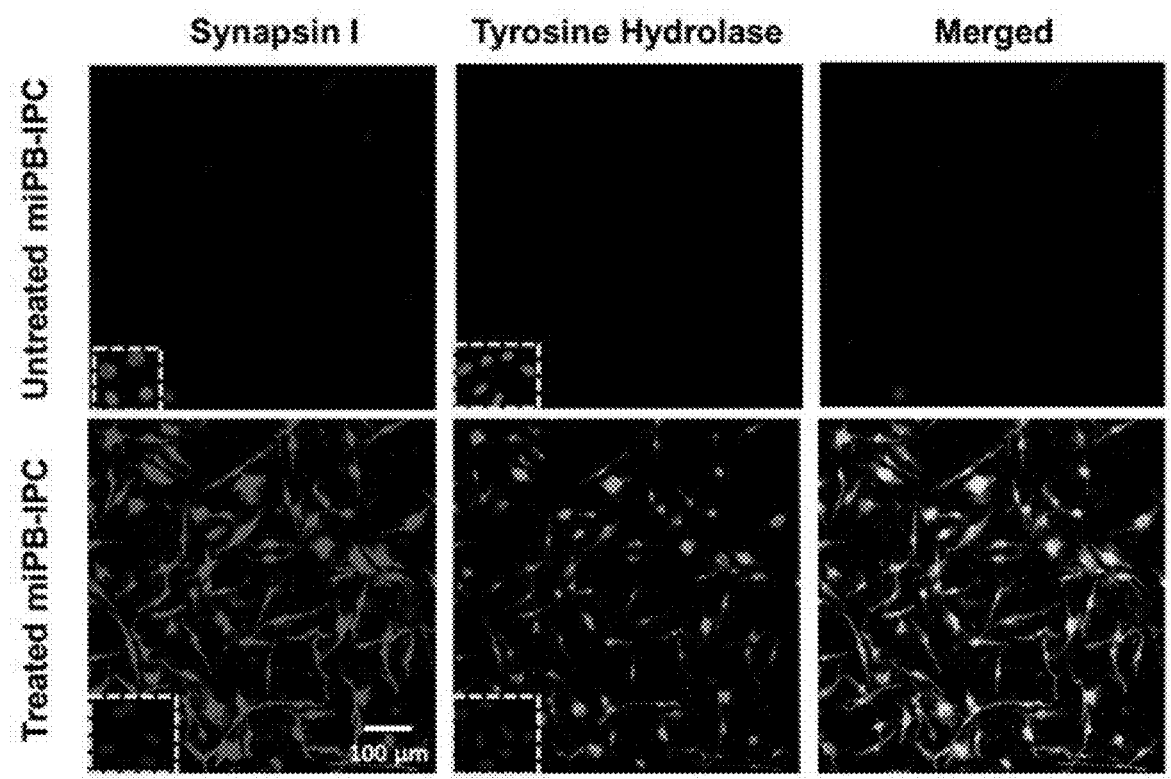
FIG. 16 shows immunostaining of differentiated neuronal cells with neuron-specific markers synapsin I and tyrosine hydroxylase (n=3). IgG staining served as negative control (inserts). Untreated miPB-IPC served as negative control (top panel).
Figure 17:
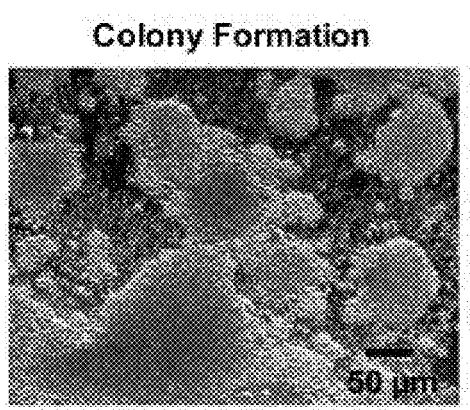
FIG. 17 illustrates colony formation of miPB-IPC with different sizes in regular miPB-IPC cell cultures (n=5).

Ex Vivo Differentiation of Mitochondrion-Induced PB-IPC (miPB-IPC) into Neuronal Cells During the induction of RPE cell differentiation, a few elongated neuronal-like cells were observed. Accordingly, the differentiation potential of miPB-IPC to neuronal cells was investigated. FIGS. 15-16 illustrate differentiation of miPB-IPC into neuronal cells. After treatment with 100 ng/mL neuronal growth factor (NGF) plus human neuronal stem cell growth medium in 24-well plates for 2-3 days, 99% of treated miPB-IPC displayed typical neuronal morphology including elongated axon-like processes with branches and formed cell-cell networks via dendrites (FIG. 15). Double-immunostaining revealed that 99.1% of treated cells expressed the neuronal-specific marker synapsin I and tyrosine hydroxylase (FIG. 16), a rate-limiting enzyme for the biosynthesis of catecholamines (e.g., dopamine and norepinephrine). Untreated cells only showed a spontaneous differentiation (<3%). These data indicate the adrenergic-neuronal differentiation potential of miPB-IPC.

Example 4

Clonal Analysis of miPB-IPC

Figure 18:
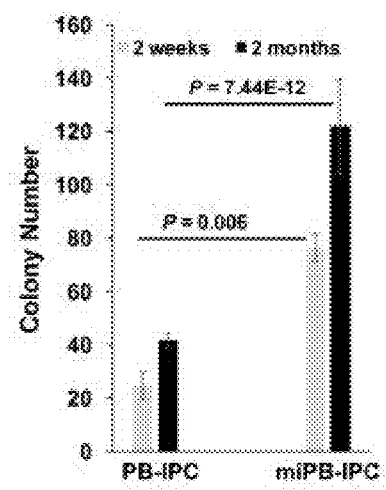
FIG. 18 is a graph showing potential difference in colony formation between miPB-IPC relative to untreated PB-IPC. Data are presented as mean±SD from five preparations.
Figure 19:
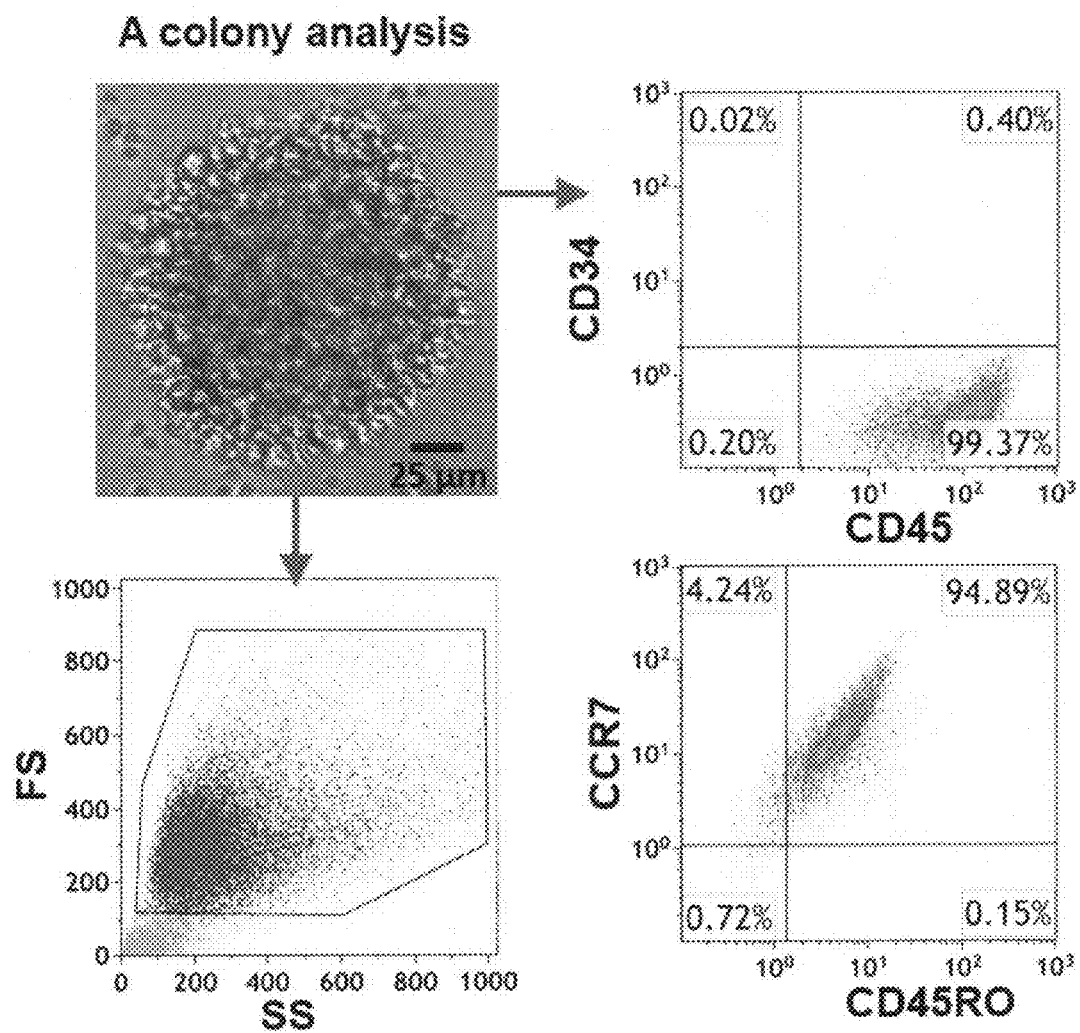
FIG. 19 shows phenotypic analysis of single colony-derived cells, retaining PB-IPC markers CD34−CD45+ SOX2+CD45RO+CCR7+ (n=5).
Figure 20:
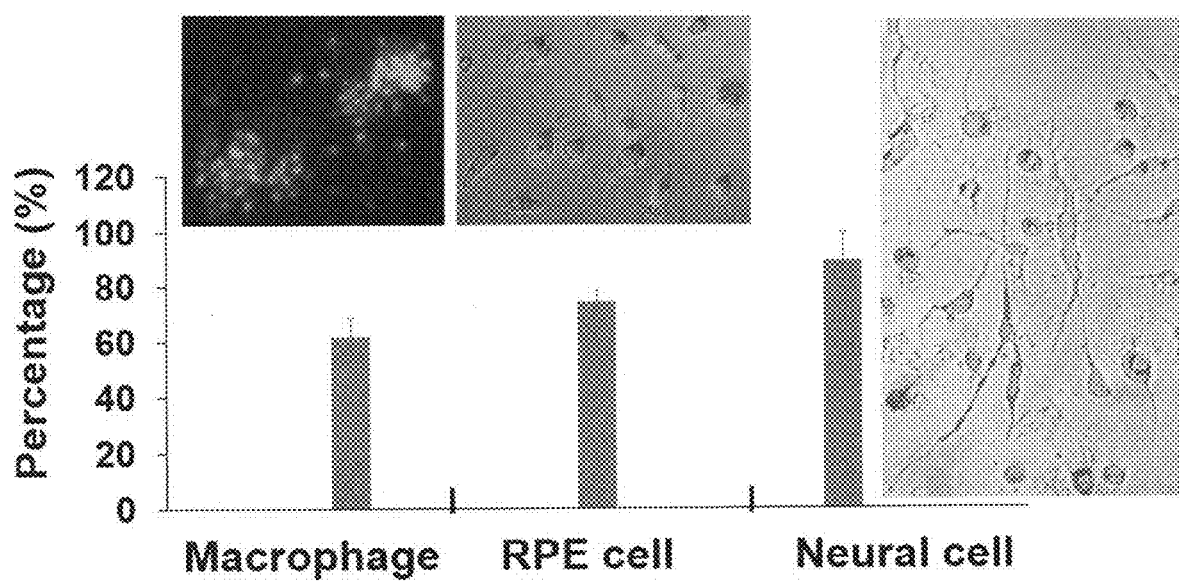
FIG. 20 shows clonal analysis. A single colony was dispersed and inoculated into 96-well plates, treated wells with different lineage-specific inducers for differentiations, including macrophages (left, phagocytosis of fluorescent beads, n=3), RPE cells (middle, n=6), and neural cells (right, n=9).
Figure 21:
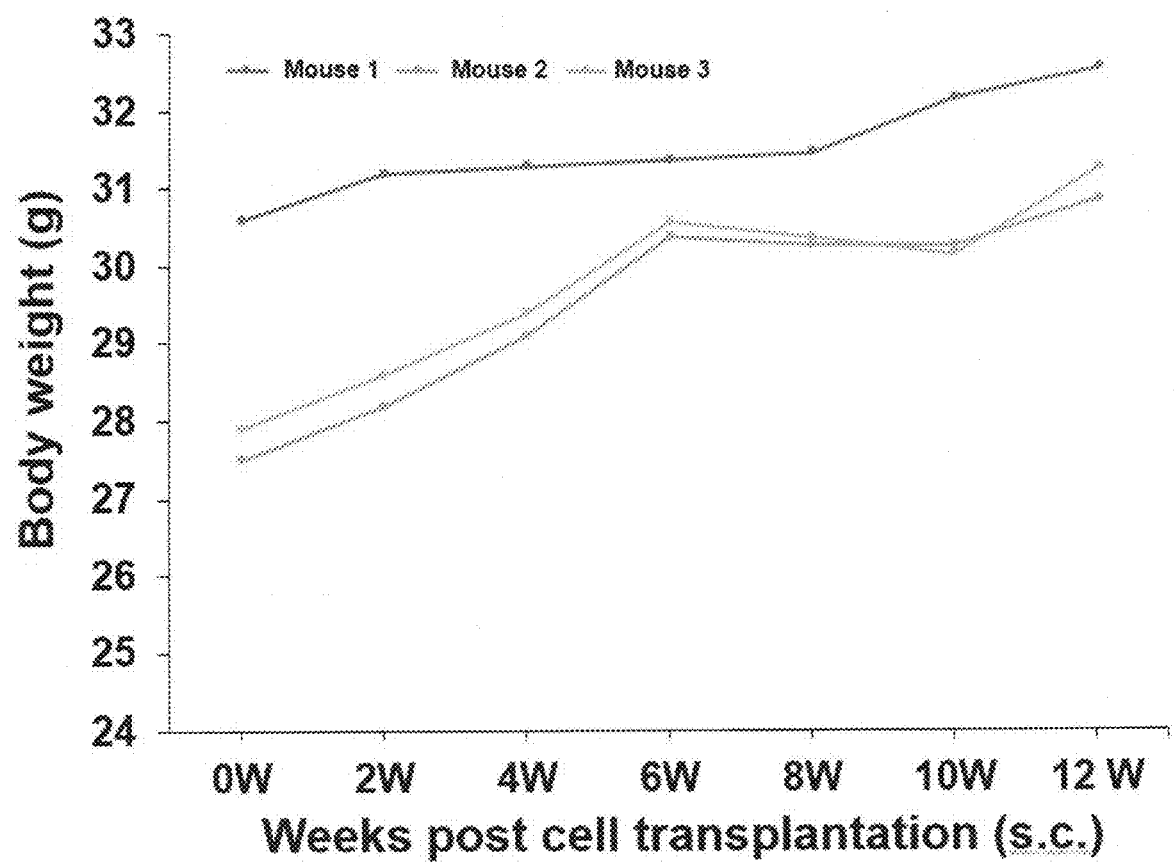
FIG. 21 illustrates weight gain in miPB-IPC-transplanted mice, without tumor formation. The miPB-IPC at a dose of 2×10$^7$ cells/mouse were inoculated (s.c., right lower flank) in NOD-scid IL-2Rγ$^{null}$ mice (n=3). Injection of equal volume of physiological saline on the left lower flank served as control.

To further determine the multipotency of miPB-IPC, clone analysis was performed. FIGS. 17-23 illustrate the clonal analysis of miPB-IPC and testing for tumor formation of miPB-IPC. Colony formation of miPB-IPC was observed with different sizes (FIG. 17), and the potential for colony formation of miPB-IPC was markedly increased after treatment with mitochondria relative to untreated PB-IPC (FIG. 18). Colony formation of miPB-IPC had occurred in different sizes at a 2-month culture in a 24-well plate. The miPB-IPC were initially cultured with serum-free NutriStem® hPSC XF culture medium (Corning) at $1\times10^4$ cells/mL/well in 24-well tissue culture plates, at 37° C. in 8% $CO_2$ culture conditions. Data are presented as mean±SD from five preparations. Flow cytometry verified that these colonies retained PB-IPC markers $CD45^+$ and $CD34^-$ (94.7±4.29%, n=3), $SOX2^+$ (77.38±13.34%), and $CD45RO^+$ and $CCR7^+$ (92.4±3.6%) (FIG. 19). Five colonies were dispersed and inoculated into 96-well plates. After treatment with different lineage-specific inducers including 50 ng/ml M-CSF for macrophage differentiation, 100 ng/mL NGF for neuronal cells, and RPE cells with specific condition medium, characterization of different lineage markers substantiated that 62.05±6.43% of differentiated Mφ exhibited phagocytosis of fluorescence beads (FIG. 20, left), 75.6±4.8% of differentiated RPE cells were RPE65-positive (FIG. 20, middle), and 94.8±1.7% of differentiated neuronal cells were synapsin I-positive (FIG. 20, right), each with distinctive morphologies. Untreated cells showed minimal spontaneous differentiation (<5%). These data demonstrate that single-colony-derived cells can give rise to different cell lineages such as macrophages, RPE cells, and neuronal cells, confirming the multipotent nature of miPB-IPC.

Additional study confirmed there was no tumor formation after transplant of miPB-IPC at the dose of $2 \times 10^7$ cells/mouse (s.c.). The miPB-IPC-transplanted mice gained weight at the time of a 12-week follow-up (FIG. 21, n=3 mice), without evident tumor formation upon tissue inspection (lung, liver, spleen, and kidney), indicating the safety of the miPB-IPC application.

Figure 22:
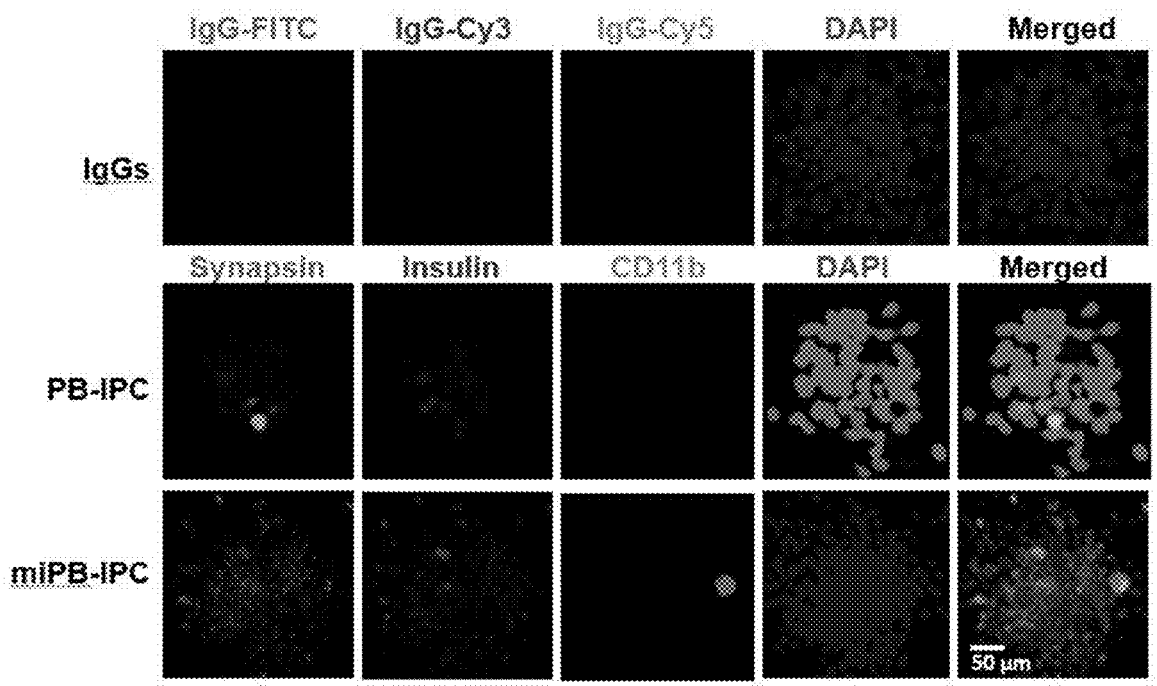
FIG. 22 is colony analysis imaging with three-germ layer-associated markers (neuronal marker synapsin I for ectoderm, islet β cell marker insulin for endoderm, and macrophage marker CD11b for mesoderm). IgGs served as negative controls (top panel). Representative images were from one of eight colonies for miPB-IPC group (bottom panel) and five colonies for control PB-IPC (middle panel).
Figure 23:
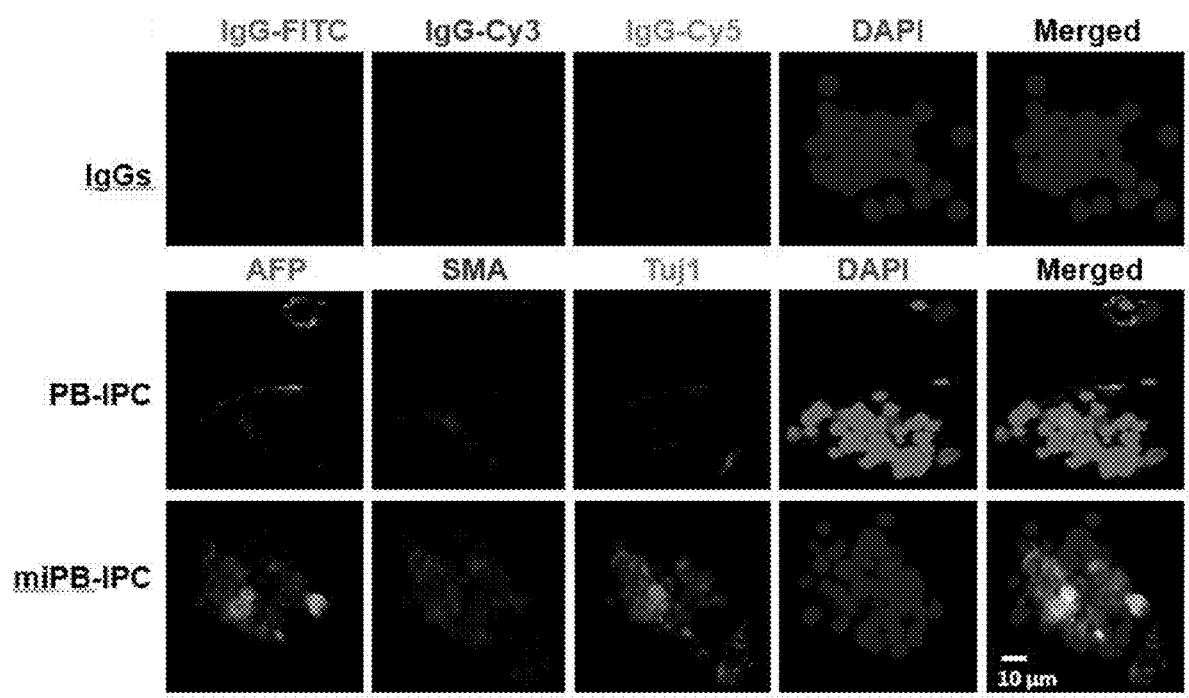
FIG. 23 is colony analysis imaging with additional three-germ layer-associated markers (neuronal marker beta III tubulin (Tuj1) for ectoderm, liver cell marker alpha-fetoprotein (AFP) for endoderm, and smooth muscle actin (SMA) for mesoderm). IgGs served as negative controls (top panel). Representative images were from one of seven colonies for miPB-IPC group (bottom panel) and five colonies for control PB-IPC (middle panel).
Figure 24:
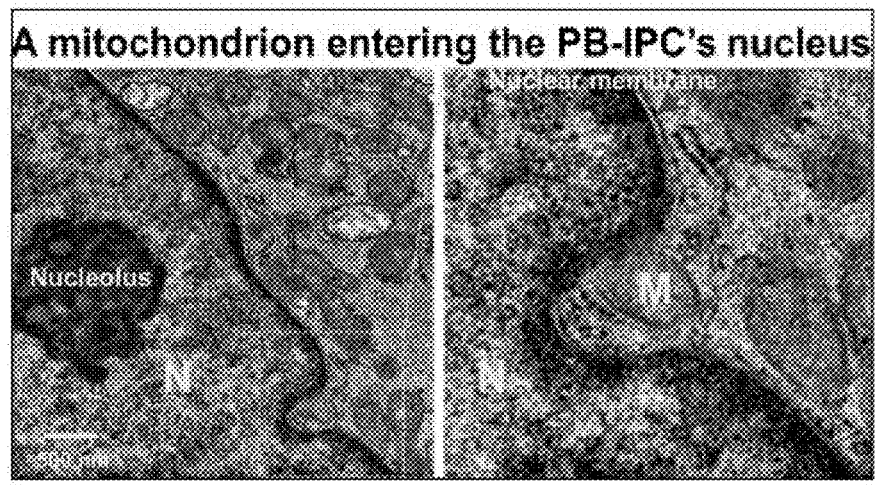
FIG. 24 is transmission electron microscopy imaging showing a mitochondrion (M) crossing the nuclear membrane of a mitochondrion-treated PB-IPC.

To determine the multipotent differentiations of miPB-IPC, colony analysis with three-germ layer-associated markers was performed, including a neuronal marker synapsin for ectoderm, the islet β cell marker insulin for endoderm, and a macrophage marker CD11b for mesoderm. Confocal microscopy demonstrated that there were more three-germ layer-positive cells distributed in miPB-IPC-derived colonies than those in mitochondrion-untreated PB-IPC-derived colonies (FIG. 22). Using the three-germ layer immunocytochemistry kit (Invitrogen), colony analysis was repeated with additional three-germ layer-associated markers, including a neuronal marker beta III tubulin (Tuj1) for ectoderm, the liver cell marker alpha-fetoprotein (AFP) for endoderm, and smooth muscle actin (SMA) for mesoderm. The data confirmed spontaneously differentiated three-germ layer-positive cells in miPB-IPC-derived colonies (FIG. 23). The number of positive cells was very low or negative in the mitochondrion-untreated PB-IPC-derived colonies (FIG. 23). Thus, the data showed multipotency of miPB-IPC.

Example 5

Penetration of Mitochondria into Nuclei of PB-IPC

Figure 25:
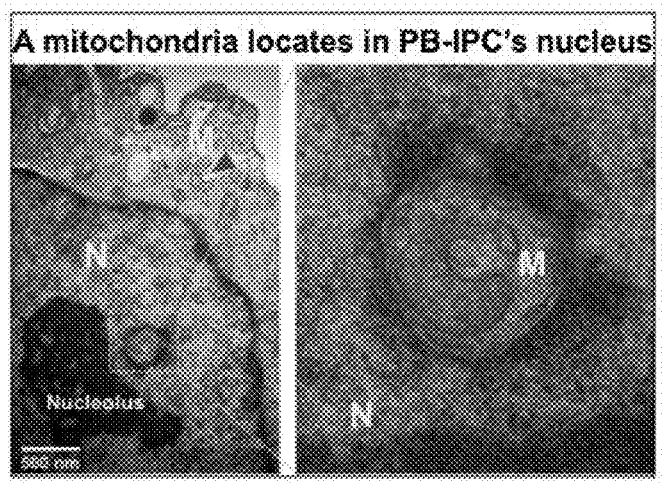
FIG. 25 is transmission electron microscopy imaging showing a mitochondrion located inside the nuclear matrix and close to the nucleolus with a morphologically-similar mitochondrion (indicated by arrow) in the cytoplasm.
Figure 26:
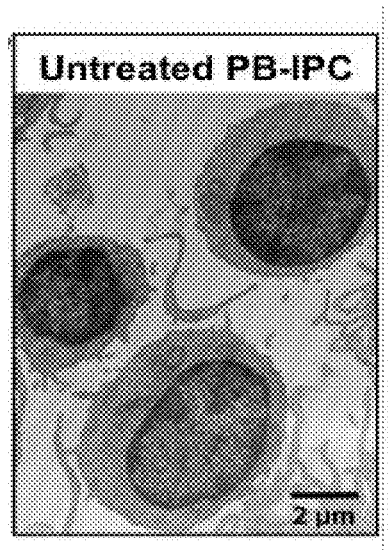
FIG. 26 shows the ultrastructure of untreated PB-IPC.
Figure 27:
FIG. 27 illustrates the penetration of red fluorescent protein (RFP)-labeled mitochondria into PB-IPC. After PB-IPC were treated with RFP-labeled mitochondria for 4 h, confocal microscopy established RFP+ mitochondria infiltrating the cytoplasm (n=5). Distribution of RFP+ mitochondria inside of a nuclear was represented by an arrow. RFP+ mitochondria were colocalized with Hoechst 33342-labeled nuclear and the differential interference contrast (DIC) image (left).
Figure 28:
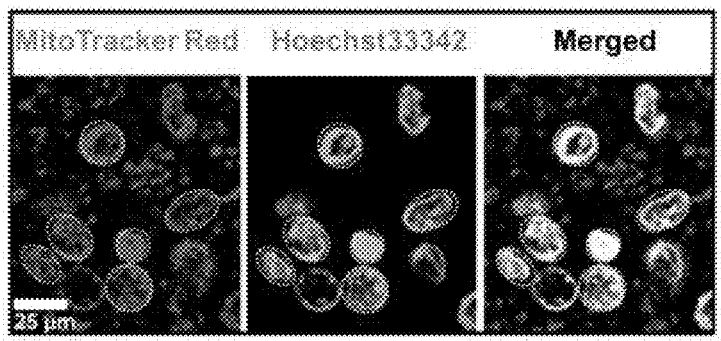
FIG. 28 shows MitoTracker Red-labeled mitochondria entered nuclei, and their colocalization is shown by confocal microscopy (n=5). Isolated mitochondria from platelets were co-cultured with purified nuclei of PB-IPC for 4 h in the presence of serum-free culture medium X-VIVO 15 at 37° C. and 5% $CO_2$.
Figure 29:
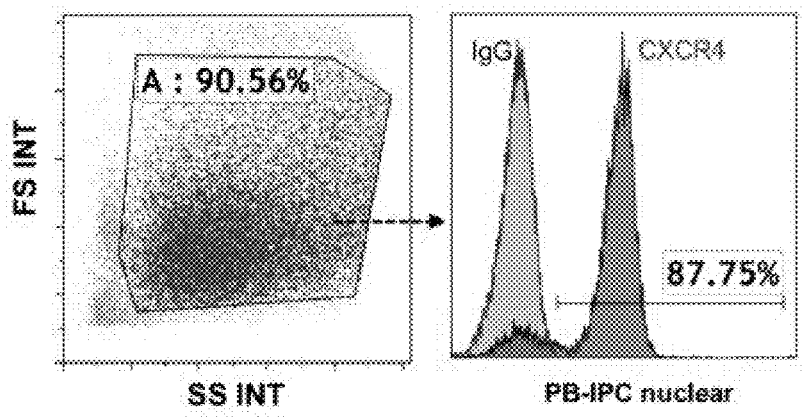
FIG. 29 shows expression of CXCR4 on the membrane of purified nuclei (n=4).

To explore the action of exogenous platelet-derived mitochondria in PB-IPC, mitochondria migrating to the nuclei of PB-IPC following treatment conditions was observed through electron microscopy, as shown in FIGS. 24-31. Mitochondria were observed crossing the nuclear membrane (FIG. 24), located inside nuclear matrices and close to the nucleolus (FIG. 25), and with a similar shape of mitochondrion in the cytoplasm (FIG. 25, indicated by arrow). Untreated PB-IPC failed to show such marked phenomena (FIG. 26). To further confirm the penetration of exogenous mitochondria into PB-IPC's nuclei, PB-IPC were treated with red fluorescent protein (RFP)-labeled mitochondria (FIG. 27), which were isolated from a HEK 293 cell line. After the treatment for 4 hours, confocal microscopy established RFP+ mitochondria infiltrating the cytoplasm (FIG. 27). To directly visualize the interaction between the mitochondria and the nucleus, freshly-purified PB-IPC-derived nuclei were treated with isolated MitoTracker Red-labeled mitochondria. Confocal imaging revealed direct interaction of mitochondria with nuclei, while some labeled mitochondria entered nuclei (FIG. 28). Based on the observation under transmission electronic microscope (TEM) and flow cytometry by staining with mitochondrial markers including MitoTracker Deep Red staining, anti-cytochrome C, and anti-heat shock protein (HSP) 60 mAbs, the frequency of intra-nuclear mitochondria was approximately 1-3%.

Figure 30:
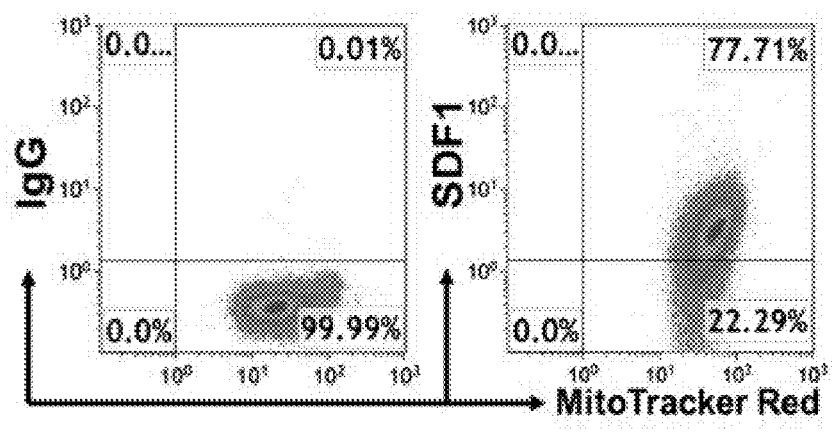
FIG. 30 shows mitochondria displaying CXCR4 ligand SDF-1 (n=4).
Figure 31:
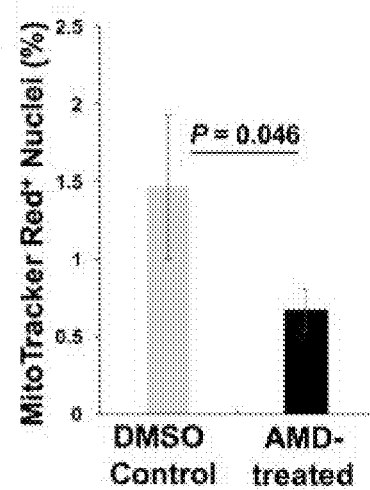
FIG. 31 illustrates a blocking experiment with CXCR4 receptor antagonist AMD 3100. Purified PB-IPC nuclei were treated with MitoTracker Red-labeled purified mitochondria in the presence or absence of AMD 3100 (30 µM, n=3). An equal concentration of solvent DMSO served as control. After the treatment for 4 hrs, nuclei were washed twice with PBS and prepared for flow cytometry.

Next, the molecular mechanisms underlying the migration of mitochondria to nuclei were explored. Flow cytometry demonstrated that nuclei displayed the chemokine receptor CXCR4 (the ligand for stromal cell-derived factor (SDF)-1) (FIG. 29), while mitochondria expressed SDF-1 (FIG. 30). To determine whether the action of SDF-1/CXCR4 contributed to the penetration of mitochondria into nuclei, a blocking experiment with CXCR4 receptor antagonist AMD3100 was performed. Purified PB-IPC nuclei were treated with MitoTracker Deep Red-labeled purified mitochondria in the presence or absence of AMD 3100. After the treatment for 4 hours, flow cytometry demonstrated that the percentage of MitoTracker Deep Red-positive nuclei was markedly reduced after the treatment with AMD 3100 (FIG. 31). This indicates that mitochondria entered into nuclei through the chemoattractant interactions between SDF-1 and CXCR4.

Figure 32:
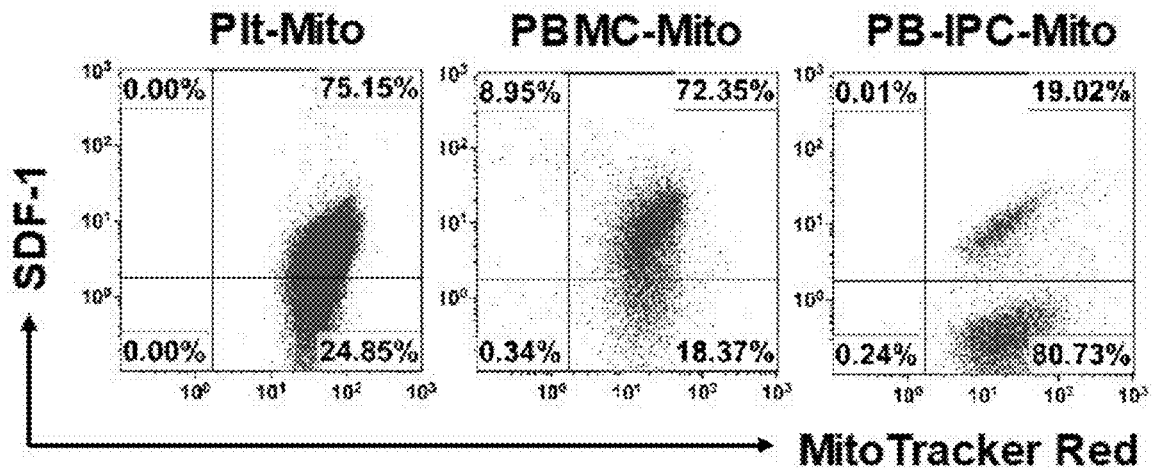
FIG. 32 shows flow cytometry illustrating the expression of SDF-1 on the platelet-derived mitochondria, PBMC-derived mitochondria, and PB-IPC-derived mitochondria. Isotype-matched IgGs served as controls. Data were representative from three experiments.
Figure 33:
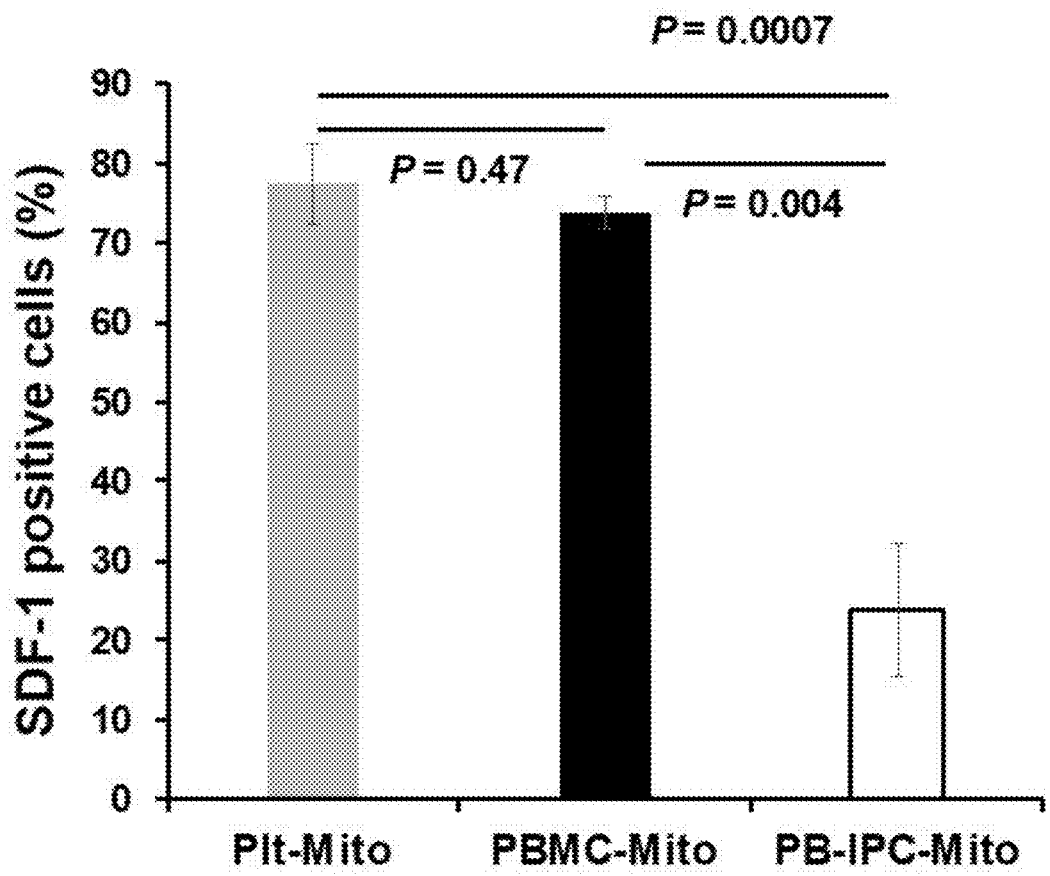
FIG. 33 shows a graphic comparison of the level of SDF-1 expression among platelet-derived mitochondria (Plt-Mito) and PBMC-derived mitochondria (PBMC-Mito) having no marked difference, but much lower SDF-1 expression among PB-IPC-derived mitochondria (PB-IPC-Mito). Data represent mean±SD, n=3.
Figure 34:
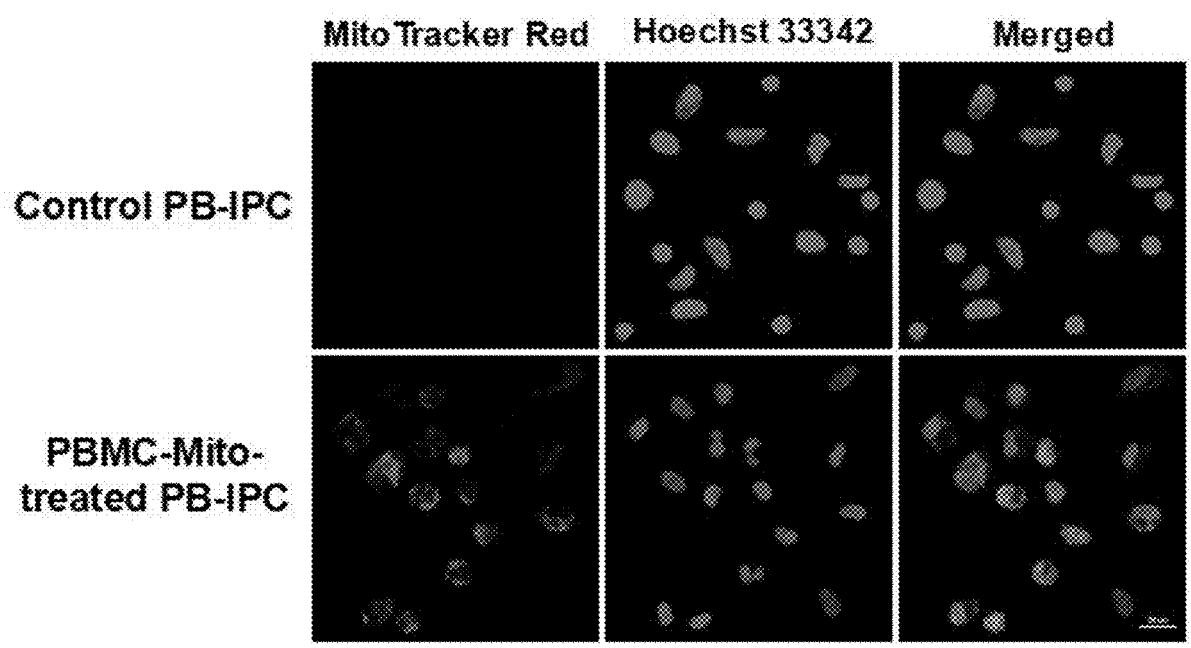
FIG. 34 is confocal microscopy imaging showing the penetration of PBMC-derived mitochondria into the nucleus of PB-IPC.

Additionally, it was observed that PBMC-derived mitochondria (not platelet-derived) could also penetrate the nucleus of PB-IPC with the incidence of 2.09±0.87%. FIGS. 32-34 show comparisons of SDF-1 expression among platelet-derived mitochondria, PBMC-derived mitochondria, and PB-IPC-derived mitochondria. Flow cytometry revealed that PBMC-derived mitochondria displayed a similar level of SDF-1 expression as that of platelet-derived mitochondria, but much higher than that of PB-IPC-derived mitochondria. PB-IPC were treated with MitoTracker Red-labeled PBMC-derived mitochondria (100 µg/ml) at 37° C. in 5% $CO_2$. After treatment for 4-6 hours, cells were observed and photographed with a Nikon AIR confocal microscope on an Nikon Eclipse Ti2 inverted base, using software NIS Elements Version 4.60. (FIGS. 32-34). Taken together with the results of blocking with CXCR4 receptor antagonist AMD 3100 on the purified nuclei of PB-IPC, these data indicate that the SDF-1/CXCR4 pathway contributes to the migration of mitochondria to the nuclear membrane of PB-IPC, leading to the penetration of the nucleus of PB-IPC.

Example 6

Genetic and Epigenetic Changes in PB-IPC after the Treatment with Mitochondria

Figure 35:
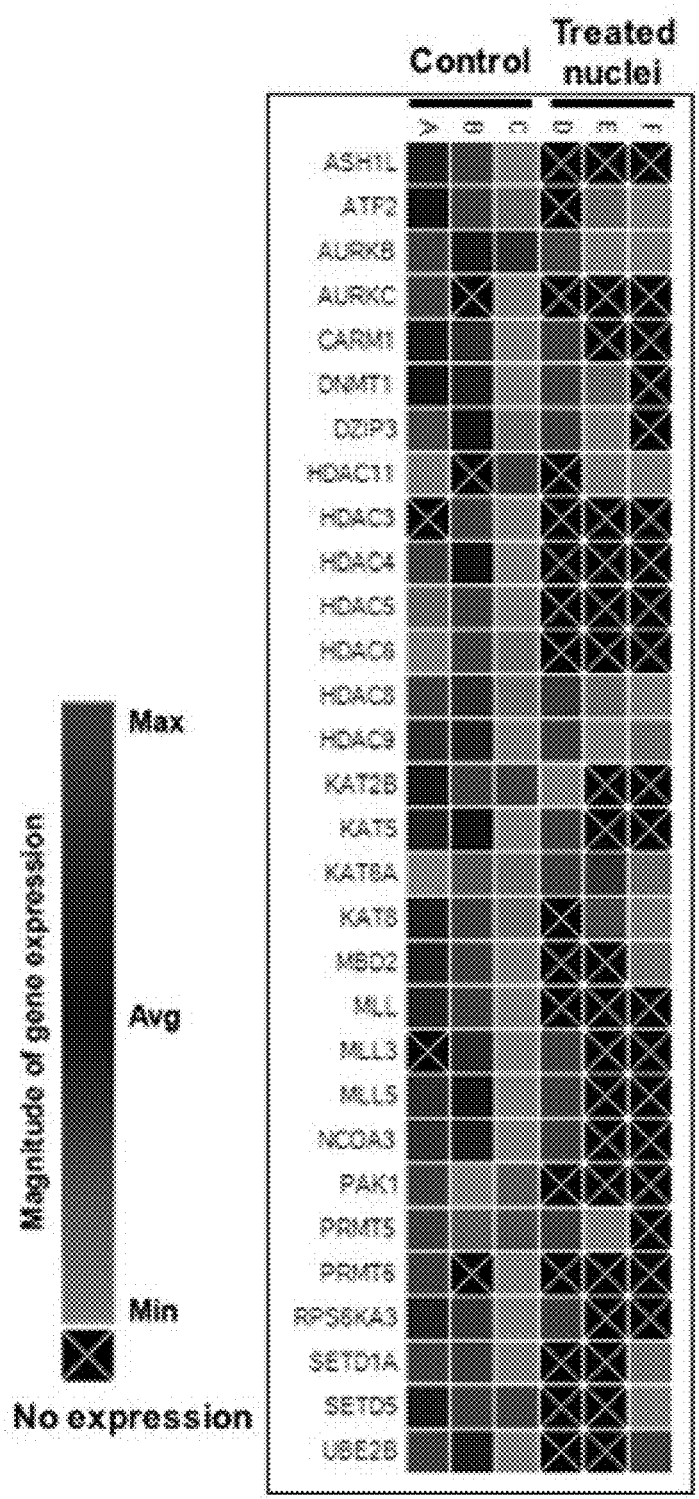
FIG. 35 shows a real time PCR array for epigenetic chromatin modification enzyme-related genes.

To investigate the mechanism by which mitochondria modulate expression in the nucleus, purified PB-IPC-derived viable nuclei were treated with isolated mitochondria for 4 hours at 37° C. and 5% $CO_2$, and changes in transcription were assessed by real-time PCR array. The data uncovered the marked changes in epigenetic chromatin modification enzyme-related genes including DNA methyltransferase 1 (DNMT1), histone acetyltransferases (activation transcription factor-2 (ATF2), lysine acetyltransferase 2B (KAT2B), KAT5, and KAT8), histone methyltransferases (coactivator-associated arginine methyltransferase 1 (CARM1), mixed lineage leukemia protein (MLL), MLL3, Protein arginine methyltransferase 5 (PRMT5), and PRMT6), histone methyltransferase activity-associated SET (Su (var), Enhancer of Zeste and Trithorax) domain proteins (ASHIL (absent, small, or homeotic)-like (*Drosophila*), SET domain containing 1A (SETDIA), and SETD5), histone phosphorylation ((aurora kinase B (AURKB), AURKC, p21 protein-activated kinase 1 (PAK1), and ribosomal protein S6 kinase polypeptide 3 (RPS6KA3)), Histone ubiquitination (DAZ interacting protein 3(DZIP3) and ubiquitin-conjugating enzyme E2B (UBE2B)), DNA and histone demethylase methyl-CpG binding domain protein 2 (MBD2), and histone deacetylases (histone deacetylase 3 (HDAC3), HDAC4, HDAC5, HDAC6, HDAC8, HDAC9, and HDAC11)) (FIG. 35).

Figure 36:
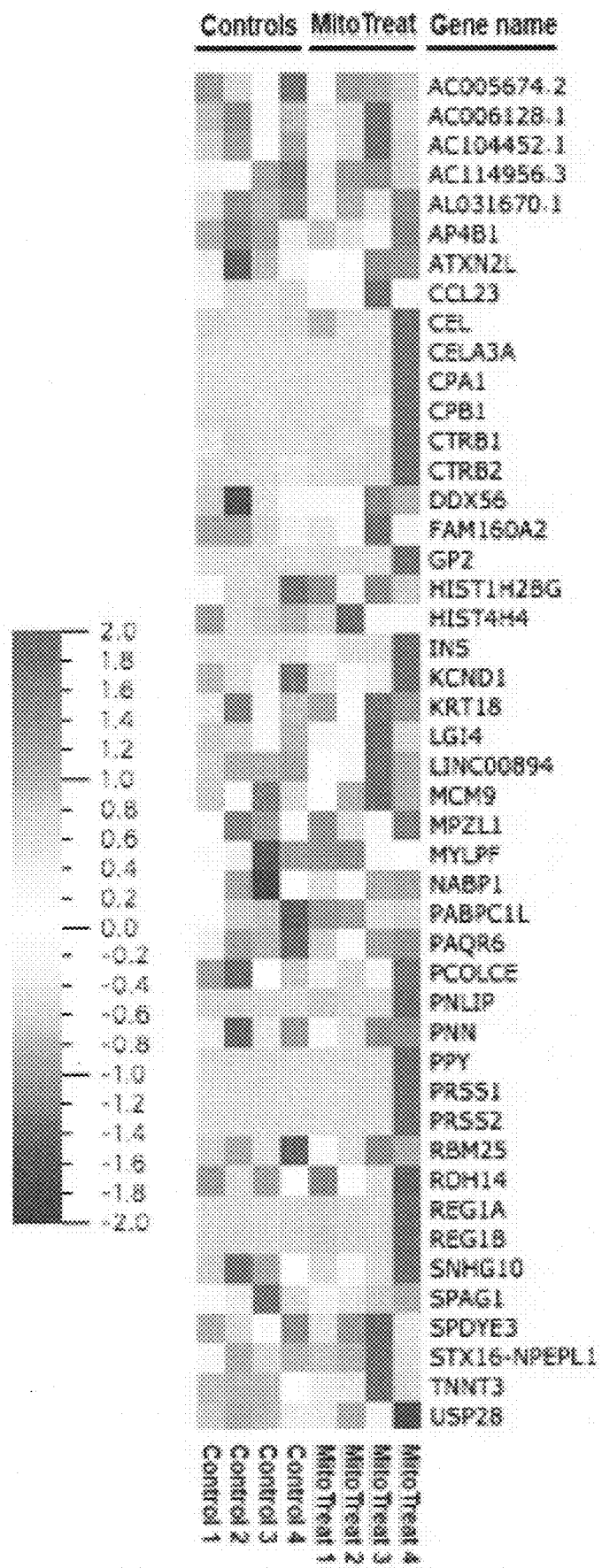
FIG. 36 shows an RNA-sequencing heatmap showing forty-six differentially expressed genes in PB-IPC after treatment with mitochondria.
Figure 37:
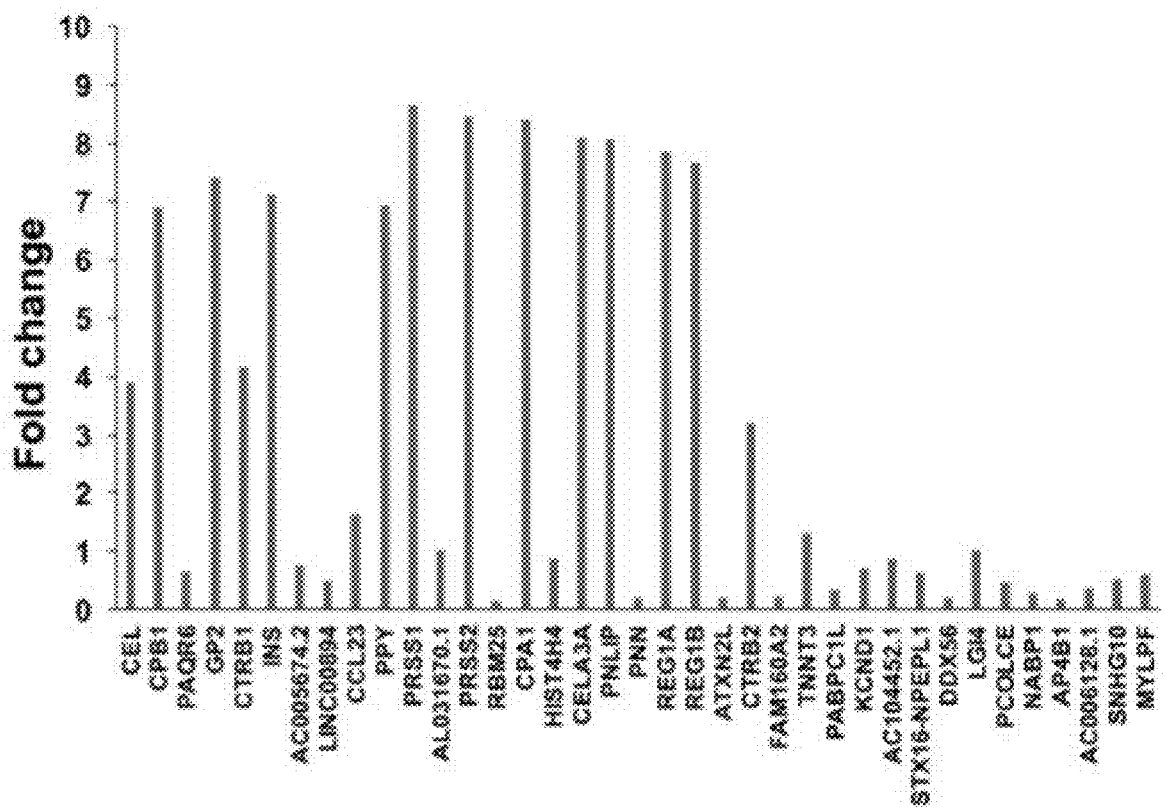
FIG. 37 shows RNA-sequencing data showing thirty-seven up-regulated genes in PB-IPC after treatment with mitochondria.
Figure 38:
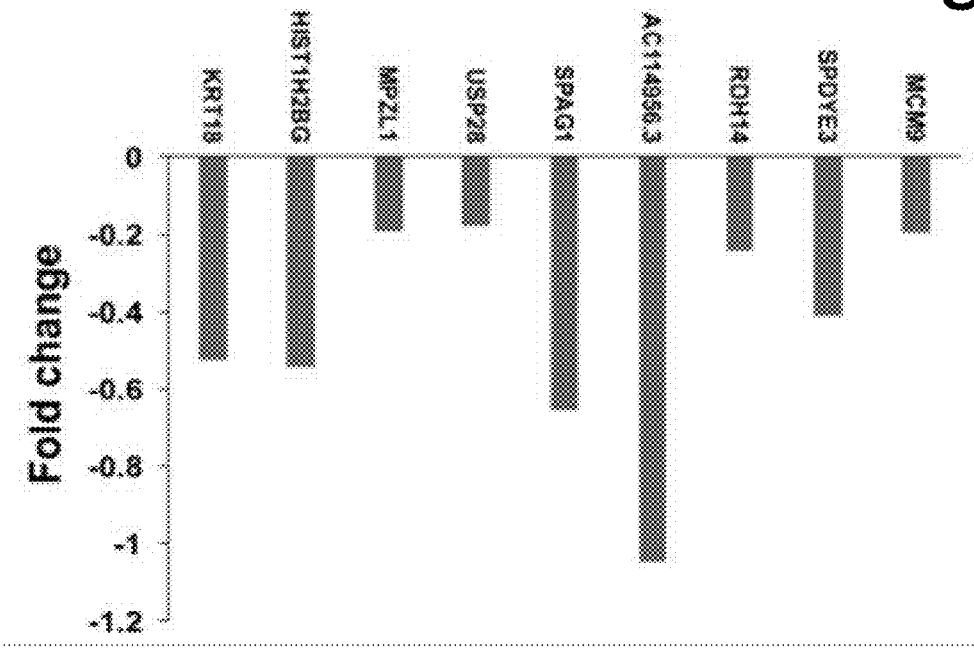
FIG. 38 shows RNA-sequencing data showing nine down-regulated genes in PB-IPC after treatment with mitochondria.

These data demonstrate that mitochondria that penetrate the nucleus contribute to both epigenetic and genetic regulations, leading to the reprogramming of PB-IPC. To find more differentially expressed genes, RNA sequencing (RNA-seq) analysis was performed between the mitochondrion-treated and untreated PB-IPC in four preparations (FIG. 36). The results demonstrated that 37 genes were markedly up-regulated in the mitochondrion-treated PB-IPC (FIG. 37, p<0.05), and 9 genes were down-regulated (FIG. 38, p<0.05). There were no significant changes for other genes (n=15,388, 99.7% of genes) in PB-IPC after the treatment with mitochondria.

Example 7

Figure 39:
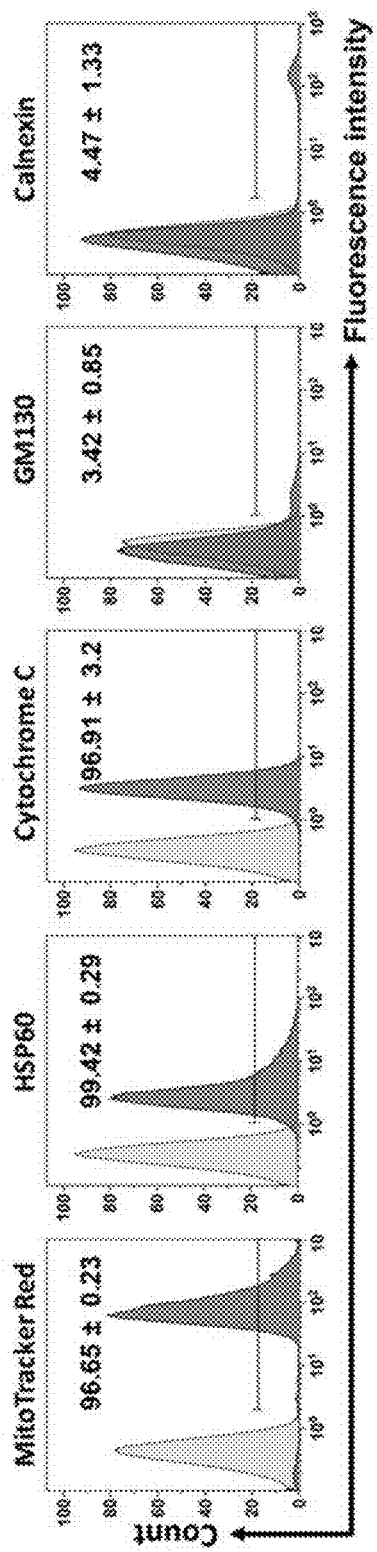
FIG. 39 shows purity analysis histograms for isolated mitochondria. Different markers were applied by flow cytometry, including MitoTrack Deep Red staining, anti-cytochrome C, and anti-heat shock protein (HSP). 60 Abs was used for mitochondrial markers, calnexin for endoplasmic reticulum (ER), and GM130 for Golgi apparatus. Isotype-matched IgGs served as negative controls (n=3).
Figure 40:
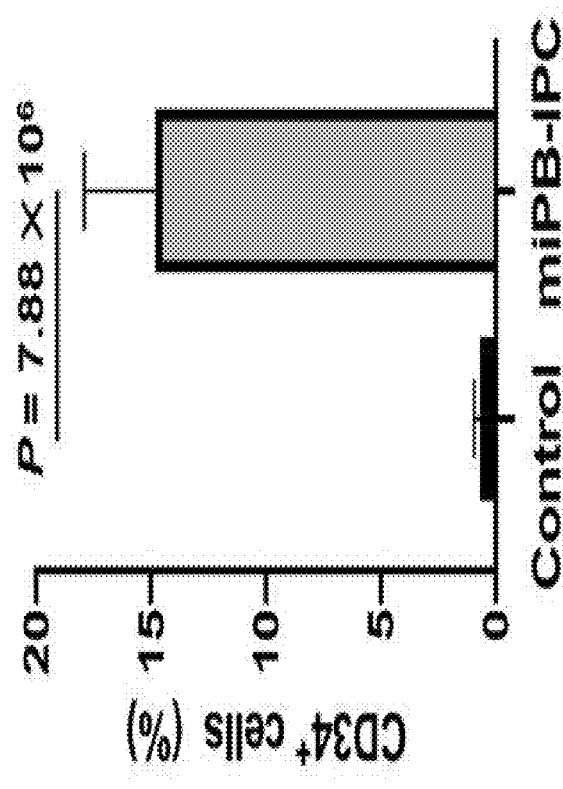
FIG. 40 shows CD34 expression upregulation after treatment with mitochondria in miPB-IPCs. Data represent mean±SD of five experiments.
Figure 41:
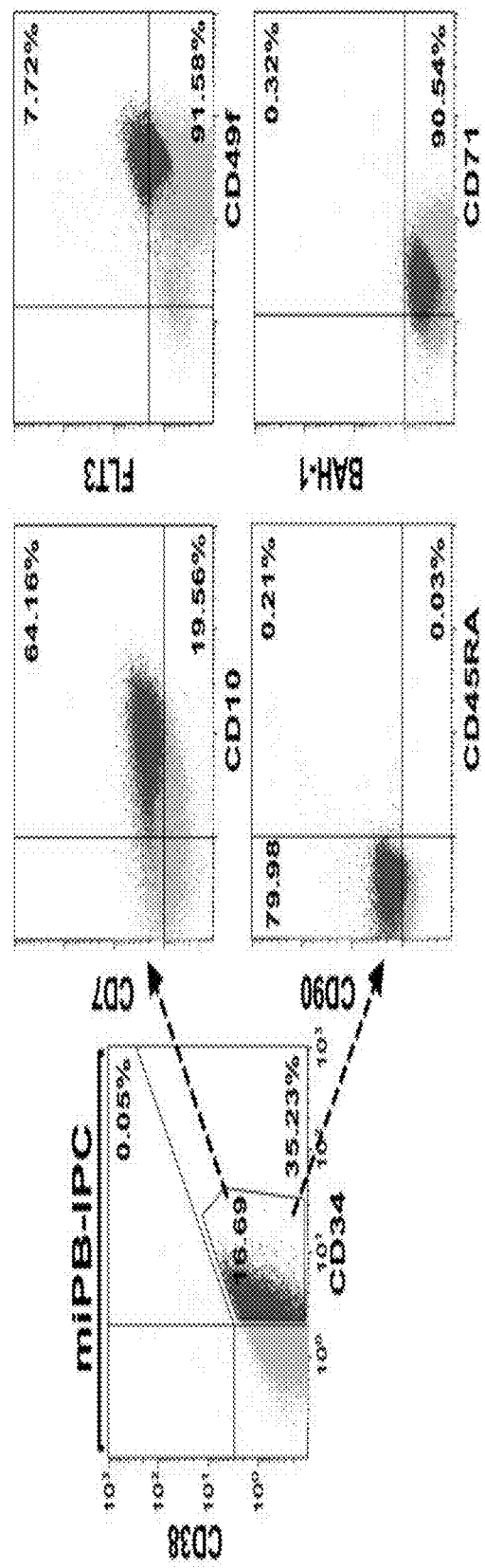
FIG. 41 shows phenotypic characterization of gated miCD34+ HSCs (dashed arrows) with additional surface markers in total miPB-IPCs. Isotype-matched IgGs served as controls. Data were representative from five preparations.
Figure 42:
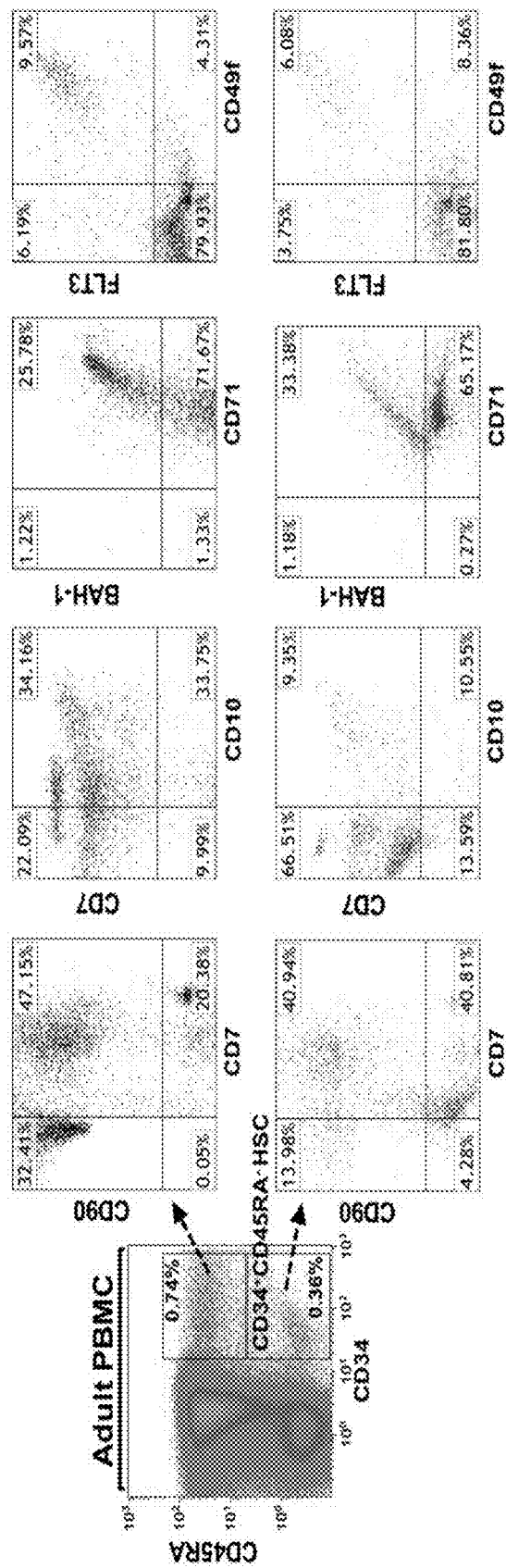
FIG. 42 shows phenotypic characterization of gated CD34$^+$CD45RA$^-$ HSCs with additional markers (bottom) and CD34$^+$CD45RA$^+$ cell population with additional markers (top) in total PBMCs (n=4). Isotype-matched IgGs served as controls. Data were representative from one of four preparations.

Ex Vivo Differentiation of Mitochondrion-Induced PB-IPCs (miPB-IPCs) into the Mitochondrion-Induced CD34$^+$-HSC-Like Cells (miCD34$^+$ HSCs) after Treatment with Platelet-Derived Mitochondria High-purity apheresis platelets (>99% CD41$^+$CD42$^+$ platelets) were obtained from the New York Blood Center for the following experimentation. FIGS. 39-42 illustrate the differentiation of PB-IPCs into CD34 HSC-like cells after treatment with platelet-derived mitochondria. To determine the purity of the mitochondria isolated from platelets, different markers were applied by flow cytometry including MitoTrack Deep Red staining, anti-cytochrome C and anti-heat shock protein (HSP) 60 Abs for mitochondrial markers, calnexin for endoplasmic reticulum (ER), and GM130 for Golgi apparatus. Flow cytometry demonstrated that 99% of isolated mitochondria were positive for MitoTrack Deep Red, HSP 60, and cytochrome C; there were about 5% cytochrome C$^+$ calnexin$^+$ cells and 4% cytochrome C$^+$GM130$^+$ (FIG. 39). The double-positive staining results may have been caused by the interaction and conjugation of mitochondria with the ER or Golgi apparatus, respectively. Flow cytometry analysis demonstrated that the purity of the isolated mitochondria was ≥90%. (FIG. 39). Purified platelet-derived mitochondria from autologous or allogeneic peripheral blood were prepared and treated to PB-IPCs that were isolated and expanded from blood samples of adult donors at the New York Blood Center (n=51; mean age of 48.76±14.97; age range from 18 to 72 years old; 24 males and 27 females). Notably, the expression of the HSC marker CD34 was upregulated in PB-IPCs after the treatment with mitochondria. A phenotypic analysis of miPB-IPCs after two weeks of mitochondrial treatment was striking in that the expression of CD34 on miPB-IPCs increased from 0.71%±0.25% to 14.8%±3.1% (p=7.88×10$^6$, n=5) (FIG. 40). Using an optimized panel of cell markers, it was observed that mitochondrion-induced CD34$^+$ (miCD34$^+$) cells displayed a phenotype of CD34$^+$CD38$^{-/low}$CD45RA$^-$CD49f$^+$CD90$^+$Flt3$^{-/low}$CD7$^+$CD10$^+$CD71$^+$BAH1$^{-/low}$ (14.8%±3.1%, n=5) (FIG. 41). In comparison to regular blood CD34$^+$CD45RA$^-$CD90$^+$Flt3$^{-/low}$CD7$^+$CD71$^+$ HSCs (0.49%±0.19%, n=4) from non-mobilized healthy donors, the miCD34$^+$ cells expressed similar surface markers as CD34$^+$CD45RA$^-$CD90$^+$Flt3$^{-/low}$CD7$^+$CD71$^+$ (15.3%±2.9%, n=5, p<0.01), but higher levels of CD10 (a marker defining human lymphoid progenitors) (99.4%±0.36% versus 20.6%±3.1%, p<0.01), CD49f (a common biomarker for most populations of stem cells) (98.8%±1.3% versus 15.4%±2.9%, p<0.01), and lower level of BAH-1 (a marker for human megakaryocyte-erythroid progenitor) (0.51%±0.2% versus 32.5%±3.9%, p<0.01) (FIGS. 41-42). Due to co-expressions of CD7 and CD10 (the surface markers for common lymphoid progenitor (CLP) cells) on miCD34$^+$ HSCs, the data suggested that miCD34$^+$ HSCs have a high potential to give rise to lymphocytes.

Example 8

Differentiation of miCD34$^+$ HSCs into T Cells

Figure 44:
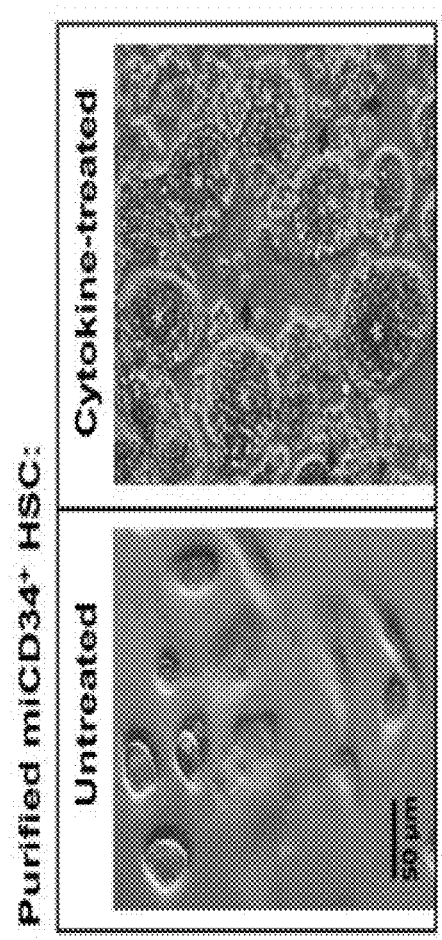
FIG. 44 is phase-contrast imaging showing T-cell differentiation of purified miCD34$^+$ HSCs in the presence of FLT-3 ligand, IL-2, and IL-7 for 3 days (n=4). Untreated cells served as a control (left). The treated-CD34$^+$ HSCs displayed substantial morphological changes with cell clusters (stars), and some floating cells (arrows) released from cell clusters (stars). Magnification: ×200.
Figure 46:
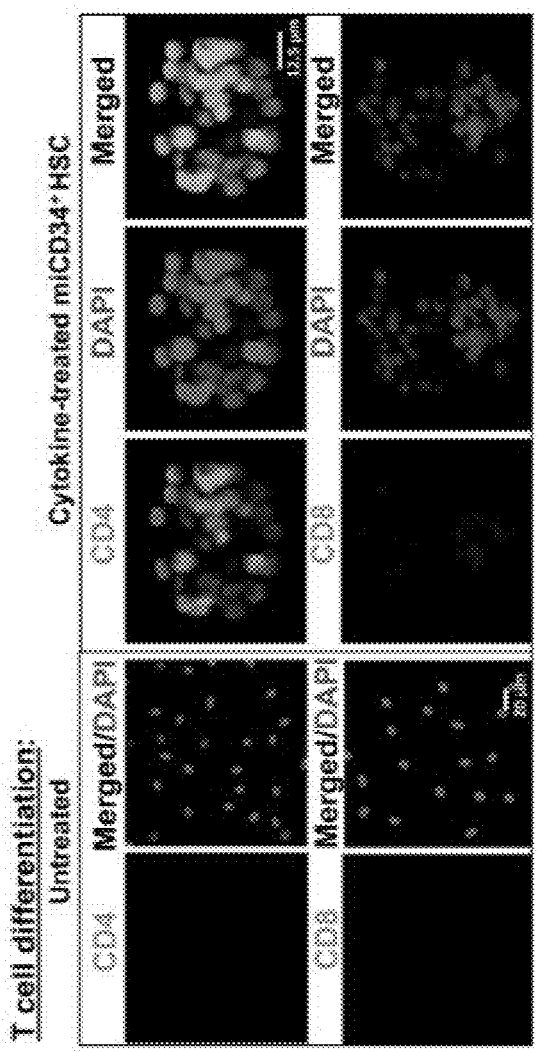
FIG. 46 shows z-stacked confocal images demonstrating strong expression of human T-cell marker CD4 with a low expression of CD8 (n=4). Untreated miCD34$^+$ HSCs served as control for immunostaining (left panel).
Figure 45:
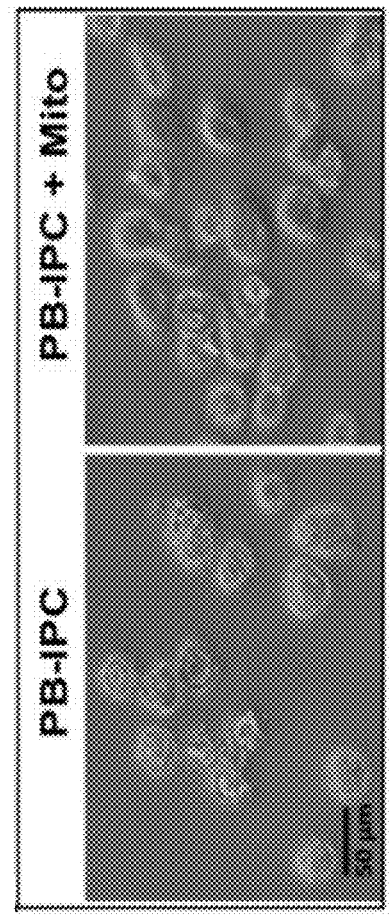
FIG. 45 is phase-contrast imaging showing the morphology of control PB-IPCs (left) and treated PB-IPCs in the presence of mitochondria (right) (n=4). Original magnification: ×200.
Figure 47:
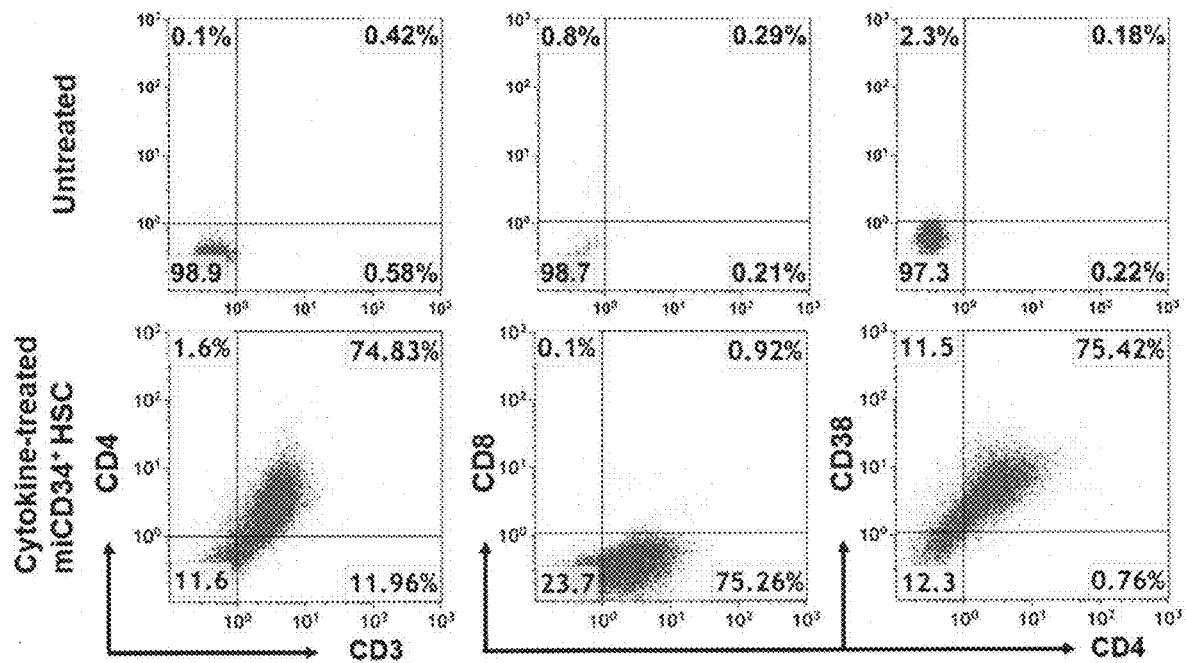
FIG. 47 shows flow cytometry illustrating that differentiated T cells were CD3$^+$CD4$^+$CD8$^-$CD38$^+$ (n=4). Untreated miCD34$^+$ HSCs served as controls (top panel).
Figure 48:
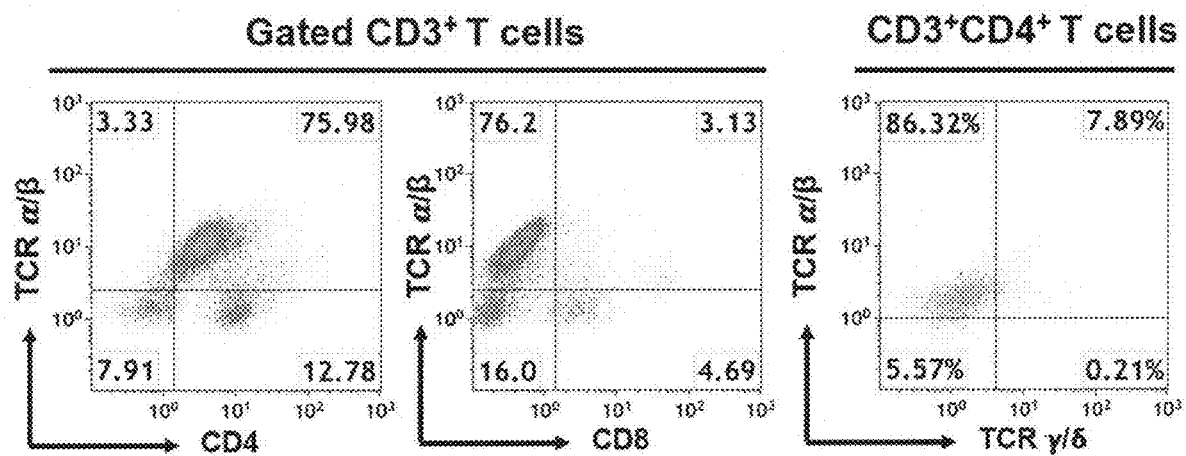
FIG. 48 illustrates expression of T-cell receptors α/β (TCRαβ) in gated CD3$^+$ and CD4$^+$ T cells (n=4).
Figure 49:
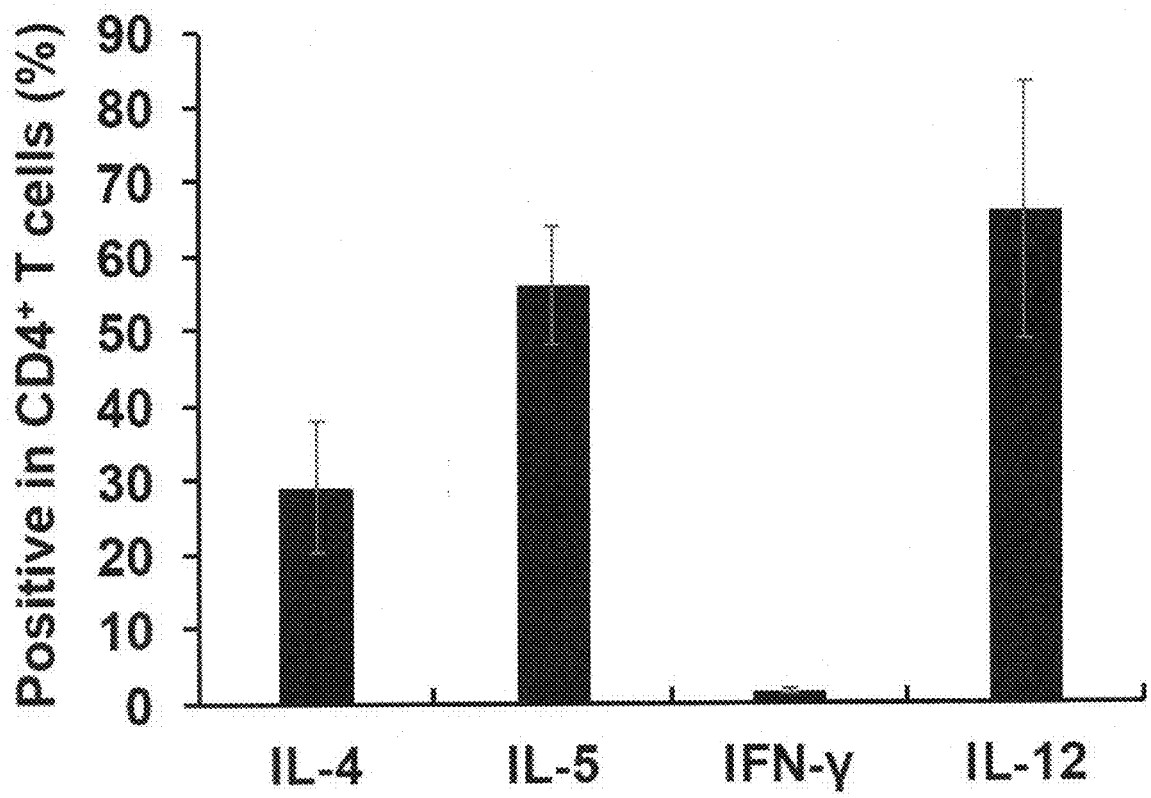
FIG. 49 shows intracellular staining of differentiated T cells with Th1/Th2 cell cytokine markers (n=3). Isotype-matched IgG served as a control. Data are presented as mean±SD from three experiments.
Figure 50:
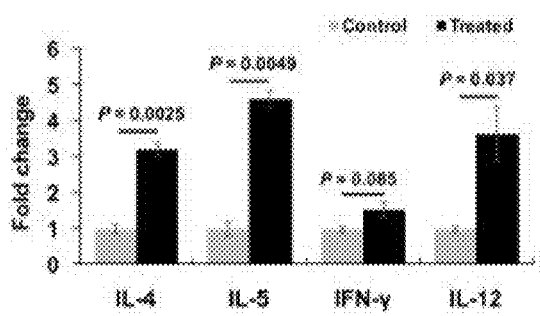
FIG. 50 shows fold-changes of cytokine expression levels in in vitro differentiated T cells after the stimulation with PMA and ionomycin (n=3). Data represent mean±SD

FIGS. 43-50 illustrate in vitro differentiation of purified miCD34$^+$ HSCs to T cells. To determine whether miCD34$^+$ cells were functional as stem cells, they were purified from miPB-IPCs and treated with different inducers (FIG. 43). First, the potential to differentiate into T cells was examined by treating purified miCD34$^+$ cells with recombinant FMS-like tyrosine kinase (FLT)-3 ligand, interleukin (IL)-2, and IL-7 for 3 days. Phase-contrast microscopy revealed marked morphological changes, and the differentiated T cells had numbers of cell clusters in this cytokine-treated group, with some cells released into the supernatant (FIG. 44, right). Cells in the control groups exhibited a smooth surface and failed to show any morphological changes (FIG. 44, left, and FIG. 45). Confocal microscopy demonstrated that the differentiated cells strongly expressed human T cell marker CD4, with weak expression of CD8 (FIG. 46). Flow cytometry further confirmed the differentiation of miCD34$^+$ HSCs into CD3$^+$CD4$^+$CD8$^-$CD38$^+$ T cells at a percentage of 76.93%±3.21% (FIG. 47, n=4), which were CD3$^+$CD4$^+$ TCRαβ$^+$ T cells (82.65%±5.2%, n=3) (FIG. 48). Intracellular staining with T-cell functional markers indicated that these T cells produced Th1 cytokine IL-12 (65.3%±20.1%, n=3) and Th2 cytokines IL-4 (28.5%±9.99%, n=3) and IL-5 (53.9%±11.2%, n=3), with a very low level of interferon (IFN)-γ (0.61%±0.3%, n=3) (FIG. 49). Additional functional tests established the significantly upregulated expression levels of cytokines such as IL-4 (p=0.0025, n=3), IL-5 (p=0.0049, n=3), and IL-12 (p=0.037, n=3) after the treatment with phorbol 12-myristate 13-acetate (PMA) and ionomycin. The level of INF-γ failed to show a marked change (p=0.085, n=3). The data confirmed that the differentiated T cells responded to the stimulation of PMA/ionomycin (FIG. 50). The rapid differentiation of T cells with high efficiency clearly demonstrated that miCD34$^+$ HSCs were converted into functional and definitive hematopoietic progenitors.

Example 9

Ex Vivo Differentiation of miCD34$^+$ HSCs into Other Hematopoietic Lineages

Figure 51:
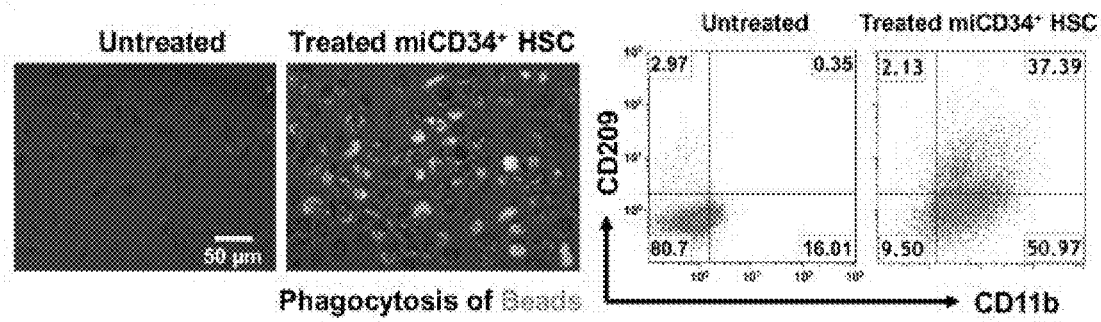
FIG. 51 illustrates differentiation of miCD34$^+$ HSCs into macrophages after treatment with 50 ng/ml M-CSF for 3 days. Differentiated Mφ displayed macrophage markers CD11b and CD209, and exhibited phagocytosis of florescence beads (n=4). Untreated miCD34$^+$ HSCs served as controls.

FIGS. 51-57 show ex vivo multiple differentiations of miCD34$^+$ HSCs. To further examine their potential for differentiation, miCD34$^+$ HSCs were treated with macrophage colony-stimulating factor (M-CSF) for 3 days, whereupon they became adherent, well-spaced cells. Functional analysis established that M-CSF-treated miCD34$^+$ HSCs exhibited strong phagocytosis of fluorescent latex beads (FIG. 51, middle), while untreated cells were mostly negative for this effect (FIG. 51, left). Flow cytometry confirmed that 34.3%±4.3% of the cells were CD11b$^+$CD209$^+$ macrophages (MP), and about 53.66%±3.8% were CD11b$^+$CD209$^-$ macrophages (MΦ) (FIG. 51, right). In contrast, there were only 15.29%±1.5% CD11b$^+$CD209$^-$ macrophages and 0.43%±0.12% CD11b$^+$CD209$^+$ macrophages in untreated miCD34$^+$ HSCs.

Figure 52:
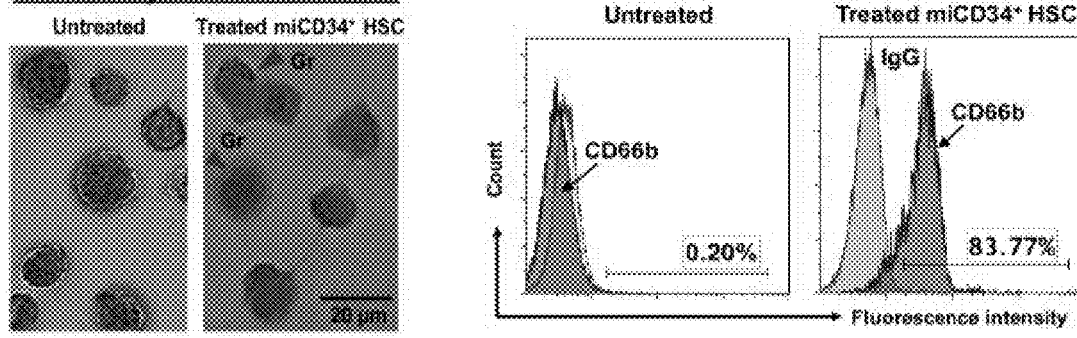
FIG. 52 illustrates differentiation of miCD34$^+$ HSCs into granulocytes after treatment with 100 ng/mL G-CSF+25 ng/mL FLT-3L for 3 days, followed by Wright-Giemsa staining (left), and flow cytometry for granulocyte marker CD66b (n=4). Untreated miCD34$^+$ HSCs served as controls.
Figure 53:
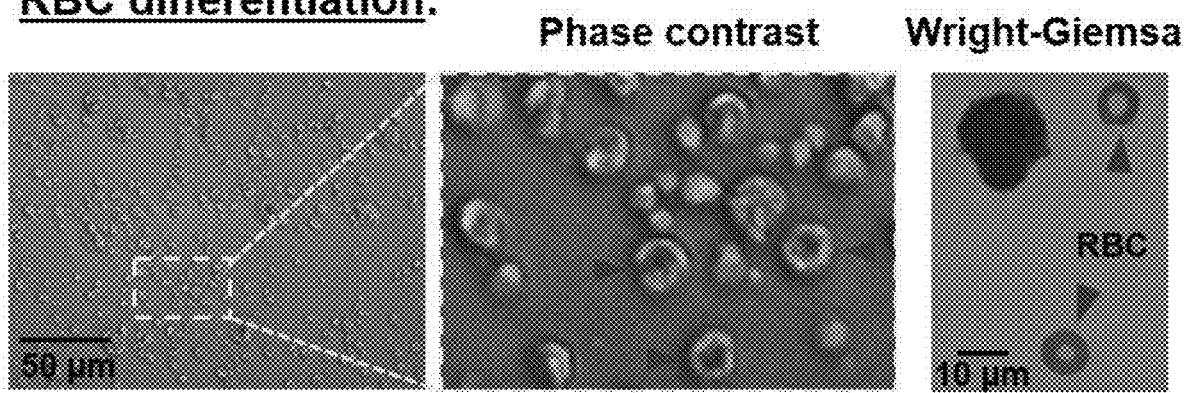
FIG. 53 illustrates differentiation of miCD34$^+$ HSCs into erythrocytes shown by phase-contrast imaging of mature RBCs (indicated by arrows), and by Wright-Giemsa staining with typical morphology of mature RBCs (indicated by arrows) (n=4).
Figure 54:
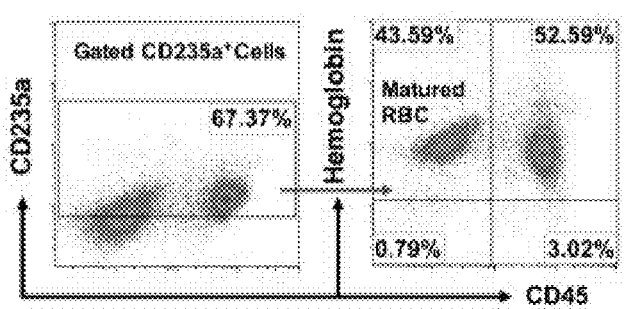
FIG. 54 shows analysis of the percentage of the matured CD45$^-$hemoglobin$^+$ RBCs in the gated CD235a$^+$ cells by flow cytometry (n=4).
Figure 55:
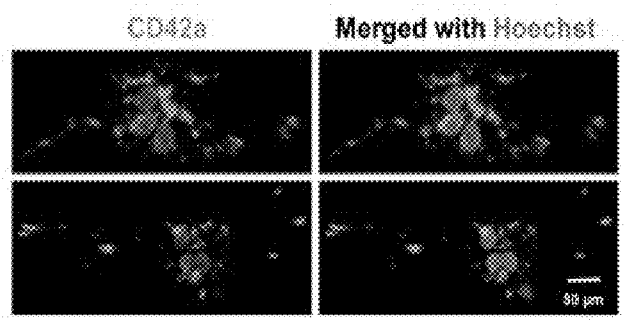
FIG. 55 illustrates differentiation of miCD34$^+$ HSCs into megakaryocytes (MKs)/platelets after the treatment with FLT-3L+TPO for 7 days, exhibiting CD42$^+$ and a polynuclear appearance (n=4).
Figure 56:
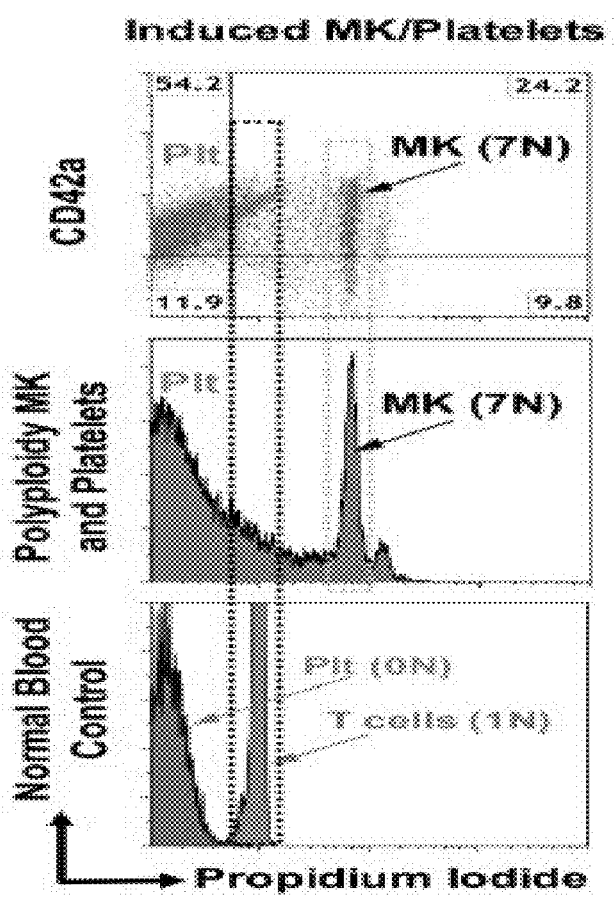
FIG. 56 shows analysis of polyploid MKs post-treatment with FLT-3L+TPO for 7 days, shown by histogram (middle) and dot plot with MK/platelet marker CD42a (top). Normal platelets and T cells from healthy donors served as controls for cells with no nucleus (ON) and one nucleus (1N), respectively (bottom) (n=4).
Figure 57:
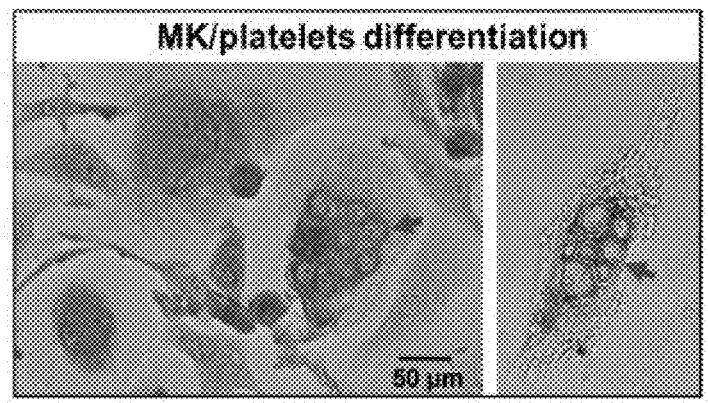
FIG. 57 shows Wright-Giemsa staining illustrating differentiated miCD34$^+$ HSCs with multiple nuclei (indicated by arrows) after treatment with FLT-3L+TPO for 7 days (n=4).

Next, miCD34$^+$ HSCs were induced to granulocyte colony-stimulating factor (G-CSF). After 3 days, 81.14%±3.7% of treated cells displayed the granulocyte-specific marker CD66b, with a reduced nuclear-cytoplasmic ratio and multi-lobed nuclei shown by Wright-Giemsa staining (FIG. 52). However, the untreated miCD34$^+$ HSCs failed to express CD66b and displayed large nuclei, with a large nuclear-cytoplasmic ratio (FIG. 52, n=4). Moreover, after being treated with erythropoietin (EPO) for 5 days, miCD34$^+$ HSCs turned into nucleated cells strongly positive for the erythroid (Er) lineage marker CD235a and facilitated RBC maturation via expulsion of their nuclei with additional EPO treatment, exhibiting a distinctive biconcave shape and enucleated RBCs (FIG. 53). In total, 41.4%±11.46% of cells were terminally differentiated into enucleated CD235a$^+$ CD45$^-$hemoglobin$^+$ RBCs (FIG. 54, n=4). However, untreated cells failed to show these differentiations, or only expressed background levels of these markers. Further flow cytometry analysis demonstrated that the level of hemoglobin expression was increased in the matured RBCs, with the mean fluorescence intensity of hemoglobin$^+$CD45$^-$ mature RBCs at 13.61±4.29, while hemoglobin$^+$CD45$^+$ immature RBCs was 8.29±1.61 (p=0.044, n=4).

Additionally, the commitment of miCD34$^+$ HSCs to MKs and platelets, which are critical for blood clotting, was examined. After treatment with FLT-3 ligand and thrombopoietin (TPO) for 7 days, production of CD42$^+$ MKs was achieved with typical polyploidization (mostly from 2N to 7N) (FIGS. 55-57) and the formation of non-nucleated CD42$^+$ platelets (21.3%±4.1%, n=4) (FIGS. 55-56), yielding 95±17 platelets per MK. Approximately 54% of mature CD42$^+$ platelets were released into the supernatant (FIG. 3F, n=4).

Example 10

In Vivo Differentiation of miCD34$^+$ HSCs into Other Hematopoietic Lineages after Transplant into NSG Mice To further determine multipotent features, purified miCD34$^+$ HSCs were transplanted into irradiated nonobese diabetic (NOD)/Lt-scid/IL2Rγ$^{null}$ (NSG) mice (FIG. 2). FIGS. 58-63 show multiple in vivo differentiations of miCD34$^+$ HSCs after transplantation into the irradiated NSG mice. The chimerism of human CD45$^+$ cells in peripheral blood, spleen, and bone marrow of miCD34 HSC-engrafted mice was examined at 12 weeks, by using flow cytometry analysis with blood cell lineage-specific markers including T cells (CD3$^+$CD4$^+$), B cells (CD19$^+$), monocytes (CD14$^+$), granulocytes (CD66b$^+$), erythroid cells (CD235a$^+$), and megakaryocytes/platelets (CD41b$^+$). To determine the multilineage differentiations of miCD34$^+$ HSCs after transplantation into irradiated NSG mice, only the viable cells from different samples were gated for analysis after excluding propidium iodide (PI)-positive dead cells. The gated human leukocyte common antigen CD45-positive and mouse CD45.1-negative viable cells were analyzed for characterization with different lineage-specific surface markers such as CD3 and CD4 for T cells; CD19 for B cells; CD41b for megakaryocytes/platelets; CD14, CD11b, and CD11c for monocytes/macrophages; CD66b for granulocytes; and CD235a for erythroid cells. SYTO60 was utilized to stain the CD235a$^+$ nucleated erythroid cells. Isotype-matched IgGs served as controls for flow cytometry.

Figure 58:
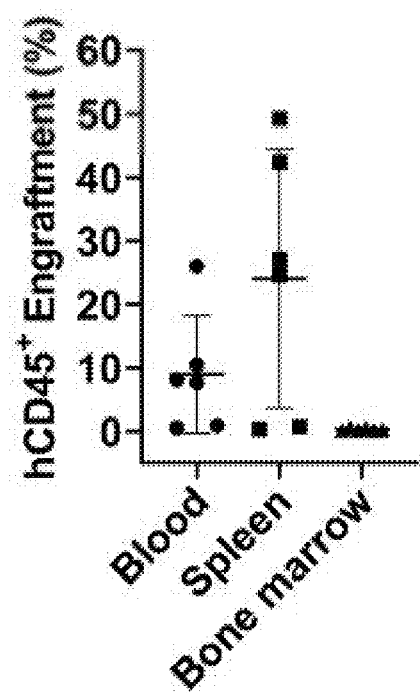
FIG. 58 displays engraftment levels of hCD45$^+$mCD45.1$^-$ cells in peripheral blood, spleen, and bone marrow of miCD34$^+$ HSC-transplanted NSG mice at 12 weeks (3×10$^5$ cells/mouse in 200 µL physiological saline, i.v., n=6).
Figure 59:
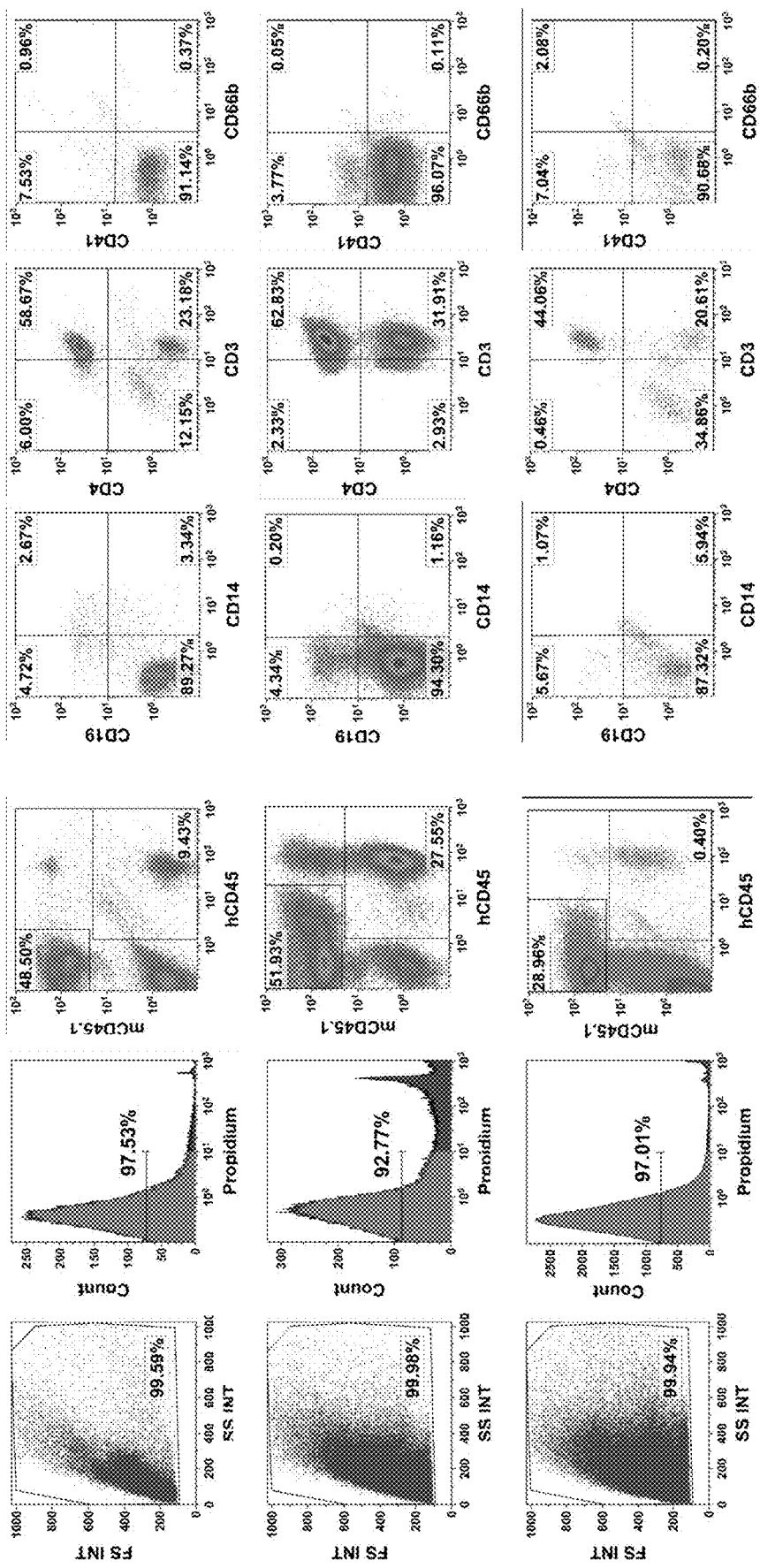
FIG. 59 shows phenotypic characterization of miCD34$^+$ HSCs post engraftment into the irradiated NSG mice (3×10$^5$ cells/mouse in 200 µL physiological saline, i.v., n=5). Tissue samples were collected 12 weeks after the transplantation. Only the viable cells (histogram) were gated for analysis after excluding propidium iodide (PI)-positive dead cells. Gated human leukocyte common antigen CD45-positive and mouse CD45.1-negative viable cells were analyzed. Representative data are from one of three experiments with similar results. Isotype-matched IgGs served as controls for flow cytometry.
Figure 60:
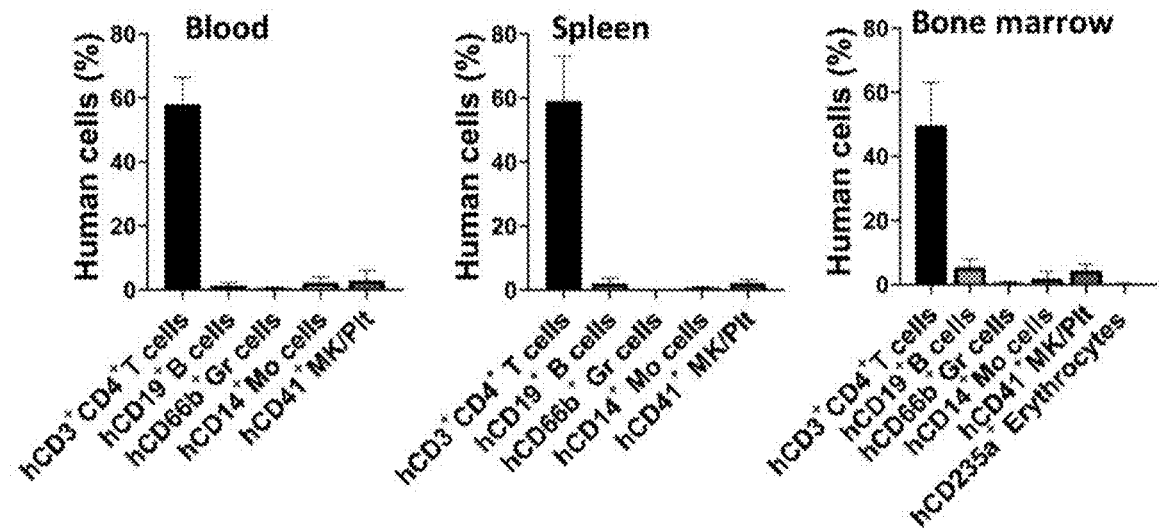
FIG. 60 shows multi-lineage differentiations of miCD34$^+$ HSCs at 12 weeks after transplantation into irradiated NSG mice.
Figure 61:
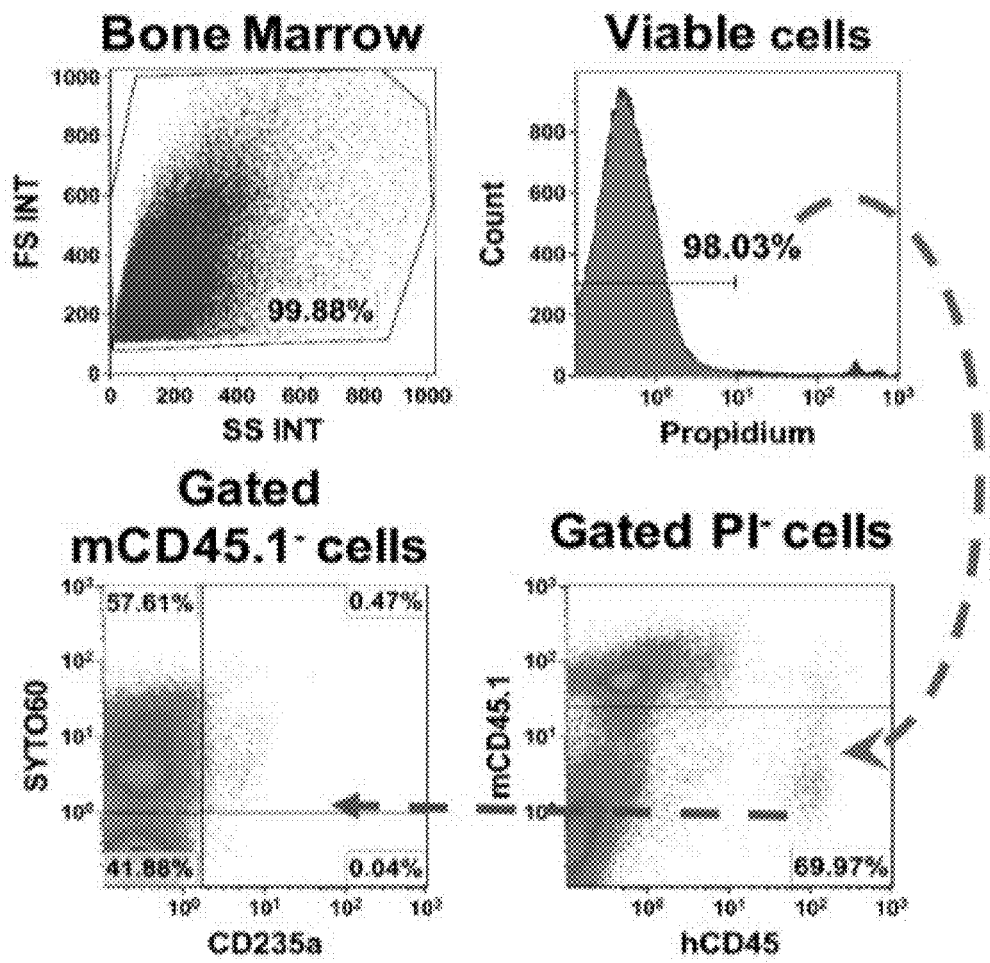
FIG. 61 shows erythroid reconstitution of miCD34$^+$-transplanted NSG mice at 12 weeks (n=6). Only viable cells (histogram) were gated for analysis after excluding propidium iodide (PI)-positive dead cells. SYTO60 was utilized to stain the CD235a$^+$ nucleated erythroid cells.
Figure 62:
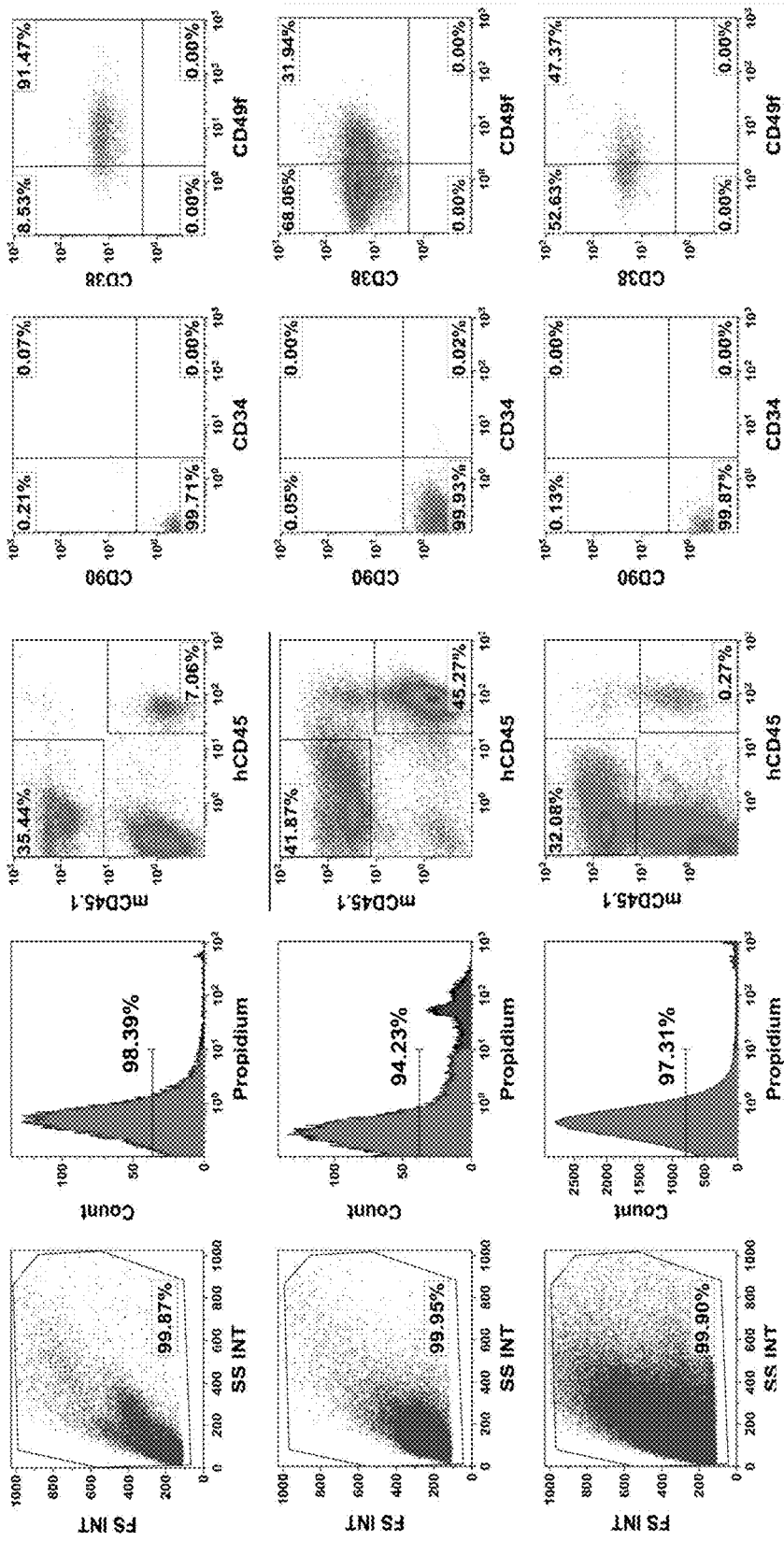
FIG. 62 illustrates characterization of miCD34$^+$ HSCs 12 weeks after engraftment in irradiated NSG mice (n=5). Representative data are from one of three experiments with similar results. Gated human CD45-positive and mouse CD45.1-negative viable cells were analyzed. Isotype-matched IgGs served as controls for flow cytometry.

The engraftment levels of human CD45$^+$ cells in blood (9.93%±9.62%, p=0.035) and spleen (25.37%±21.89%, p=0.018) were much higher than that in bone marrow (0.33%±0.15%) at 12 weeks post-transplantation (FIG. 58, n=6 mice). The miCD34$^+$ HSC-derived CD3$^+$CD4$^+$ T cells remained a predominant population at 57.92%±8.49% of human CD45$^+$ blood cells at 12 weeks after transplantation, with different proportions of other engrafted cells in the blood. Similar data (59%±13.55% of CD3$^+$CD4$^+$ T cells) were obtained from splenocytes of miCD34$^+$ HSC-engrafted mice (FIGS. 59-60, n=5 mice). By comparison, the percentage of miCD34$^+$ HSC-derived CD3$^+$CD4$^+$ T cells in bone marrow was 49.45%±14.01% at 12 weeks, of CD19$^+$ B cells was 5.24%±2.68%, and of CD41b$^+$ megakaryocytes/platelets was 4.3%±2.0%, with CD14$^+$ monocytes at 1.71%±2.36%, CD66b$^+$ granulocytes at 0.51%±0.46%, CD235a$^+$SYTO60$^+$ nucleated erythroid cells at 0.22%±0.13%, and CD235a$^+$SYTO60$^-$ enucleated erythroid cells at 0.08%±0.05% (FIG. 61, n=6 mice). The percentage of CD14$^+$ monocytes was 2.1%±1.81% in the peripheral blood of miCD34$^+$ HSC-transplanted mice. Additional flow cytometry failed to detect the primary phenotype of undifferentiated miCD34$^+$ HSCs. There were few to no human CD34$^+$ cells in peripheral blood (0.07%±0.04%), spleen (0.04%±0.03%), or bone marrow (0.01%±0.01%) of miCD34 HSC-engrafted mice at 12 weeks (FIG. 62, n=5 mice).

Figure 63:
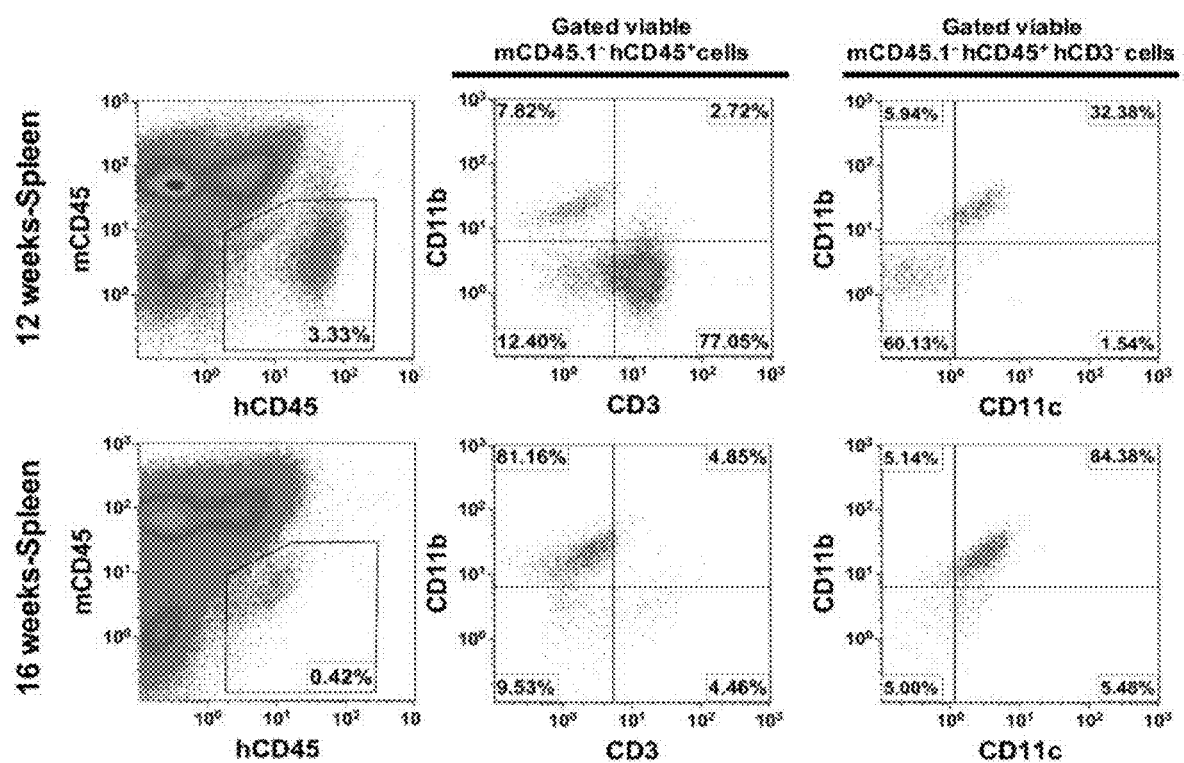
FIG. 63 shows myeloid differentiation of miCD34$^+$ HSCs after transplantation into NSG mice at 12 weeks (top) and 16 weeks (bottom, n=3).

To further confirm miCD34$^+$ HSCs giving rise to monocytes/macrophages (myeloid lineage differentiation), an additional animal study was performed in miCD34 HSC-transplanted mice at 12 and 16 weeks, respectively, by using macrophage-associated markers anti-human CD11b and CD11c mAbs. Flow cytometry demonstrated that the percentage of mCD45$^-$hCD45$^+$hCD3$^-$hCD11b$^+$hCD11c$^+$ macrophages was 75.22%±18.33% in the splenocytes of miCD34$^+$ HSC-transplanted mice at 16 weeks (FIG. 63, n=3). In contrast, the percentage of mCD45$^-$hCD45$^+$hCD3$^+$hCD11b$^-$ T cells declined from 59%±14.01% at 12 weeks to 4.05%±2.87% at 16 weeks (FIG. 63). Thus, the data demonstrated monocyte/macrophage (myeloid) differentiation of miD34$^+$ HSCs after transplantation into irradiated NSG mice. Considering other lineage differentiations (e.g., T cells, B cells, megakaryocytes and red blood cells), these data indicated multi-lineage differentiations of miCD34$^+$ HSCs.

Example 11

Figure 64:
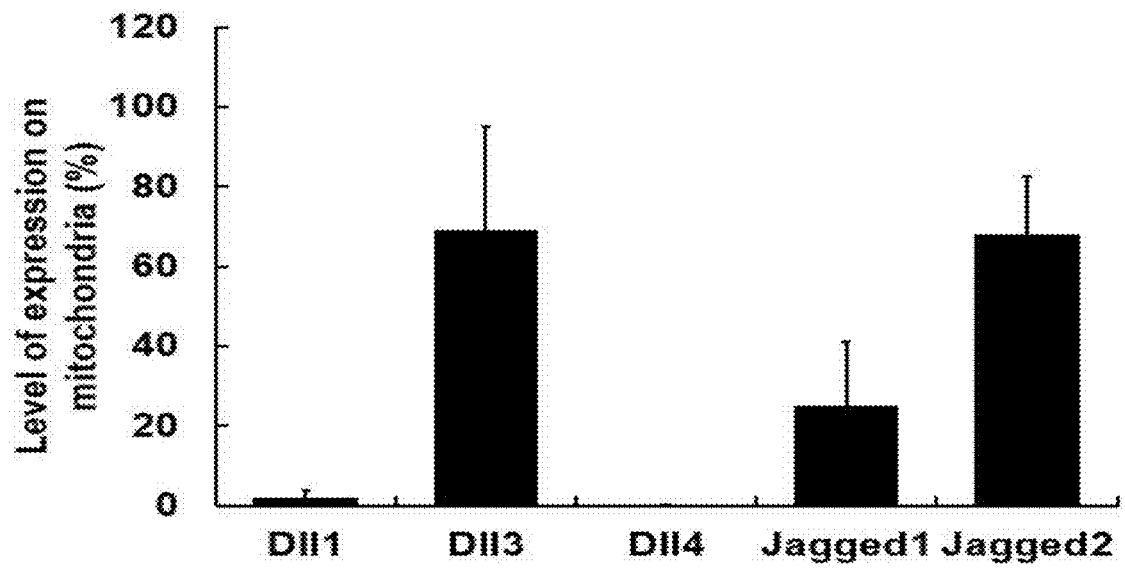
FIG. 64 displays analysis of Notch ligands on platelet-derived mitochondria by flow cytometry (n=3).
Figure 65:
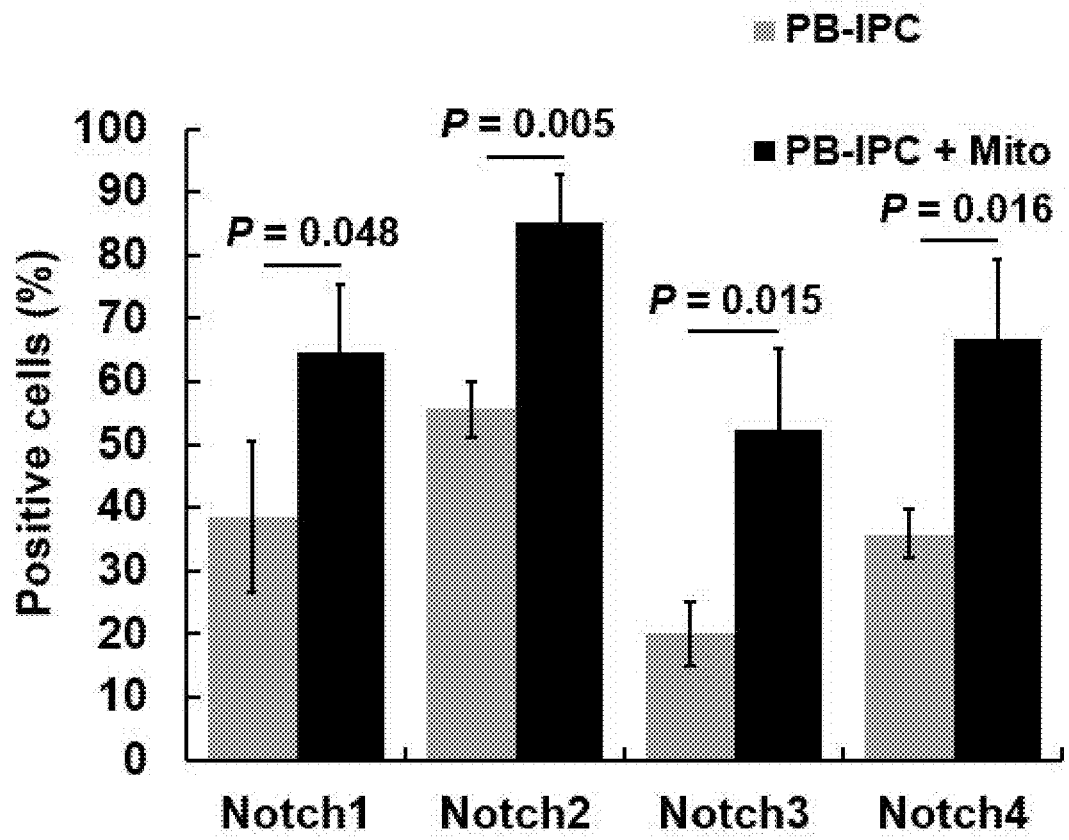
FIG. 65 shows expression of Notch receptors on PB-IPCs by flow cytometry. PB-IPCs were treated with mitochondria for 7 days and collected for flow cytometry. Untreated PB-IPCs served as control. n=3.
Figure 66:
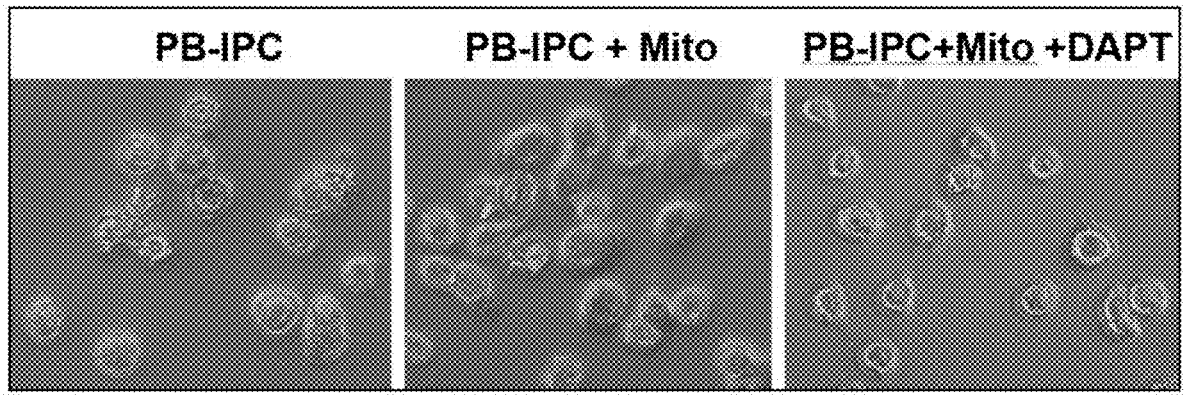
FIG. 66 is phase-contrast imaging showing the morphology of PB-IPCs (left) and treated PB-IPCs in the presence of mitochondria (middle) and mitochondria+DAPT (right). Original magnification: ×200.
Figure 67:
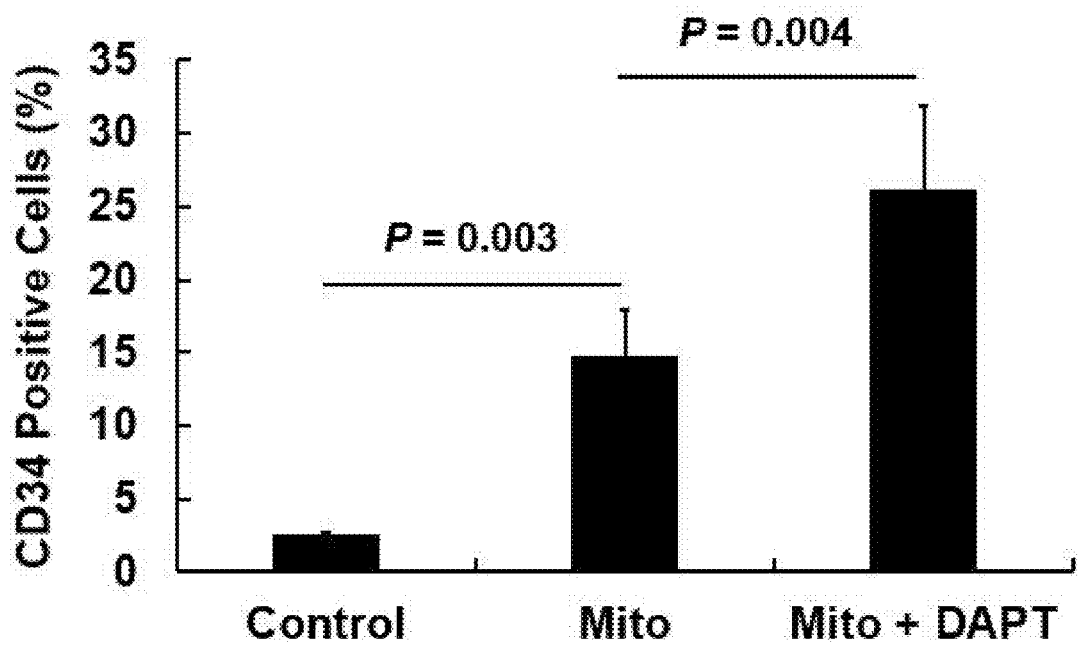
FIG. 67 shows CD34 expression upregulation after the treatment with mitochondria and/or DAPT. DAPT-treated PB-IPCs served as control. n=4. Data represent mean±SD.

Notch Signaling Pathway Contributed to the miCD34$^+$ HSC Differentiation after Treatment with Platelet-Derived Mitochondria Notch signaling has been well established as an essential regulator for HSC generation and differentiation. Specifically, the Notch signaling pathway plays a crucial role in T-cell development and maturation at different stages. Both ex vivo and in vivo data demonstrated multiple differentiations of miCD34$^+$ HSCs. To dissect the molecular mechanisms underlying mitochondrial treatment, the action of Notch signaling during the induction of differentiation of PB-IPCs toward miCD34$^+$ HSCs was explored, as illustrated by FIGS. 64-67. Flow cytometry revealed that mitochondria expressed Notch ligands Jagged 1 (JAG1) (25.13%±16.0%), Jagged 2 (JAG2) (68.04%±14.6%), and Delta-like 3 (DLL3) (69.3%±25.96%), but DLL1 (2.21%±1.74%) and DLL4 (0.23%±0.09%) were not expressed (FIG. 64). The expression levels of Notch receptors 1-4 on PB-IPCs were markedly upregulated after treatment with platelet-derived mitochondria (FIG. 65). To examine the role of Notch signaling in miCD34$^+$ HSC differentiation of mitochondrion-induced PB-IPCs, N—[N-(3,5-difluorophenacetyl)-L-alanyl]-S-phenylglycine t-butyl ester (DAPT) treatment was used to block γ-secretase, an enzyme critical for the release of the Notch intracellular domain (NICD) into the nucleus to initiate gene transcription (FIG. 66). The percentage of CD34$^+$ cells was significantly increased in the group treated with mitochondria plus DAPT (26.2%±5.68%) (FIG. 67). In contrast, treatment with DAPT alone showed a very low ability to induce CD34$^+$ cells (2.59%±0.13%), indicating that mitochondria are required for miCD34$^+$ HSC cell differentiation.

SEQUENCE LISTING

The patent contains a lengthy sequence listing. A copy of the sequence listing is available in electronic form from the USPTO web site (https://seqdata.uspto.gov/?pageRequest=docDetail&DocID=US12091684B2). An electronic copy of the sequence listing will also be available from the USPTO upon request and payment of the fee set forth in 37 CFR 1.19(b)(3).

The invention claimed is:

1. A method of generating multipotent cells, the method comprising the steps of:
providing an adult peripheral blood sample;
isolating peripheral blood insulin-producing cells (PB-IPC) comprising a nuclear membrane including a CXCR-4 protein receptor from said adult peripheral blood sample by applying said adult peripheral blood sample to a hydrophobic surface and said PB-IPC adhering to said hydrophobic surface;
isolating mitochondria comprising an SDF-1 protein ligand from said adult peripheral blood sample;
treating said PB-IPC adhering to said hydrophobic surface with said mitochondria;
said SDF-1 protein ligand of said mitochondria interacting with said CXCR-4 protein receptor of said PB-IPC, resulting in said mitochondria entering nuclei of said PB-IPC; and
said PB-IPC comprising said entered mitochondria forming multipotent cells configured for accommodating reprogramming of said PB-IPC for multipotent differentiation.

2. The method according to claim 1, further comprising the steps of:
isolating peripheral blood-derived mononuclear cells (PBMC) from said adult peripheral blood sample; and
wherein said isolating PB-IPC from said adult peripheral blood sample comprises applying said PBMC to said hydrophobic surface and said PB-IPC adhering to said hydrophobic surface.

3. The method according to claim 1, wherein:
said isolating mitochondria from said adult peripheral blood sample comprises isolating blood platelets from said adult peripheral blood sample and isolating said mitochondria from said blood platelets.

4. The method according to claim 1, wherein:
said isolating mitochondria from said adult peripheral blood sample comprises isolating PBMC from said adult peripheral blood sample and isolating said mitochondria from said PBMC.

5. The method according to claim 1, wherein:
said isolating mitochondria from said adult peripheral blood sample comprises isolating plasma from said adult peripheral blood sample and isolating said mitochondria from said plasma.

6. The method according to claim 1, wherein:
said adult peripheral blood sample comprises a first adult peripheral blood sample from a first source and a second adult peripheral blood sample from a second source;
said first adult peripheral blood sample being used for said isolating said PB-IPC; and
said second adult peripheral blood sample being used for said isolating said mitochondria.

7. The method according to claim 1, further comprising the steps of:
treating said PB-IPC having said entered mitochondria with a promoter for desired differentiated cells; and
said PB-IPC having said entered mitochondria developing into said desired differentiated cells.

8. The method according to claim 7, wherein:
said desired differentiated cells are selected from the group consisting of: macrophage cells, neuronal cells, RPE cells, granulocyte cells, T cells, B cells, red blood cells, megakaryocyte cells, platelet cells, bone marrow cells, stromal cells, osteoblast cells, keratinocytes, hair follicle cells, gland cells, endothelial cells, corneal endothelial cells, cardiomyocytes, muscle cells, epithelial cells, hepatocytes, kidney cells, and islet β cells.

9. A method of generating hematopoietic stem cell (HSC)-like cells, the method comprising the steps of:
providing an adult peripheral blood sample;
isolating PB-IPC comprising a nuclear membrane including a CXCR-4 protein receptor from said adult peripheral blood sample by applying said adult peripheral blood sample to a hydrophobic surface and said PB-IPC adhering to said hydrophobic surface;
isolating mitochondria comprising an SDF-1 protein ligand from said adult peripheral blood sample;
treating said PB-IPC adherent to said hydrophobic surface with said mitochondria;
said SDF-1 protein ligand of said mitochondria interacting with said CXCR-4 protein receptor of said PB-IPC, resulting in said mitochondria entering nuclei of said PB-IPC;
said entered mitochondria upregulating HSC marker CD34 in said PB-IPC; and
said PB-IPC comprising said entered mitochondria forming HSC-like cells configured for accommodating reprogramming of said PB-IPC for hematopoietic differentiation.

10. The method according to claim 9, further comprising the steps of:
isolating PBMC from said adult peripheral blood sample; and
wherein said isolating PB-IPC from said adult peripheral blood sample comprises applying said PBMC to said hydrophobic surface and said PB-IPC adhering to said hydrophobic surface.

11. The method according to claim 9, wherein:
said isolating mitochondria from said adult peripheral blood sample comprises isolating blood platelets from said adult peripheral blood sample and isolating said mitochondria from said blood platelets.

12. The method according to claim 9, wherein:
said isolating mitochondria from said adult peripheral blood sample comprises isolating PBMC from said adult peripheral blood sample and isolating said mitochondria from said PBMC.

13. The method according to claim 9, wherein:
said isolating mitochondria from said adult peripheral blood sample comprises isolating plasma from said adult peripheral blood sample and isolating said mitochondria from said plasma.

14. The method according to claim 9, wherein:
said adult peripheral blood sample comprises a first adult peripheral blood from a first source and a second adult peripheral blood sample from a second source;
said first adult peripheral blood sample being used for said isolating said PB-IPC; and
said second adult peripheral blood sample being used for said isolating said mitochondria.

15. The method according to claim 9, further comprising the steps of:
treating said PB-IPC having said entered mitochondria with a blood cell promoter; and
said PB-IPC having said entered mitochondria developing into differentiated blood cells corresponding to said blood cell promoter.

16. The method according to claim 15, wherein:
said differentiated blood cells are selected from the group consisting of: macrophage cells, granulocyte cells, T cells, B cells, red blood cells, megakaryocyte cells, and platelet cells.

17. A method for multipotent cell generation and medical treatment, the method comprising the steps of:
providing an adult peripheral blood sample;
isolating PBMC from said adult peripheral blood sample;
isolating PB-IPC comprising a nuclear membrane including a CXCR-4 protein receptor from said PBMC by applying said PBMC to a hydrophobic surface and said PB-IPC adhering to said hydrophobic surface;
isolating mitochondria comprising an SDF-1 protein ligand from said adult peripheral blood sample;
treating said PB-IPC adherent to said hydrophobic surface with said mitochondria;
said SDF-1 protein ligand of said mitochondria interacting with said CXCR-4 protein receptor of said PB-IPC, resulting in said mitochondria entering nuclei of said PB-IPC;
said PB-IPC comprising said entered mitochondria forming multipotent cells configured for accommodating reprogramming of said PB-IPC for multipotent differentiation;
treating said PB-IPC having said entered mitochondria with a promoter for desired differentiated cells;
said PB-IPC having said entered mitochondria developing into said desired differentiated cells; and
treating a patient with said desired differentiated cells.

18. The method according to claim 17, wherein:
said desired differentiated cells are selected from the group consisting of: macrophage cells, neuronal cells, RPE cells, granulocyte cells, T cells, B cells, red blood cells, megakaryocyte cells, platelet cells, bone marrow cells, stromal cells, osteoblast cells, keratinocytes, hair follicle cells, gland cells, endothelial cells, corneal endothelial cells, cardiomyocytes, muscle cells, epithelial cells, hepatocytes, kidney cells, and islet β cells.

* * * * *